(12) United States Patent
Reyes-Hernandez et al.

(10) Patent No.: US 10,514,359 B2
(45) Date of Patent: Dec. 24, 2019

(54) DUAL DIELECTROPHERETIC MEMBRANE FOR MONITORING CELL MIGRATION

(71) Applicant: GOVERNMENT OF UNITED STATES OF AMERICA, AS REPRESENTED BY SECRETARY, Gaithersburg, MD (US)

(72) Inventors: Darwin R. Reyes-Hernandez, Clarksburg, MD (US); Brian Nablo, Rockville, MD (US)

(73) Assignee: GOVERNMENT OF THE UNITED STATES OF AMERICA, AS REPRESENTED BY THE SECRETARY OF COMMERCE, Gaithersburg, MD (US)

( * ) Notice: Subject to any disclaimer, the term of this patent is extended or adjusted under 35 U.S.C. 154(b) by 238 days.

(21) Appl. No.: 15/353,342

(22) Filed: Nov. 16, 2016

(65) Prior Publication Data
US 2017/0097319 A1    Apr. 6, 2017

Related U.S. Application Data

(63) Continuation-in-part of application No. 14/791,597, filed on Jul. 6, 2015, now abandoned, which is a continuation of application No. 13/623,925, filed on Sep. 21, 2012, now Pat. No. 9,101,939.
(Continued)

(51) Int. Cl.
*G01N 27/447* (2006.01)
*G01N 33/483* (2006.01)
(Continued)

(52) U.S. Cl.
CPC ....... *G01N 27/44773* (2013.01); *B03C 5/005* (2013.01); *B03C 5/026* (2013.01);
(Continued)

(58) Field of Classification Search
None
See application file for complete search history.

(56) References Cited

U.S. PATENT DOCUMENTS

| 5,376,878 A * | 12/1994 | Fisher | G01N 15/1245 |
| | | | 324/71.4 |
| 2004/0226819 A1* | 11/2004 | Talary | B03C 5/005 |
| | | | 204/451 |

(Continued)

OTHER PUBLICATIONS

Jiang et al. (Microelectronic Engineering 88, 1722-1725) (Year: 2011).*
(Continued)

*Primary Examiner* — Gurpreet Kaur
*Assistant Examiner* — Steven E Rosenwald
(74) *Attorney, Agent, or Firm* — Office of Chief Counsel for National Institute of Standards and Technology

(57) ABSTRACT

A dual dielectropheretic article for monitoring cell migration includes: a membrane to selectively migrate a plurality of cells across the membrane, the membrane including: a first surface to receive the cells; a second surface opposed to the first surface; and a plurality of communication paths disposed in the membrane to provide the selective migration of the cells across the membrane from the first surface to the second surface; a first electrode disposed on the first surface to: provide an electric field for dielectrophoresis of the cells at the first surface; and provide a first potential for monitoring an impedance at the first surface; and a third electrode disposed on the second surface to: provide an electric field for dielectrophoresis of the cells at the second surface; and provide a third potential for monitoring an impedance at the second surface.

20 Claims, 36 Drawing Sheets

Related U.S. Application Data

(60) Provisional application No. 61/537,179, filed on Sep. 21, 2011, provisional application No. 62/256,255, filed on Nov. 17, 2015.

(51) Int. Cl.
*B03C 5/00* (2006.01)
*B03C 5/02* (2006.01)

(52) U.S. Cl.
CPC ..... *G01N 27/447* (2013.01); *G01N 27/44747* (2013.01); *G01N 33/4836* (2013.01); *B03C 2201/26* (2013.01)

(56) References Cited

U.S. PATENT DOCUMENTS

| | | | | |
|---|---|---|---|---|
| 2006/0196772 A1* | 9/2006 | Kim | ................... | B03C 5/026 204/547 |
| 2007/0284254 A1* | 12/2007 | Cho | ................... | B03C 5/005 204/547 |
| 2012/0064567 A1* | 3/2012 | Stakenborg | ............. | B03C 5/005 435/39 |

OTHER PUBLICATIONS

Nablo et al. (Simultaneous Dielectrophoretic Trapping of Cell on Opposite Sides of a Permeable Membrane, 19th International Conference on Miniaturized Systems for Chemistry and Life Sciences, Oct. 25-29, 2015.*

Nablo, B.J., et al., Simultaneous dieletrophoretic trapping of cell opposite sides of a permeable membrane, 2015, International Conference on Miniaturized Systems for Chemistry and Life Sciences, 549-551.

* cited by examiner

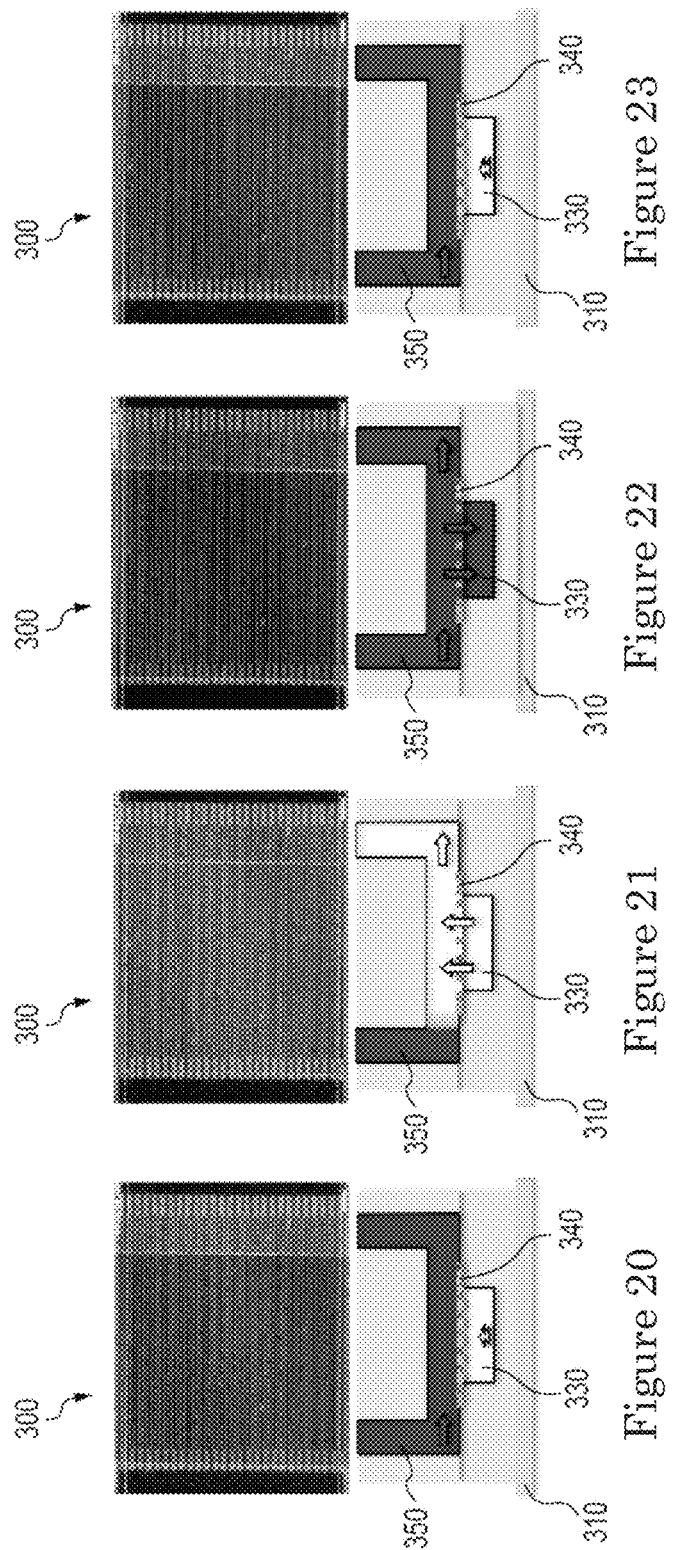

DUAL DIELECTROPHERETIC MEMBRANE FOR MONITORING CELL MIGRATION

CROSS REFERENCE TO RELATED APPLICATIONS

This application claims the benefit of U.S. Provisional Patent Application Ser. No. 62/256,255, filed Nov. 17, 2015, and is a continuation-in-part of U.S. patent application Ser. No. 14/791,597, filed Jul. 6, 2015, which is a continuation of U.S. patent application Ser. No. 13/623,925, filed Sep. 21, 2012, now U.S. Pat. No. 9,101,939, issued Aug. 11, 2015, which claims the benefit of U.S. Provisional Patent Application Ser. No. 61/537,179, filed Sep. 21, 2011, the disclosure of each of which is incorporated herein by reference in its entirety.

STATEMENT REGARDING FEDERALLY SPONSORED RESEARCH

This invention was made with United States Government support from the National Institute of Standards and Technology. The Government has certain rights in the invention.

BRIEF DESCRIPTION

Disclosed is a dual dielectropheretic article for monitoring cell migration, the dual dielectropheretic article comprising: a membrane to selectively migrate a plurality of cells across the membrane, the membrane comprising: a first surface to receive the cells; a second surface opposed to the first surface; and a plurality of communication paths disposed in the membrane to provide the selective migration of the cells across the membrane from the first surface to the second surface; a first electrode disposed on the first surface to: provide an electric field for dielectrophoresis of the cells at the first surface; and provide a first potential for monitoring an impedance at the first surface; and a third electrode disposed on the second surface to: provide an electric field for dielectrophoresis of the cells at the second surface; and provide a third potential for monitoring an impedance at the second surface.

Disclosed also is a process for determining impedance in a dual dielectropheretic article, the process comprising: providing a dual dielectropheretic article; providing a first alternating current (AC) voltage to one of the first electrode or the first probe electrode; monitoring a first electrical response of the first electrode or the first probe electrode that was not provisioned with the first AC voltage; providing a second AC voltage to one of the third electrode or the second probe electrode; monitoring a second electrical response of the third electrode or the second probe electrode that was not provisioned with the second AC voltage; and converting the first electrical response to the impedance at the first surface to determine the impedance of the dual dielectropheretic article.

BRIEF DESCRIPTION OF THE DRAWINGS

The following descriptions should not be considered limiting in any way. With reference to the accompanying drawings, like elements are numbered alike.

FIG. 10 shows a graph of percent viability of P19 cells on the hCAM composition of the present subject matter;

FIG. 20 shows another microfluidic device in accordance with the present subject matter and a schematic illustration of two fluids flowing in the device;

FIG. 21 shows the device of FIG. 20 and two fluids flowing in the device;

FIG. 22 shows the device of FIG. 20 and two fluids flowing in the device;

FIG. 23 shows the device of FIG. 20 and two fluids flowing in the device;

DETAILED DESCRIPTION

Figure 1:
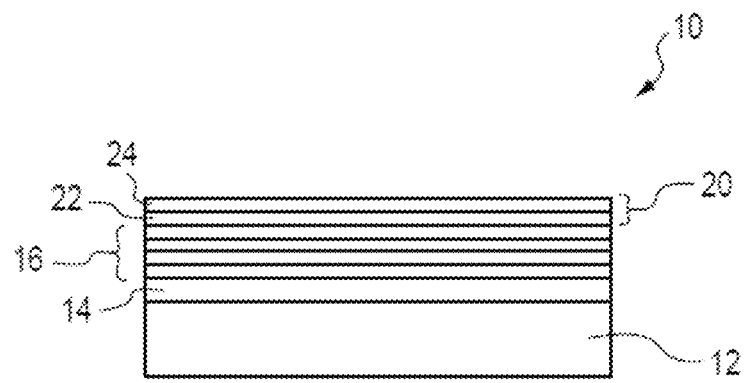
FIG. 1 shows a schematic cross sectional illustration of a glass slide assembly in accordance with the present subject matter.

A detailed description of one or more embodiments is presented herein by way of exemplification and not limitation.

It has been discovered that an dual dielectropheretic article herein provides real-time or quantitative measurements of cell migration and invasion through a porous membrane. Advantageously, the dual dielectropheretic article includes micro fabricated electrical components disposed on opposing surfaces the porous membrane to produce electronic signals from which a movement of cells across the membrane is determined as the cells traverse the membrane. The membrane can include pores such that movement of cells through the pores are acquired by optical microscopy.

Hybrid Cell Adhesive Materials

The membrane supports dielectrophoresis (DEP) of cells on one or both sides of the membrane. In this regard, a system is provided that combines DEP with a hybrid cell adhesive material (hCAM) to allow for cell entrapment and cell function, as demonstrated by cell differentiation into neuron-like cells (NLCs). The hCAM, including polyelectrolytes and fibronectin (FN), is adapted to function as an instantaneous cell adhesive surface after dielectrophoretic (DEP) manipulation, and to support long term cell function (cell proliferation, induction, and differentiation). Pluripotent P19 mouse embryonal carcinoma cells flowing within a microchannel were attracted to the DEP electrode surface and remain adhered onto the hCAM coating under a fluid flow field after the DEP forces were removed. Cells remained viable after DEP manipulation for up to 8 days, during which time the P19 cells were induced to differentiate into NLCs. This approach could have further applications in areas such as cell-cell communication, three-dimensional cell aggregates to create cell microenvironments, and cell co-cultures. Although embodiments herein are described with regard to cells, it will be understood that the subject matter is applicable to a wide array of bioparticles.

As used herein, "bioparticle" refers to any material shed from an organism and is typically biological in nature. The bioparticles can be classified according to any of the general biological classes of materials. For example, the bioparticle can be proteinaceous (e.g., a protein, peptide, or antibody), nucleic acid-containing (e.g., a nucleobase, nucleotide, oligonucleotide, or nucleic acid), lipid-containing (e.g., fatty acid-containing), steroidal, one or more small biological molecules, other types of biological material, and combinations thereof. Some more specific examples of bioparticles include cells (e.g., skin-derived or epidermis cells), protein structures, hair, pathogenic and non-pathogenic bacterial, viral, fungal, protozoal or other organisms, and plant-derived material (e.g., pollen). Shed material from the skin is particularly plentiful and includes particles from the outer skin layer (e.g., stratum corneum) and other skin layers that contain keratin. Though the bioparticles are largely organic, they may also be inorganic. For example, the bioparticle can be a mineral, such as talc. The bioparticle also need not be natural in composition, but may be synthetic (e.g., particulates used in cosmetics or other toiletries). Often, the bioparticles are constructed of aggregations of molecules or other bioparticles. Such aggregations include cells, viruses, pollen grains, skin flakes, hair, bacteria, and several other types of aggregations of organic and inorganic molecules.

In certain embodiments, the effects of different cell adhesive materials on the attachment and function of P19 cells were assessed to determine the most appropriate surface on which to investigate cell function (specifically differentiation) after DEP trapping and subsequent removal of the electric field. P19 cells are a pluripotent cell line that have the ability to differentiate through several pathways in vitro, specifically neuronal, cardiac muscle and skeletal muscle. The ability of P19 cells to differentiate after DEP manipulation would demonstrate the successful generation of a cell adhesive material that allows long term culture. This can be accomplished in performing experiments with cells that are arranged by DEP. Embodiments herein include an hCAM prepared from FN and a poly(allylamine hydrochloride) (PAH) layer on top of polyelectrolyte multiple layers (PEMs) that provide instantaneous cell anchorage after DEP trapping. Furthermore, long term cell viability (more than a week) and differentiation were also attained, demonstrating the utility of the hCAM for long term in vitro cell experiments.

In some embodiments, two sets of separate investigations were performed to identify a biocompatible coating that allows P19 cell adhesion and growth under the low conductivity media sucrose and under electric fields. Tissue culture polystyrene (TCPS), polystyrene (PS) (spin coated plasma oxidized), cell culture media (CCM) pretreated PS, poly-L-lysine, (PAH/PSS)2PAH, collagen I (Col I), and fibronectin (FN) were evaluated as adhesion substrates for cells suspended in sucrose for 15 min, the maximum time typically required for DEP positioning of cells. The assessments described herein were based on counting the number of adhered cells remaining on the surface and counting the fraction of rounded cells (quantitative cell morphology assessment) as well as qualitative evaluation of cell morphology versus the morphology of the cells on the TCPS substrate 24 hours after cell seeding. Previously, it was found that PEMs were able to capture cells trapped with DEP forces, but the compatibility of PEMs for long term cell culture was not evaluated. The data indicated that the cells adhered well to the (PAH/PSS)2PAH when the cells were seeded in cell culture media (700 cells/mm2). But when the cells were seeded in sucrose, fewer than 9 cells/mm2 were observed. Cell seeding in sucrose significantly decreased the number of adhered cells on collagen, PAH, spin coated PS with plasma treatment and fibronectin. Sucrose did not appear to influence adhesion on poly-lysine and TCPS surfaces. Because it was found that sucrose did not appear to decrease cell function when used in tissue culture polystyrene, it was hypothesized that sucrose may decrease the adhesive nature of the substrate by blocking or removing the proadhesive molecules. During the substrate evaluation, it was noted that although cells remain adhered to collagen I and poly-lysine after 24 h, greater than 40 and 80 percent of the cells were rounded and appeared unhealthy. Qualitative evaluation of the morphology suggested that the P19 cells that remained adhered to the FN substrate had a spread appearance similar to the cells on the TCPS dish. Overall, the data from this evaluation suggested that the FN substrate best supports growth of the P19 cells when they are seeded from a sucrose solution.

Figure 2:
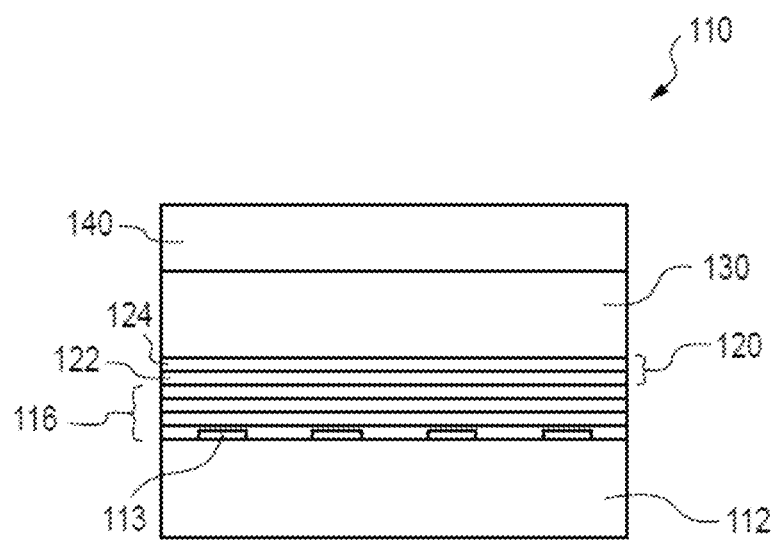
FIG. 2 shows a schematic cross sectional illustration of a flow device in accordance with the present subject matter.

Additional assessments showed that when trapping P19 cells under a continuous flow field using DEP and FN-coated substrates, all the cells detached at the moment the DEP forces were stopped. To take advantage of the ability of FN to promote long term adhesion and growth of the P19 cells and the PEMs that support capture of cells after DEP forces are applied, an hCAM composition was prepared from FN, PEMs, and a PAH layer on top of the FN. A schematic of the hybrid material used in two layered systems is shown in FIG. 1 and FIG. 2. The combination of FN adsorbed to PEMs (negatively charged PSS as the outermost layer) and PAH on top of the FN was tested for cell adhesiveness under DEP conditions and long term cell viability. The cell adhesiveness of the hCAM was assessed first under cell seeding conditions in sucrose. Silanized coverslips were polystyrene coated and then plasma oxidized before depositing the layers of the polyelectrolytes (see FIG. 1). The procedure to deposit the hCAM was similar for the experiments carried out on the DEP electrodes (see FIG. 2), differing only in the PEMs being directly deposited on the ITO/glass surface and not on a polystyrene layer. Specifically, a schematic side view of glass coverslip assembly 10 is shown in FIG. 1 and DEP device 110 is shown in FIG. 2, both with hCAM deposited on top. The assembly 10 in FIG. 1 includes glass substrate 12, layer of polystyrene (PS) 14 disposed on glass substrate 12, a collection of PEMs 16 disposed on layer of polystyrene 14, and layer 20 of hCAM material disposed on collection of PEMs 16. PEMs 16 are shown as including four (4) layers, but it will be understood that a greater number or lesser number of layers could be utilized. Layer 20 of hCAM includes underlayer 22 of FN and outerlayer 24 of PAH disposed on underlayer 22. Flow DEP device 110 and particularly, a microfluidic flow device, can include glass substrate 112, two or more electrically conductive electrodes 113 such as indium tin oxide (ITO) electrodes, a collection of PEMs 116 disposed on glass substrate 112 and the one or more electrodes 113, and layer 120 of hCAM material. The hCAM material typically includes underlayer 122 of FN and outerlayer 124 of PAH disposed on underlayer 122. Device 110 also includes flow channel 130 that can be bounded by wall 140 formed from a suitable material such as polydimethyl siloxane (PDMS). The hCAM includes a layer of FN and PAH on top of four layers of polyelectrolytes (PAH/PSS)2, which in turn were deposited onto polystyrene-coated coverslips as in FIG. 1 and ITO electrodes as in FIG. 2. The microchannel is molded in PDMS and reversibly bound onto the device.

Figure 3:
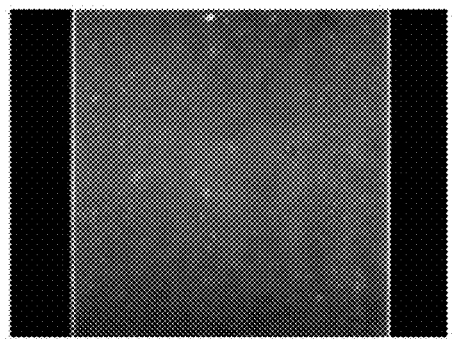
FIG. 3 shows an image of a layer of PAH-FITC on a collection of PEMs.
Figure 4:
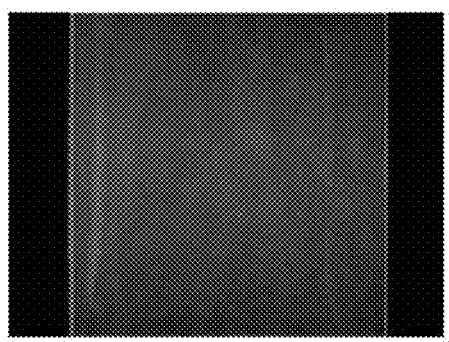
FIG. 4 shows an image of a layer of FN-ROX on a collection of PEMs.
Figure 5:
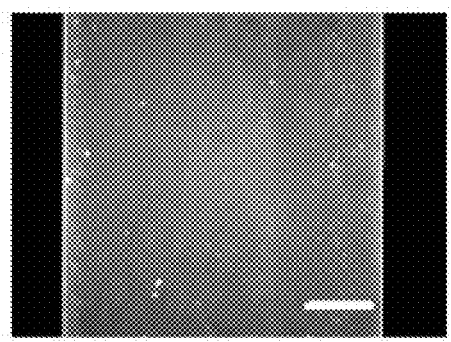
FIG. 5 shows an image of PAH-FITC deposited on FN-ROX, and both deposited on PEMs.

The hCAM was examined by depositing fluorescently labeled FN and PAH in microfluidic channels and imaging the channels using fluorescence microscopy as shown in FIG. 3, FIG. 4, and FIG. 5. Specifically, images of fluorescently labeled components of the hCAM are shown in FIG. 3, FIG. 4, and FIG. 5. FIG. 3 shows PAH-FITC and FIG. 4 shows FN-ROX deposited on four layers of polyelectrolytes ((PAH/PSS)2). FIG. 5 shows PAH-FITC deposited on FN-ROX, and both on (PAH/PSS)2. The interior region in FIG. 5 denotes the overlapping of the labeled PAH and FN throughout the surface. The scale bar in FIG. 5 is 200 µm. Fluorescently labeled FN (FN-ROX) and PAH (PAH-FITC) were deposited separately (FIG. 3 and FIG. 4) and then together with PAH-FITC on top of FN-ROX, and in all cases they were deposited on top of 4 layers of polyelectrolytes ((PAH/PSS)2). All the images in FIG. 3, FIG. 4, and FIG. 5 were taken after the channels were rinsed and then refilled with PBS. The fluorescence from PAH-FITC on (PAH/PSS)2 is shown in FIG. 3. In FIG. 3, it was determined that PAH-FITC homogenously coats the surface. FIG. 4 shows FN-ROX bound to (PAH/PSS)2. In FIG. 4, it was determined that the FN-ROX, also covers the surface of the channel. FIG. 5 shows PAH-FITC deposited onto FN-ROX, which was first deposited on (PAH/PSS)2. In FIG. 5, darker regions (excluding the edges) indicate the areas where there is a thin layer of the materials, whereas the lighter areas are observed at the edges of the channel where more accumulation of the deposited PEMs was previously observed. The PBS rinse was performed by aspirating from the outlet reservoir using a vacuum pump. The fluorescence intensities remained constant after rinsing, suggesting that the hybrid layer is stable in a fluid flow field.

Figure 6:
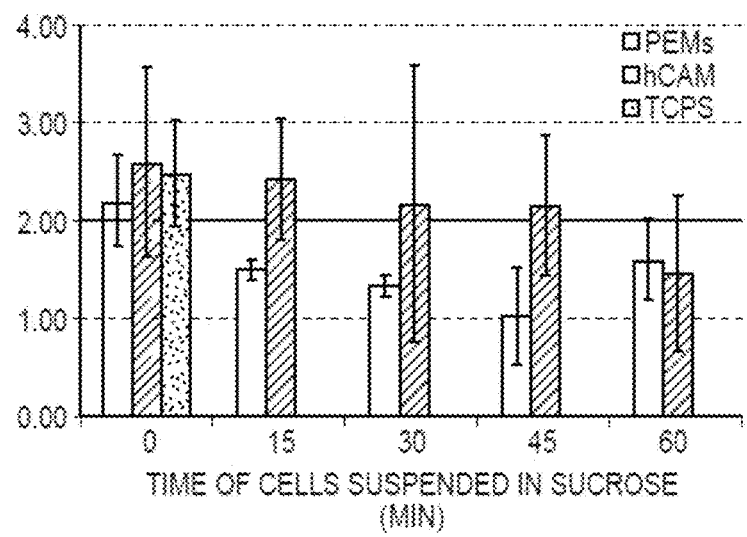
FIG. 6 shows a graph showing the change in the number of cells seeded in sucrose media after 24 hours and exposed to PEMs, hCAM, and TCPS.

Additionally, the proliferation and viability of P19 cells seeded in sucrose on the hCAM surface were assessed. FIG. 6 shows the change in the number of cells seeded in sucrose media after 24 h. The cells were exposed to sucrose media for 0 min, 15 min, 30 min, 45 min, and 60 min, after which cell culture media (CCM) was added to the well to substitute the sucrose media. This plot shows a tendency of the hCAM to allow for similar levels of cell proliferation, specifically, cell doubling (see the crosshatched bars in FIG. 6) at all time points. The doubling value was calculated by dividing the number of cells at 24 hours by the number of cells seeded at 0 h. A value of 2 is expected if the number of cells doubled. Cells exposed to CCM only (0 minutes in sucrose) and sucrose for 15 min, 30 min, and 45 minutes showed the best results for the hCAM surface. Only the 60 minutes sample, on the hCAM showed a value of less than 2. On the other hand, the cells seeded on PEMs do not exhibit cell doubling except for those that were seeded in CCM (0 minutes in sucrose). The average doubling value obtained for P19 cells seeded in sucrose on the hCAM and on PEMs were 2.06±0.41 and 1.38±0.25, respectively. These results demonstrate the compatibility of the hCAM with DEP conditions (sucrose media), which is critical to successfully generate DEP trapping forces that will hold cells in place. The PEM alone, on the other hand, was incapable of promoting P19 cell attachment and proliferation (cell doubling) when cells were suspended in sucrose.

Figure 7:
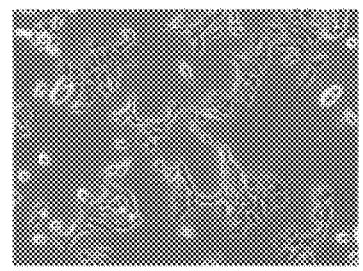
FIG. 7 shows an image showing P19 cells 24 hours after seeding on TCPS.
Figure 8:
FIG. 8 shows an image showing P19 cells 24 hours after seeding on PEMs.
Figure 9:
FIG. 9 shows an image showing P19 cells 24 hours after seeding on hCAM.

P19 cell morphology after 24 hours was also evaluated, in which FIG. 7, FIG. 8, and FIG. 9 show P19 cells 24 hours after seeding on TCPS, PEMs, and hCAM, respectively. These images show P19 cells that were not exposed to sucrose (FIG. 7) and cells that were exposed to sucrose (FIG. 8 and FIG. 9) for 15 minutes and later replaced with CCM. The morphology of the P19 cells was affected by sucrose exposure and the surface on which they were plated. Cells on PEMs appeared more rounded, indicating weak attachment to the surface of the PEMs (see white arrow heads in FIG. 8). In some cases, they formed elongated structures larger than the average surface area of the cells (see black arrowhead in FIG. 8). Conversely, P19 cells on hCAM showed similar morphology to the cells seeded in CCM on TCPS and similar doubling values (doubling value=2.5 on TCPS versus 2.6 on hCAM). Specifically, FIG. 6, FIG. 7, FIG. 8, and FIG. 9 are directed to proliferation of P19 cells seeded on PEMs and hCAM after resuspension in sucrose. FIG. 6 shows the change in the number of cells seeded in sucrose media after 24 hours (doubling value). Values are approximately 2 for cells on the hCAM surface, whereas cells on PEMs show values of less than 2 when cells were suspended in sucrose (averages of 89 cells/frame, 44 cells/frame, and 25 cells/frame were observed for TCPS, PEMs, and hCAM, respectively; error bars represent one standard deviation). FIG. 7 shows representative phase contrast images of P19 cells on TCPS, PEMs (FIG. 8), and on hCAM (FIG. 9) 24 hours after seeding. Cells on PEMs and hCAM were suspended in sucrose for 15 min. Black arrowhead in (FIG. 8) indicates cell with larger than average surface area, and white arrowheads indicate weak cell attachment to the surface of the PEMs. The scale bar in FIG. 8 is 100 µm.

The viability of P19 cells was assessed using a live/dead viability assay from Invitrogen Corp. The viability results in FIG. 10 show that 99% or more of the cells were viable 48 hours after cell seeding on hCAM, and 96% of the cells were viable on the PEMs. Also, the results indicate that P19 cells can be exposed to sucrose for at least 60 minutes with no significant change in viability. Specifically, FIG. 10 illustrates percent viability of P19 cells on the hCAM. Cells are 99% viable or more at all sucrose exposure times. The percentage of live cells is represented by the gray color bars, whereas the dead cells (cross hatched bars) complete the 100% of the cells in each bar with ≤1% dead cells.

Figure 11:
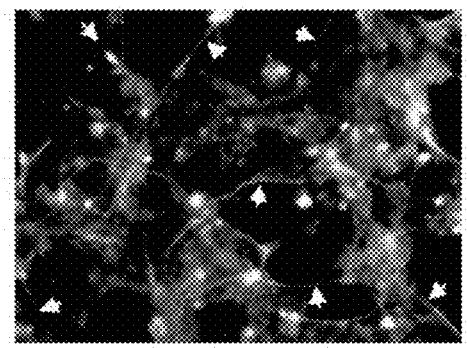
FIG. 11 shows an image of P19 cells on adhesive TCPS.
Figure 12:
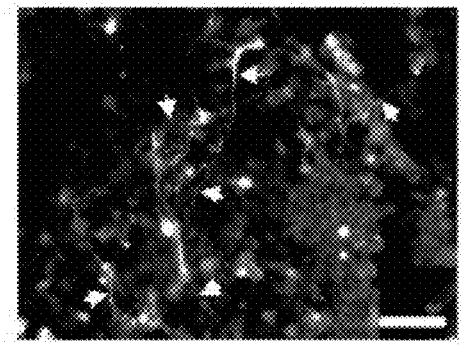
FIG. 12 shows an image of P19 cells on (PAH/PSS)2 FN.
Figure 13:
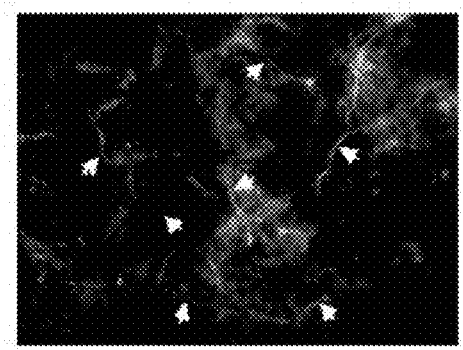
FIG. 13 shows an image of P19 cells on hCAM.

To fully evaluate the function of P19 cells after 15 minutes of sucrose exposure, adhered P19 cells on TCPS (control, no sucrose exposure), (PAH/PSS)2/FN, and hCAM were differentiated. Cell differentiation was evaluated using a procedure that was modified from previous reports on P19 cell differentiation. The present process allows for the plating of dissociated cells on adhesive surfaces and induction of differentiation after cell attachment on the substrates. Cell differentiation was carried out by first exposing P19 cells to sucrose for 15 min, exchanging the sucrose for low serum/retinoic acid induction media and after 4 days exchanging the low serum media for normal cell growth media. FIG. 11 shows an image of immunostained P19 cells that were induced to differentiate on adhesive TCPS without exposure to sucrose. Neurofilaments and neurofilament proteins in the cytoplasm of the NLCs are stained with a neurofilament antibody. Neurofilaments are observed as cables connecting the cells, and the arrowheads point at neurofilaments generated by the P19 cells, which differentiated into NLCs. FIG. 12 and FIG. 13 show P19 cells differentiated on (PAH/PSS)2FN and on the hCAM, respectively. Each image shows the clear formation of neurofilaments after P19 cells were induced and differentiated on the surfaces. This indicates P19 cells can be induced to become NLCs and form neurofilaments even when the cells are fully adhered onto these substrates during the programming and induction process. Specifically, FIG. 11, FIG. 12, and FIG. 13 show immunofluorescence images of differentiated P19 cells induced on TCPS (FIG. 11), on (PAH/PSS)2FN (FIG. 12), and the hCAM (FIG. 13). Neurofilaments were immunostained, demonstrating neuronal differentiation (see arrows). Induction and differentiation were possible while cells were adhered on all surfaces. The scale bar in FIG. 12 is 50 µm.

Figure 14:
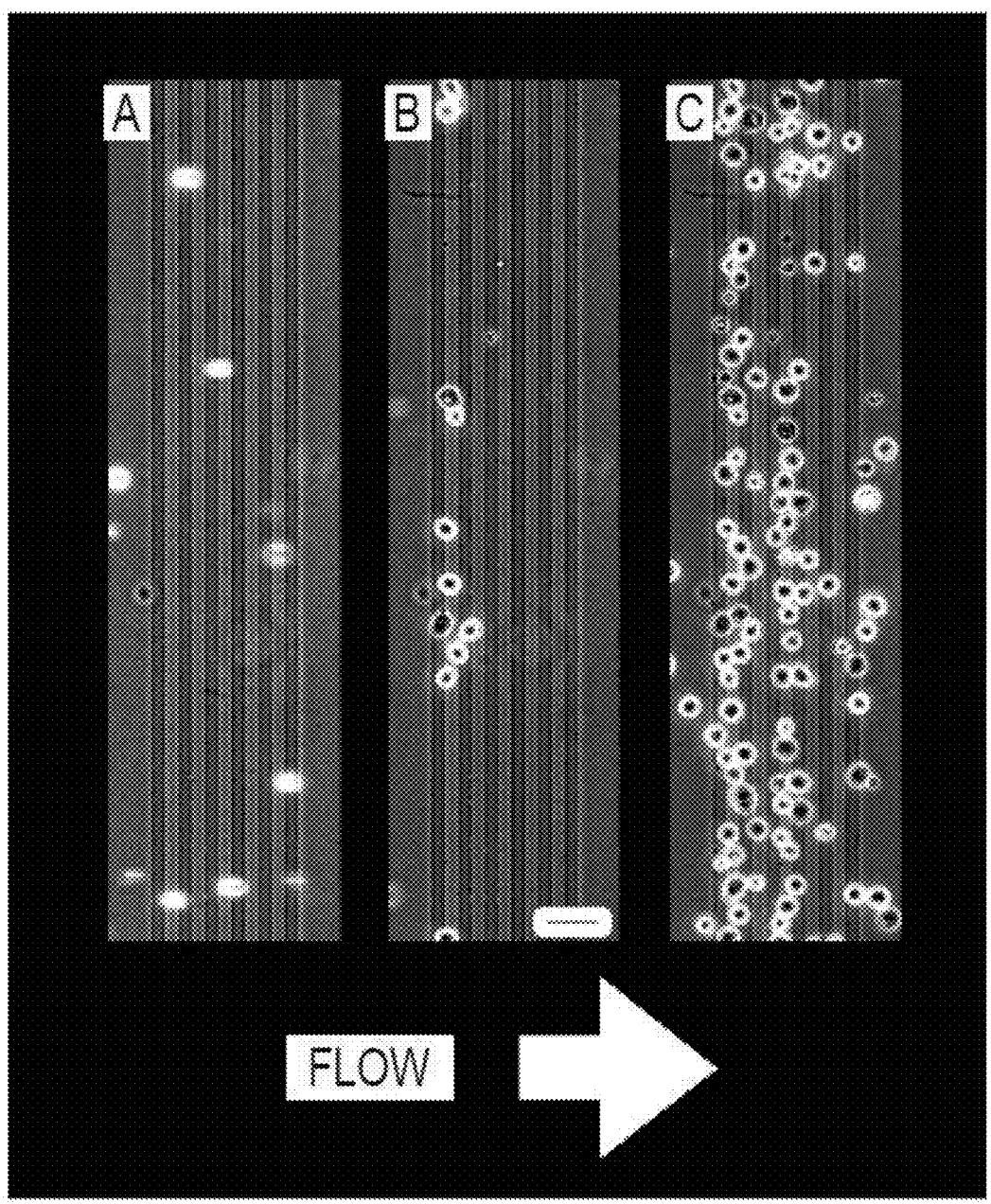
FIG. 14 shows DEP trapping of P19 cells on hCAM.
Figure 15:
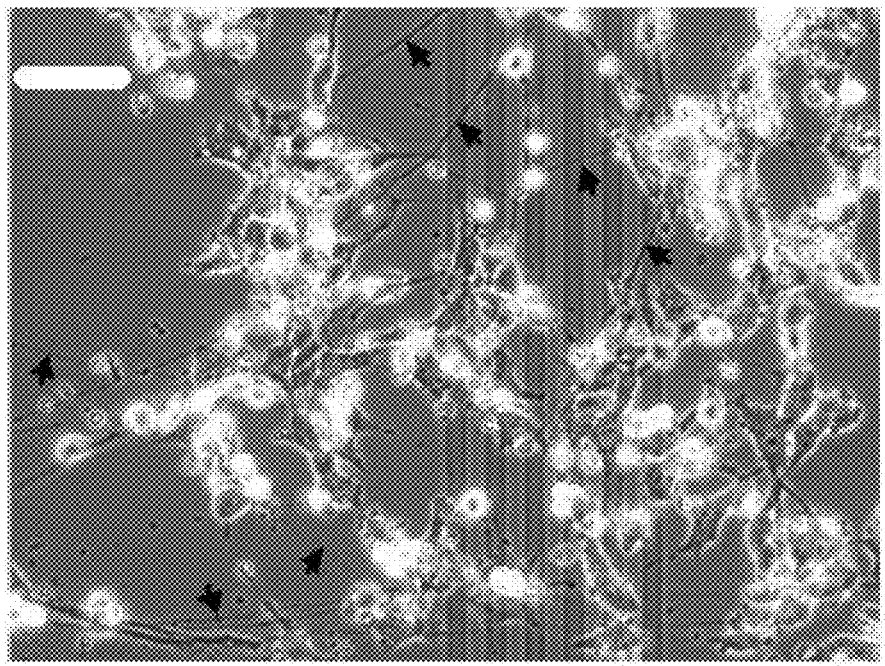
FIG. 15 shows an image of P19 cell differentiation after DEP trapping.

As previously described, previous attempts to use PEMs for long term cell experiments demonstrated that polyelectrolytes alone did not maintain cell viability after exposure to DEP conditions (sucrose and electric fields). The hybrid surface of the present subject matter, hCAM, showed the ability to accommodate long term P19 cell growth and function after the surface and the cells were exposed to sucrose. Once it was determined that the hCAM could support long term cell function, the engineered material was used with a DEP device and all conditions used for such experiments. The combination of polyelectrolytes and FN on the ITO electrodes produced a surface suitable for DEP-based cell anchorage, proliferation, and differentiation as shown in FIG. 14 and FIG. 15. FIG. 14 shows a sequence of cell movement in a fluid flow field and the application of DEP forces.

Specifically, FIG. 14 illustrates DEP trapping of P19 cells on hCAM. Panel A shows P19 cells flow down the channel passing over the DEP ITO electrodes (vertical dark gray lines) without being trapped. The ITO electrodes were initially off for a few seconds before they were turned on. As shown in panel B, once the electrodes were turned on, P19 cells were trapped by the DEP forces and then anchored onto the hCAM. Panel C shows ITO electrodes were turned off, and P19 cells trapped on the surface remained adhered to the hCAM even while exposed continuously to a fluid flow field. The scale bar in Panel B is 50 µm. More specifically, Panel A in FIG. 14 shows a phase contrast image where P19 cells are flowing down the channel (left to right) in the absence of DEP. The cells are passing over the electrodes without being trapped. The first cells trapped when the DEP forces are active are shown in Panel B of FIG. 14. The applied voltage was varied throughout the investigation from 7 V to 3 V at a frequency of 30 MHz (electric fields between 7,000 V/cm to 3,000 V/cm) in order to start trapping cells on the first pair of electrodes and later cell trappings on subsequent electrodes as the voltage was lowered. Panel C in FIG. 14 shows the P19 cells trapped at the end of the DEP experiment when voltage is no longer being applied. Cells remained trapped under the fluid flow field without an electric field present.

Figure 16:
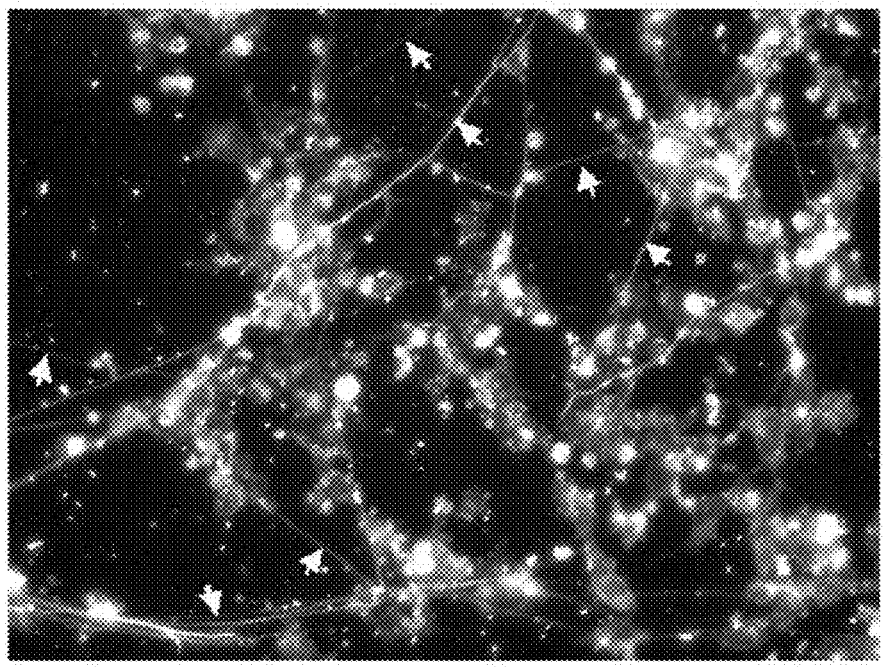
FIG. 16 shows an image of P19 cell differentiation after DEP trapping and 8 days in culture.

Cells that were trapped under DEP conditions on the hCAM surface in a fluid flow field were later induced to differentiate into NLCs. FIG. 15 and FIG. 16 illustrate P19 cell differentiation after DEP trapping and 8 days in culture in a microfluidic system. The phase contrast image (FIG. 15) shows a number of neurofilament projections connecting the cells once they have differentiated (see arrowheads), which is indicative of successful P19 cell differentiation into NLCs. The ITO electrodes can be seen (gray vertical lines) in the images where cells grew out after initial trapping. Cell migration away from the electrode occurred during the 6 days (2 days in CCM and 4 days in induction media) required for differentiation.

Immunostaining of neurofilaments better illustrates the complexity of the interconnections among the cells. The fluorescence image in FIG. 16 more prominently shows the projections P19 cells produced after the differentiation process. The presence of stained neurofilament processes and staining in the cytoplasm of NLCs confirms the suitability of the hCAM as a surface that provides for the anchorage of P19 cells under DEP conditions in microfluidics (sucrose media, electric fields, and fluid flow field), and that simultaneously allows the cells to function properly in their ability to differentiate after the complete process.

Specifically, FIG. 15 and FIG. 16 depict differentiated P19 cells within a microchannel after DEP trapping and induction. FIG. 15 shows phase contrast image of NLCs (differentiated P19 cells) on the hCAM after 8 days in the microfluidic system. The vertical dark gray lines are the ITO electrodes used to trap the cells on day 1. Arrowheads point to the projections of differentiated P19 cells. FIG. 16 shows immunostaining of neurofilaments, a marker of neuronal cells and therefore indicative of successful differentiation of the P19 cells, illustrates the projections from differentiated cells throughout the surface of the device. Cells on the ITO electrodes as well as cells that proliferate away from the electrode regions differentiated equally. Arrowheads point to the neurofilaments formed during cell differentiation. The scale bar in FIG. 15 is 50 µm.

In the subject matter described herein, an engineered cell adhesive surface was demonstrated with a two-fold purpose: the anchorage of cells under DEP conditions with continuous fluid flow field and its ability to support long term cell experiments such as cell induction and differentiation. A hybrid material comprising polyelectrolytes and FN, with FN and PAH at the surface satisfied this goal. The P19 cells were trapped with DEP forces and anchored on the hCAM surface in a continuous flow field within a microfluidic system. The cells were viable for up to 8 days and were able to undergo neuronal differentiation until cell fixation was carried out for immunostaining purposes. Additionally, the ability to induce P19 cells while the cells are adhered to a surface was demonstrated. This suggests that neurodevelopment studies that assess cell-cell interactions could be performed in microfluidic devices with hCAM surfaces. Going forward, microfluidics may allow the study of cell-by-cell mechanisms, including the pattern of morphogen response tracked by assessing the fraction of cells that have differentiated. This type of study may be possible by integrating DEP investigation systems with controlled microfluidic laminar flows.

Thus, in accordance with the present subject matter, a hybrid cell adhesive material, e.g., hCAM, includes an outermost layer of one or more polycation or polyelectrolyte materials disposed on a layer of fibronectin (FN) or other extra cellular matrix material. The hCAM layer captures cells or other bioparticles by attraction from dielectrophoretic forces, and retains the cells in place along an exposed surface of the hCAM layer. The hCAM layer uses the polycation material(s) to electrostatically bind the cells instantaneously which have a net negative charge along their surface, while concurrently the fibronectin or other extracellular matrix material promotes long term survival of the retained cells.

A wide array of polycation materials can be used in addition to, or instead of, poly(allylamine hydrochloride) (PAH) such as but not limited to poly(ethylene imine) (PEI), poly(diallyl-dimethyl ammonium) chloride (PDADMAC), poly(lysine), polyacrylamide (PAAm), similar agents, and combinations thereof.

A wide array of extracellular matrix materials can be used in addition to, or instead of, fibronectin such as laminin; elastin; collagen; collagen fibrils; proteoglycons such as heparan sulfate, chondroitin sulfate and the like; hyaluronic acid; and any other natural or synthetic material that will promote cell adhesion and can be assembled in layer-by-layer techniques referred to herein as an extracellular matrix material anologue. Combinations can also be used.

Preferably, the layers of the hCAM material, i.e. layer(s) of polycation material(s) and layer(s) of adhesion material(s) (i.e. extracellular matrix), are assembled in a layer-by-layer technique. The term "layer-by-layer" as used herein refers to a strategy by which layers of materials, usually polymers, are stacked one on top of each other by adsorption, and beginning on a substrate. Typically, electrostatic forces keep the layers adsorbed to the substrate initially and then to one another. However, other interactions have been shown to maintain or at least assist in maintaining the multilayers assembled as a single film or layer. Examples of these other interactions include covalent bonds, hydrogen bonding, donor-acceptor interactions, and the like. Generally, if the materials of the hCAM are merely mixed or otherwise combined, an undesirable precipitate typically forms.

The hCAM can utilize particular concentrations of agents in each of the layers. When using fibronectin as the extracellular matrix (adhesion) material, a preferred concentration is from about 25 to about 50 µg/ml, based upon the total amount of the FN-containing layer. When using PAH or other similar polycation material, a preferred concentration of the PAH or like material is typically about 1 mg/ml, based upon the total amount of the polycation layer.

The hCAM can optionally include one or more other agents, components, and/or materials for example polyions and lipids. Moreover, the present subject matter contemplates the potential use of particular combinations such as fibronectin/heparan sulfate, fibronectin/chondrotin sulfate, laminin/heparan sulfate, and laminin/chondroitin sulfate.

Additional nonlimiting examples of agents that could be included in the hCAM are growth factor peptides and proteins, small molecule drugs, i.e. which are slowly released during cell adhesion and growth, nano materials, antibodies (which influence cell response, fluorescent probes, i.e. for monitoring degradation of the extracellular matrix material, and combinations thereof. Typical concentrations of these agents in the hCAM are from about 5 µg/ml to about 100 µg/ml.

The total thickness of the hCAM after deposition depends upon the number of layers, and the distance of the cells to be trapped or retained on the hCAM layer from the substrate. Typically, at least one or more underlying layers are provided on the substrate and are disposed between the substrate and the hCAM. Typically, only one layer of the extracellular matrix material, e.g. fibronectin is needed. That layer should be close enough to the outer exposed surface of the hCAM to support cell survival and growth. Although not wishing to be bound to any particular theory, the thickness of the extracellular matrix material, e.g. fibronectin, is generally from about 2 nm to about 5 nm. The thickness of the polycation layer, after drying is typically about 2 nm for each layer. Thus, for an assembly of four (4) layers of polyions/fibronectin/PAH, the total thickness is generally about 12 nm to about 15 nm.

Polyester Membranes

In an embodiment, a system for dielectrophoretic cell capture includes cell capture on permeable polyester membranes. Photolithographic techniques were used to fabricate gold microelectrodes on a polyester membrane. The characterization of the microelectrodes showed that there were no differences regarding roughness, permeability, and hydrophilicity of the membrane before and after processing. Finally, dielectrophoretic cell capture and viability in a microfluidic device was demonstrated on the patterned membrane. These membranes could ultimately be combined with multilayer microfluidic devices to form a powerful tool for studies of cell-cell interactions in co-culture, whereby spatial separation of different cell types and/or microenvironments are required.

A multilayer microfluidic device with a polyester (PET) membrane has been used to separate the channels for cell culture and cell manipulation to monitor the induced gene expression of ZsGreen1-DR. The use of permeable PET membranes in multilayer microfluidic devices has several advantages. Soluble factors could diffuse through the intermediate membrane, and their effect on the cells could be observed without disturbing influences caused by their supply. Additionally, the double layered design adds another level of temporal and spatial control. The combination of a multilayer microsystem with dielectrophoretic cell capturing onto a permeable membrane will enable in vitro co-culture systems closer to cell-cell interactions that occur in vivo.

In accordance with the present subject matter, the fabrication, characterization, and use of a DEP microfluidic device comprised of electrically conductive, e.g. gold, microelectrodes on a permeable PET membrane is provided. Photolithographic procedures along with other techniques are used to evaporate and lift-off gold on PET membranes to obtain patterns of interdigitated electrodes. These electrodes were characterized using atomic force microscopy (AFM), scanning electron microscopy (SEM), and optical microscopy. The electrodes were tested for dielectrophoretic cell capture, and cell viability on the gold and PET membrane surfaces.

Figure 17:
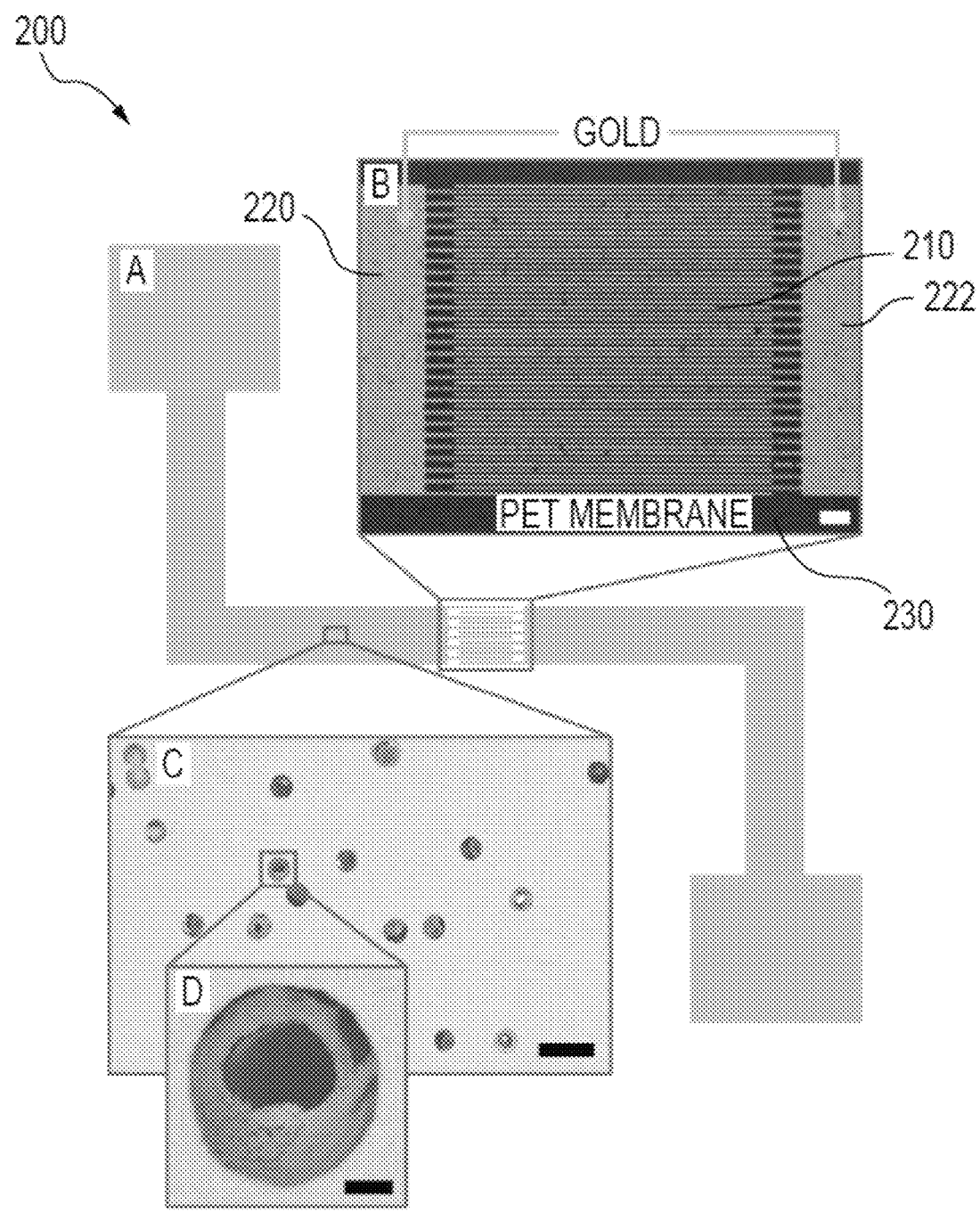
FIG. 17 shows a schematic illustration of a microfluidic device and several regions detailed, in accordance with the present subject matter.

Specifically, the present subject matter provides the fabrication of gold microelectrodes on a permeable PET membrane. The resulting DEP microelectrodes were characterized by several techniques. In FIG. 17, microfluidic system 200 in accordance with the present subject matter is shown. System 200 includes a plurality of gold electrodes 210. The interdigitated microelectrodes 210 shown in the center are linked to contact pads 220 and 222. FIG. 17, and specifically area B, shows an actual gold/PET surface. The continuous connection of the patterned gold is visible. The system 200 also comprises a PET membrane 230 upon which are disposed the electrodes 210 and pads 220, 222. The pores of the PET membrane 230 appear as black spots in the coated as well as uncoated areas of the surface. SEM images show the surface (area C in FIG. 17), and the insert (area D in FIG. 17). The extent of gold deposition, i.e. with regard to coverage or blockage of the micropores of the PET membrane, is best illustrated in area D of FIG. 17. SEM imaging showed dark grey spots inside the pores, i.e., the gold did not completely block them. The average distance to which the gold was deposited inside the pores was 2.1 µm±1.2 µm. These observations suggest that the pores remained open and therefore permeable. Even if the partial blockage would slightly affect the function of the membrane where gold was deposited, half of the cell adhesion surface area is not covered by it. Therefore, the permeability of the membrane remained effectively unaffected.

Specifically, FIG. 17 illustrates a scheme of the gold pattern and images of the gold patterned membrane. Area A shows a typical layout or configuration of the microfluidic system 200 having the microelectrodes in the center, which are connected to contact pads. Area B is a micrograph of the processed microelectrodes. Area C is an SEM image of the area used to measure the distance to which gold was deposited into the pores. The pores could be observed throughout the entire membrane. Area D is a detailed view of one pore showing its partial blockage by the deposited gold. The scale bar in area B is 100 µm, the scale bar in area C is 3 µm, and the scale bar in area D is 300 nm.

Figure 18:
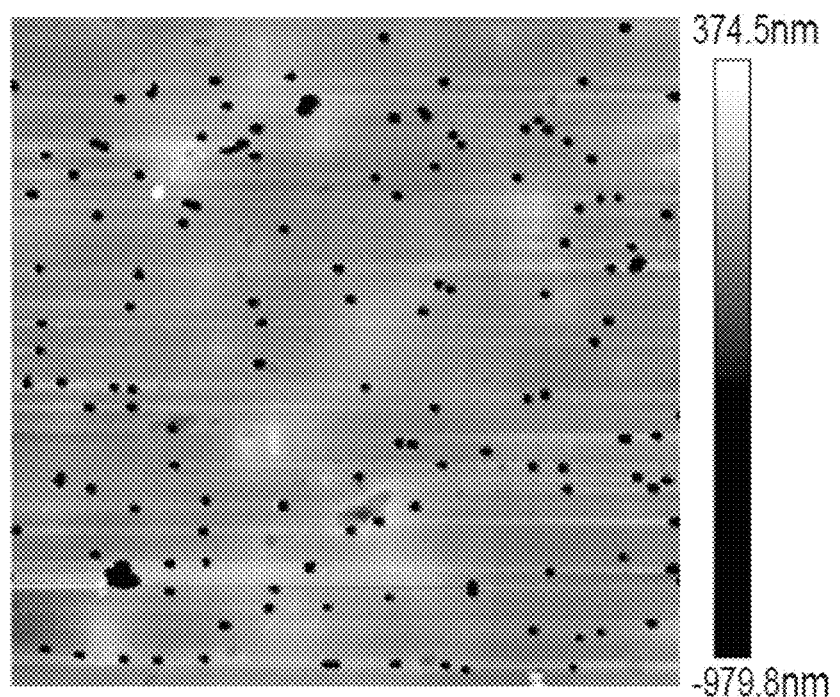
FIG. 18 shows an image of a PET membrane before processing.
Figure 19:
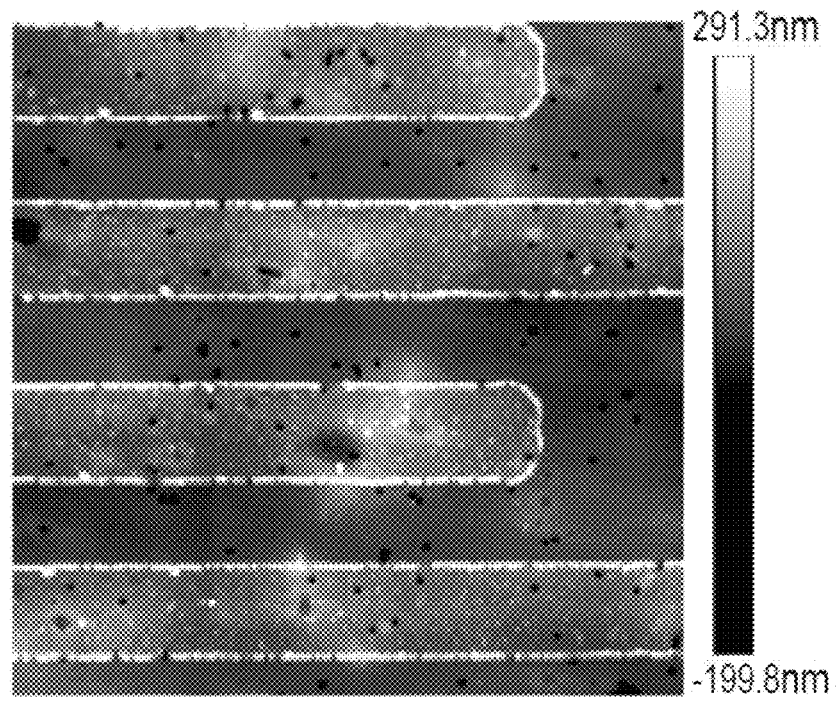
FIG. 19 shows an image of a PET membrane after processing.

FIG. 18 and FIG. 19 are AFM micrographs of a PET membrane before (FIG. 18) and after processing (FIG. 19) in accordance with the present subject matter. The pores could be observed throughout the membrane regardless of the patterned gold. The coated areas within the pattern were continuously connected to result in interdigitated microelectrodes. In addition, the surface roughness of the PET membrane was measured before and after treatment to assess any possible changes during processing. An RMS (root-mean-square) roughness of 28.7 nm±4.8 nm was observed for the membrane before processing, and an RMS roughness of 24.3 nm±10.6 nm was observed after treatment. When these results were analyzed they showed no statistical difference (ANOVA, analysis of variance, single factor, p=0.33). Even the RMS roughness on the gold pattern (27.1 nm±9.6 nm) was not statistically different from the before and after processing values mentioned above (p=0.70 and p=0.61, respectively). The mechanical stability of the membrane was visually evaluated after processing, whereby no changes were detected. Both figures show a surface area of 75 μm×75 μm. The pores are randomly distributed and have an average diameter of 1.2 μm. The pores can be easily observed throughout the PET membrane including where the continuous layer of gold had been deposited.

As described in Example 3 herein, contact angle measurements were used to monitor the hydrophilicity of the membrane during the processing steps (see Table 1 later herein). With a water contact angle of 86° the membrane was slightly hydrophilic before any treatment. The sequential microfabrication steps decreased the contact angle to 69°, whereby the biggest change occurred after fixing the PET membrane onto the glass wafer via PMMA.

Multilayer microfluidic device 300 (see FIG. 28 and FIG. 29) was assembled to test the permeability of the PET membrane after processing. Multilayer microfluidic device 300 includes glass substrate 310. Body 320 formed from a suitable polymeric material such as polydimethyl siloxane (PDMS) is disposed on substrate 310. Body 320 defines at least two flow channels such as bottom channel 330 and top channel 350. Device 300 additionally includes PET membrane 340 disposed between and generally separating flow channels 330 and 350. Two different food dyes were exchanged between the two layers by transporting them through the pores of the membrane (see FIG. 20, FIG. 21, FIG. 22, and FIG. 23). This ultimately confirmed that its permeability was restored. Details as to this investigation are provided in the description of Example 2 herein.

Specifically, FIG. 20, FIG. 21, FIG. 22, and FIG. 23 illustrate permeability testing of the PET membrane after processing. FIG. 20, FIG. 21, FIG. 22, and FIG. 23 show actual images of light and dark food dyes exchanged between the channels 330, 350 in the multilayer microfluidic device 300 by their transport through the pores of the PET membrane 340. Two flow channels 330, 350 were provided for the dyes. The light dye flowed from left to right and the dark dye from top to bottom. The lower regions of FIG. 20, FIG. 21, FIG. 22, and FIG. 23 show the corresponding flow patterns of the food dyes in the channels 330, 350. In FIG. 20, at t=0 both flow rates were 0.5 μl/min, resulting in a mixture at the intersection at membrane 340. In FIG. 21, after changing the flow rates (light: 10 μl/min, dark: 0 μl/min) the light dye was transported to the top channel 350 through the membrane 340 and filled the top channel 350 (approximately t=3 min). In FIG. 22, after inverting the flow rates the dark dye was transported to the bottom channel 330 and filled the channel (approximately t=7 min). And in FIG. 23, a combined mixture occurred after setting both flow rates back to 0.5 μl/min (approximately t=11 min). The scale bars in FIG. 20, FIG. 21, FIG. 22, and FIG. 23 are 100 μm.

Figure 24:
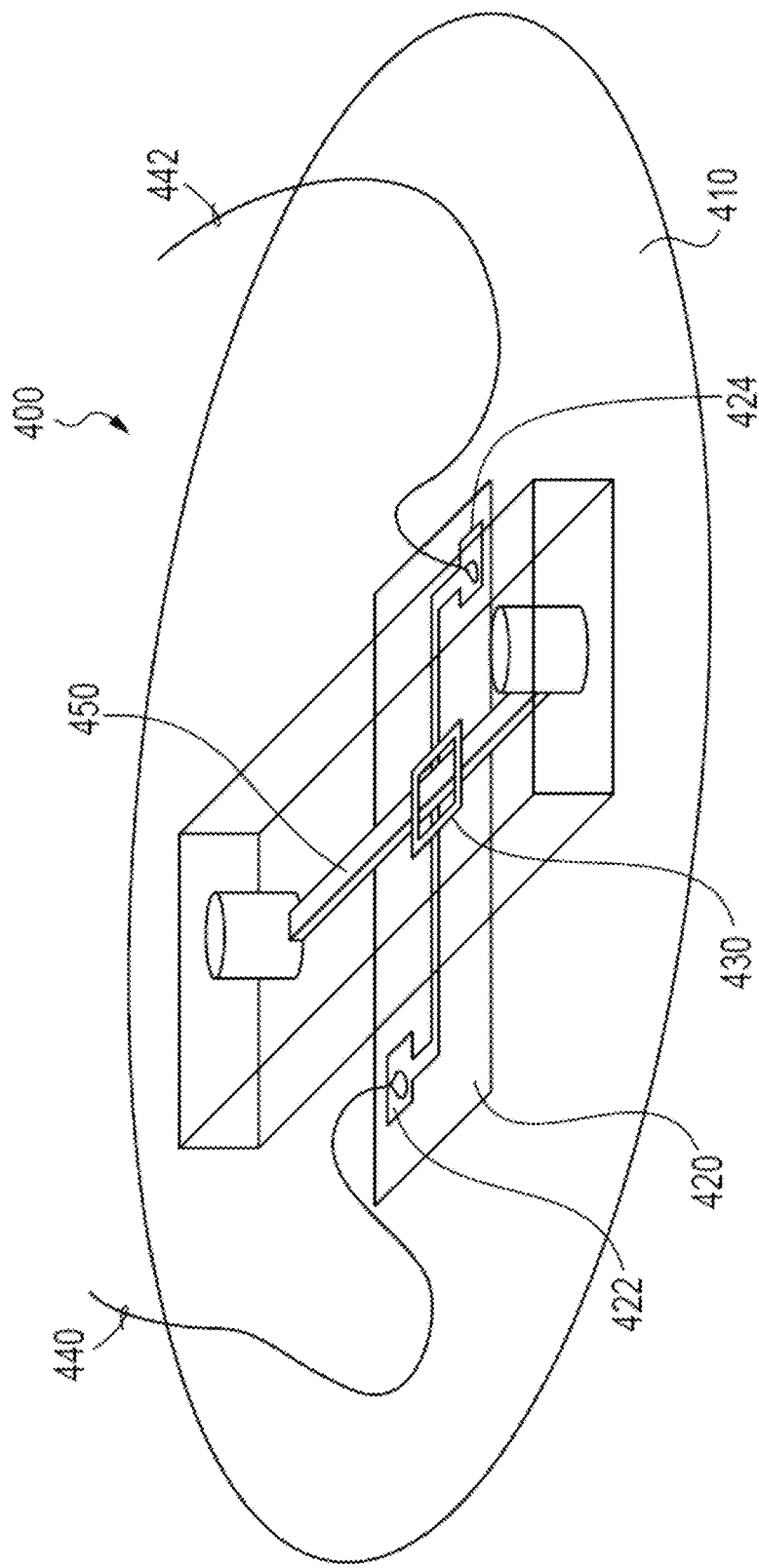
FIG. 24 shows a schematic illustration of another microfluidic device in accordance with the present subject matter.

The microelectrodes were evaluated for dielectrophoretic cell capture. In order to do this, a microfluidic device was assembled by placing a poly(dimethyl siloxane) (PDMS) microfluidic channel perpendicular to the microelectrodes. Specifically, referring to FIG. 24, a schematic illustration of the assembled microfluidic device is shown. A piece of PET membrane with deposited gold electrodes was fixed onto a glass wafer. The location of the microelectrodes is indicated by the square at the 430. The PDMS microfluidic channel was assembled on top, perpendicular to the microelectrodes. Wires were glued to the contact pads and connected to a waveform generator. Specifically, the microfluidic device 400 comprises a glass substrate 410, an assembly 420 of a PET membrane with electrically conductive electrodes, and at least one microfluidic channel 450 disposed on the assembly 420 of the membrane and electrodes. The assembly 420 includes contacts such as 422 and 424, at which a voltage source is connected such as through wires or other electrical conductors 440, 442.

For the cell trapping experiment NIH-3T3 cells were harvested in low-conductive media (to perform positive DEP) and inserted into the microchannel, prefilled with the same media. To avoid cell damage, the dielectrophoretic cell capture was carried out within 5 minutes after harvesting the cells. Trapped cells were collected in about half of the microelectrode surfaces by varying the applied voltage from 2 Vp-p to 5 Vp-p at a frequency of 10 MHz. Variations in the voltage allowed for cell capture across the length of the microelectrode array. When cells experienced higher electric fields they were trapped on the first few electrodes. On the other hand, when lower electric fields were applied cells tended to be trapped further down on the microelectrode array. The trapping efficiency could be increased further by either using a highly concentrated cell suspension or longer periods of DEP trapping. Additionally, the cell trapping efficiency can be influenced by the design of the microelectrodes. By modifying the configuration of the electrodes this could be further improved. Most of the trapped cells (approximately 90%) still remained on the PEMs after switching off the DEP forces and exchanging the low-conductive media with cell culture media. Cells attached well, as observed in FIG. 25. A live/dead assay was carried out 24 hours after cell attachment. The assay showed that about 99% of the cells emitted green fluorescence; i.e., these cells were alive, see FIG. 26.

Figure 26:
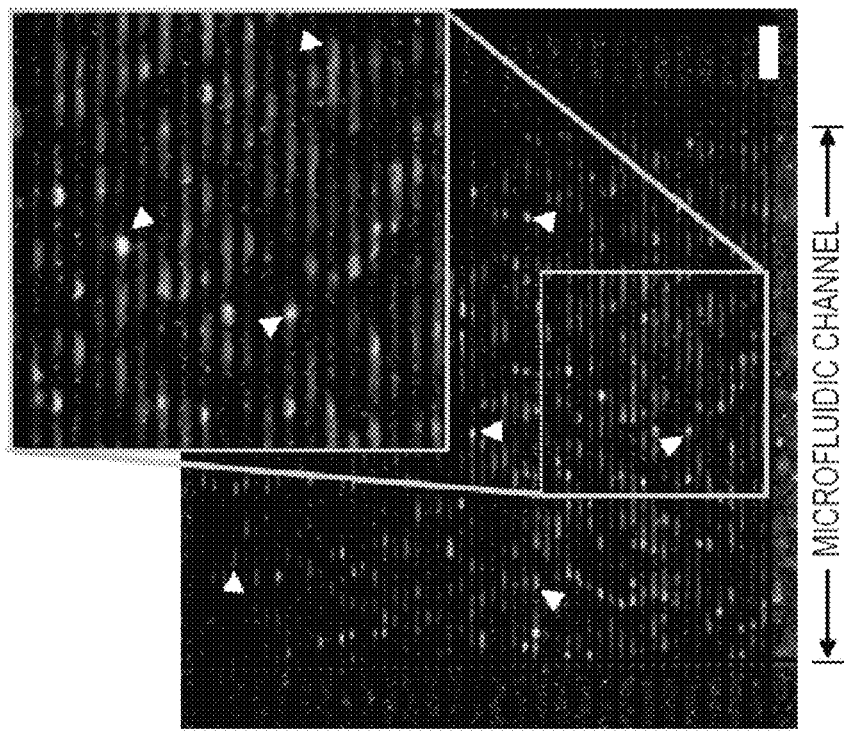
FIG. 26 shows an image of the trapped cells on the microelectrode surface 24 hours after trapping.
Figure 25:
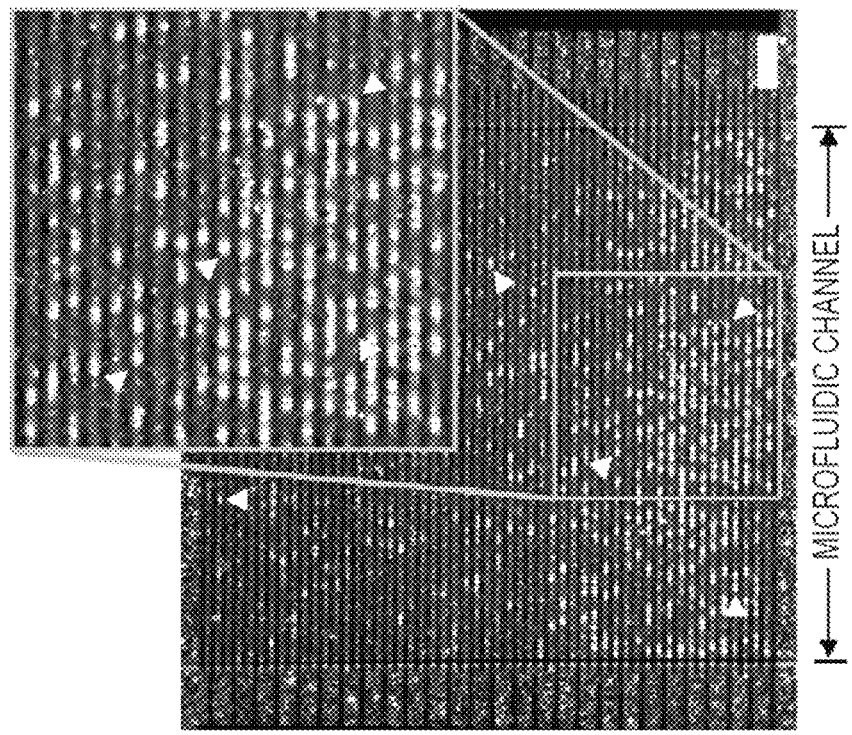
FIG. 25 shows an image of a collection of trapped cells on a micro electrode surface in a flow channel.

Specifically, FIG. 25 and FIG. 26 show efficient cell capture using DEP. FIG. 25 is a micrograph after switching off DEP forces and exchanging low-conductive media with cell culture media (0 h). NIH-3T3 cell capture was evident, as soon as 5 minutes from the time the microelectrodes were energized. Cells flowed from bottom to top of the figure during DEP trapping. Arrowheads point at some of the trapped cells. FIG. 26 shows a live/dead staining 24 hours after cell capture was carried out. The cells spread onto the membrane and green fluorescence could be observed in approximately 99% of the cells, demonstrating that cells were viable. The arrowheads in FIG. 26 point to some of the viable cells. Inserts show some of the trapped cells in more detail. The scale bars in FIG. 25 and FIG. 26 are 100 μm.

Figure 27:
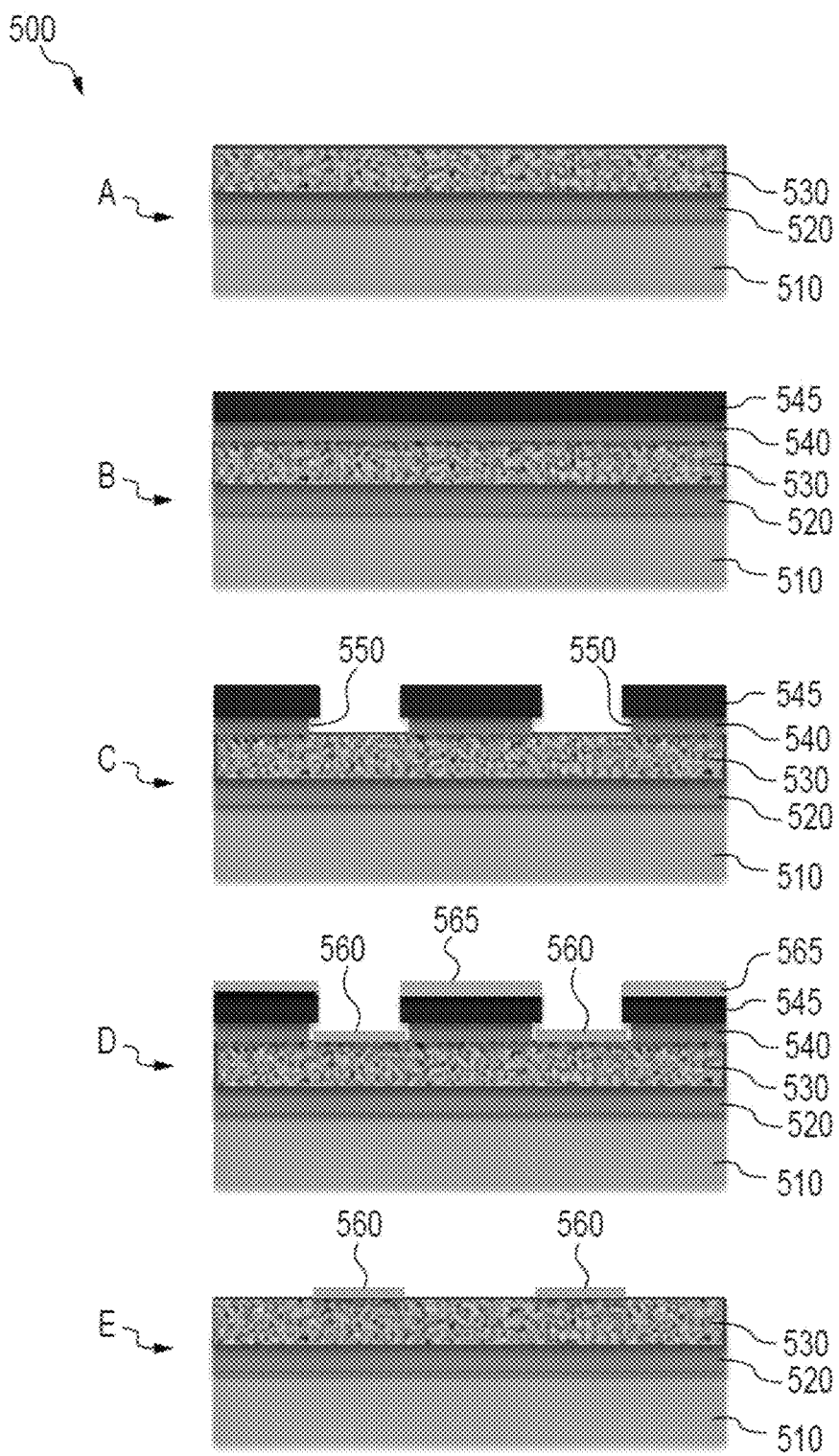
FIG. 27 shows a collection of images illustrating a method of forming electrically conductive regions on a PET membrane in accordance with the present subject matter.

FIG. 27 illustrates a method 500 of forming a plurality of gold electrodes on a PET membrane in accordance with the present subject matter. In stage A, a layer 520 of an adhesive such as PMMA is deposited onto a suitable substrate such as a glass wafer 510. Deposition of the adhesive can be performed by a wide array of techniques, such as spin coating. A polyester, e.g. PET, membrane 530 is applied onto a face of the adhesive layer 520. In stage B, two layers 540 and 545 of photoresist material(s) are applied such as by spin coating onto the PET membrane 530. In stage C, the photoresist face of the intermediate assembly from stage B is exposed to UV light to form stepped undercuts 550 between the two layers 540, 545 of the photoresist materials.

In stage D, thin layered regions 560, 565 of gold are deposited on the exposed upwardly directed surfaces of the intermediate assembly from stage C. Specifically, a collection of lower gold regions 560 and a collection of upper gold regions 565 form. It will be noted that a continuous layer of gold does not form between the lower and upper gold regions 560, 565 due to the stepped undercuts 550. In stage E, the photoresist bilayer, i.e. layers 540 and 545, and the upper gold regions 565 are removed to thereby leave the lower gold regions 560 on the PET membrane 530. Additional details related to the method 500, materials, and intermediate and resulting structure are provided in the description of Example 2 herein.

Figure 30:
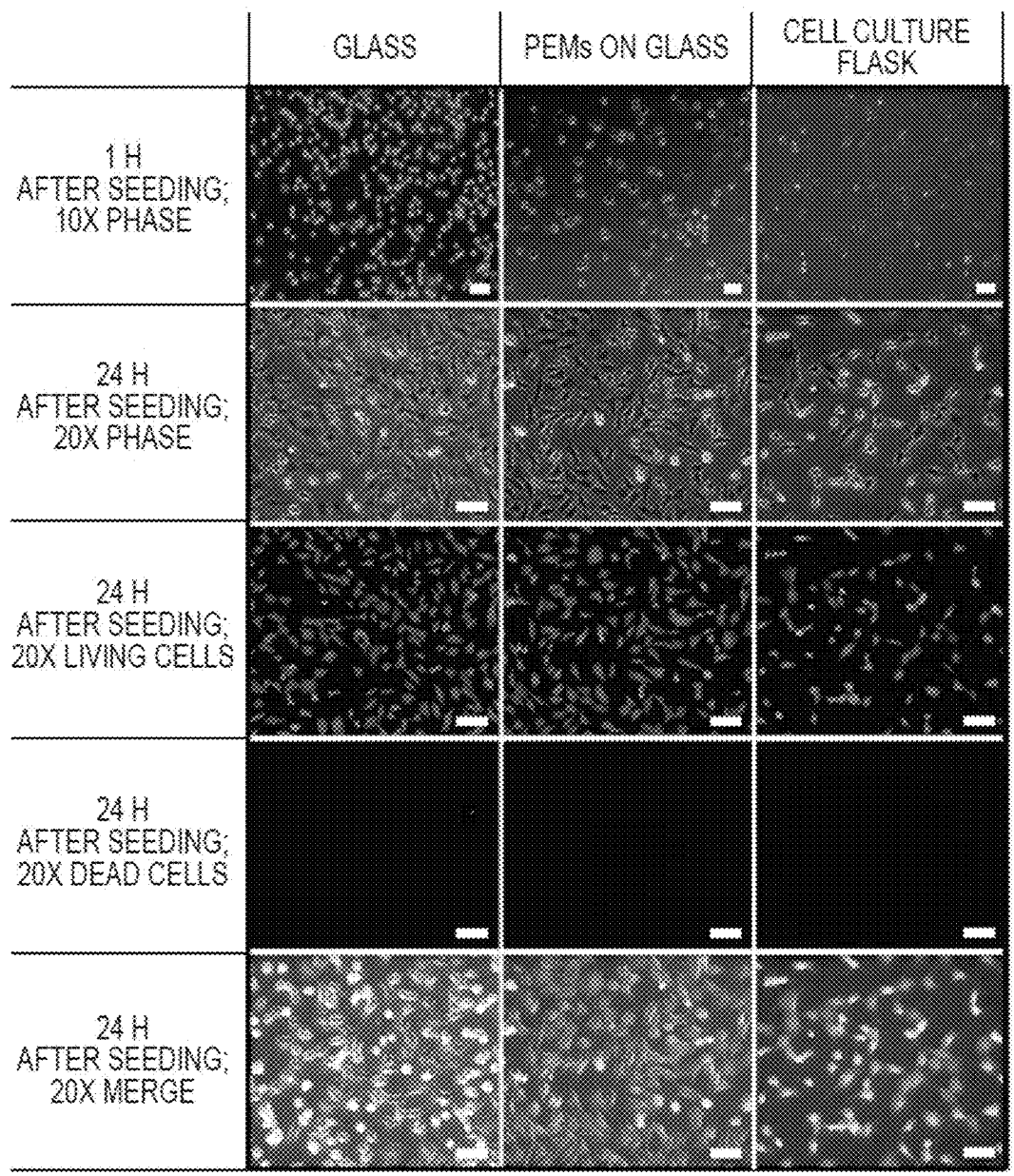
FIG. 30 shows a collection of images showing cell behavior on an array of different surfaces.

FIG. 30 is a collection of images illustrating cell behavior at various stages and on different surfaces. The details of this investigation are provided in the description of Example 3 herein.

DEP has been widely used in microfluidic platforms. The choice of platform will depend on the evaluations to be carried out. The type of bioparticle (e.g., cells and viruses) to be manipulated defines guidelines such as the design of the electrodes or performing experiments with or without flow. For example, hematopoietic tumor cells were analyzed using a DEP system without applied flow. The electrodes generated cell trapping forces and at the same time created electro-thermal vortices that produced efficient drug mixing, allowing for the analysis of cancer drug-induced cytotoxicity. A similar experiment was carried out where hepatitis A viruses were trapped in a microsystem using electro-hydrodynamic flow and DEP forces. These kinds of systems use non-adherent bioparticles and therefore provide platforms that can usually be reused several times. However, studies using adherent cells mostly require cell adhesive molecules on top of the electrodes to allow cell behavior and, hence, cell responses that would provide meaningful data. Since cells tend to rearrange the adhesive molecules they attach onto and leave behind residues from their own extracellular matrix after detaching, the number of times the devices can be reused is limited. When cells are used in a microfluidic platform it is beneficial to have some form of trapping mechanism. However, the use of, for example, mechanical traps creates areas with different flow velocities, hence influencing the flow near the cells. This could likely affect the results of experiments in the cases where cells are sensitive to such shear forces. In contrast, DEP systems with planar electrodes render a channel without features that disturb the flow.

The results demonstrate the functionality of the patterned microelectrodes on the permeable PET membrane for dielectrophoretic cell capture. This membrane along with DEP would be suited for specialized applications such as studies of drug transport, cell monolayer permeability and cell co-cultures, among others. However, these applications would gain the most when combined with multilayer microfluidic devices. The added levels of control and the benefit of the localized cell enrichment by DEP trapping are at the heart of these devices. In addition, the combination of DEP and PEMs on a permeable PET membrane allows fast and reliable cell capture at a high efficiency, and hence subsequent long term cell culture is achievable.

In the dual dielectrophoretic article 100, the membrane has electrodes disposed on its surface, wherein the electrodes (e.g., made of gold or other electrically conductive microelectrodes on PET membranes) perform DEP cell entrapment in the dual dielectrophoretic article 100 configured as a microfluidic device. The microelectrodes for DEP were fabricated using conventional photolithographic and metallization processes. The membrane was characterized with different techniques, and results showed that there was no difference in terms of hydrophilicity, roughness, and permeability of the membrane when comparing the before and after processing surfaces. Finally, it was demonstrated that the patterned electrodes can be used for DEP cell trapping experiments in a microfluidic channel. The cell viability assessment showed that cells were viable 24 hours after DEP trapping, demonstrating that long term cell experiments can be carried out. This approach allows for an easy and rapid way of cell entrapment and enrichment onto PET membrane surfaces. By combining this work with multilayer microfluidic devices a new platform for cell-cell interactions or cell co-culture studies could be developed. Cell exposure to different microenvironments would be possible, having two cell types physically separated.

In an embodiment, the membrane described in the preceding paragraphs is included in dual dielectrophoretic article 100. Advantageously and unexpectedly, dual dielectrophoretic article 100 is a multilayer microfluidic device, wherein a permeable membrane (e.g., with pores) separate opposing flow channels such that a size (e.g., in diameter) of pores disposed in the membrane can vary from less than 1 μm to up to tens of micrometers. The pores can be randomly or uniformly distributed in the membrane. Further, a plurality of electrodes can be disposed on the membrane, wherein the electrodes can be patterned on opposing surfaces (i.e., both sides of the membrane) and can include a metal or other conductive material. It is contemplated that the electrodes are used to electronically measure cell migration or invasion from one side of the membrane to the other. In certain embodiments, cell adhesive material is disposed on the membrane, wherein the cell adhesive material can include natural extracellular matrix (ECM) components in combination or independently as naturally occurring or synthetic material, e.g., polyelectrolytes such as polyallylamine hydrochloride. In an embodiment, cell adhesive materials are disposed on one side of the membrane (either top or bottom). In a particular embodiment, cell adhesive materials are disposed on both sides of the membrane. A thickness or composition of the cell adhesive materials can vary or can depend on a type (e.g., migration versus invasion) of assay in which dual dielectrophoretic article 100 performs.

Beneficially, dual dielectrophoretic article 100 provides determination quantitatively or in real-time of migration of cells from one side of the membrane to the other. Moreover, dual dielectrophoretic article 100 quantifies an amount of cells communicated across the membrane by acquiring and comparing impedance at both sides of the membrane. In some embodiments, cell communication through the pores of the membrane is accomplished by optical microscopy independently or in combination with electrical measurement of impedance at a surface of the membrane. In an environment, the membrane having electrodes disposed on both opposing surfaces is disposed on a substrate that includes flow channels to form a microfluidic structure as the dual dielectrophoretic article 100. In this configuration, dual dielectrophoretic article 100 provides a flow (e.g., stagnant or active) of fluid (e.g., a composition that includes cells, cell nutrients, saline, medicaments, and the like) to simulates physiological conditions in a selected environment (e.g., including the composition of cells, cell nutrients, saline, medicaments, and the like). Further, dual dielectrophoretic article 100 that includes microfluidic flows in the flow channels provide advantages due to microfluidics such as small sample size (e.g., microliter to peek a liter volumes)

and concomitant smaller waste volume of chemicals, better microenvironment control, and the like.

Figure 31:
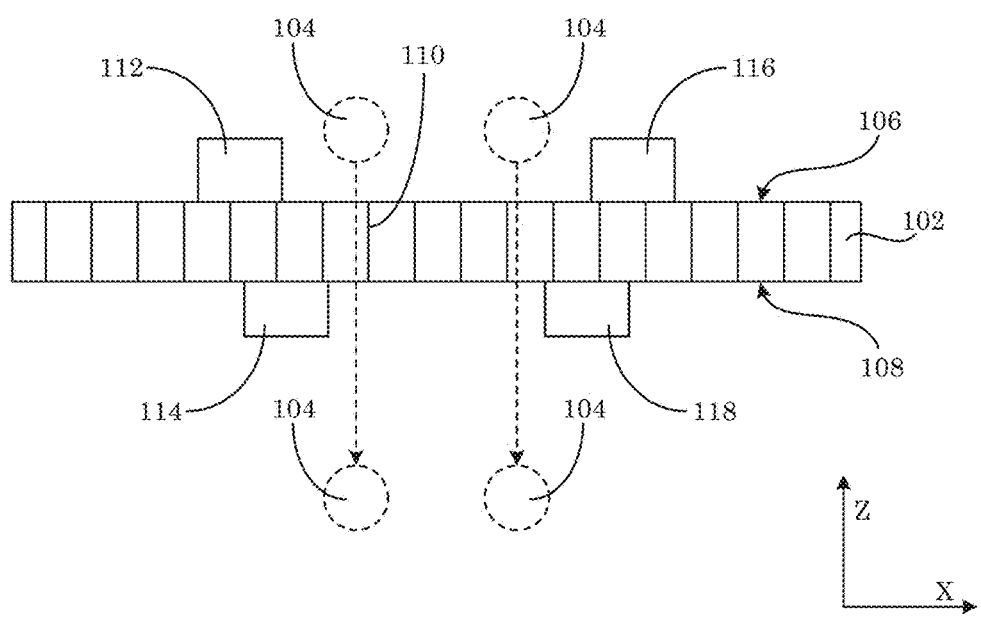
FIG. 31 shows a cross-section of a dual dielectropheretic article along line A-A of the dual dielectropheretic article shown in FIG. 32 and FIG. 33.
Figure 32:
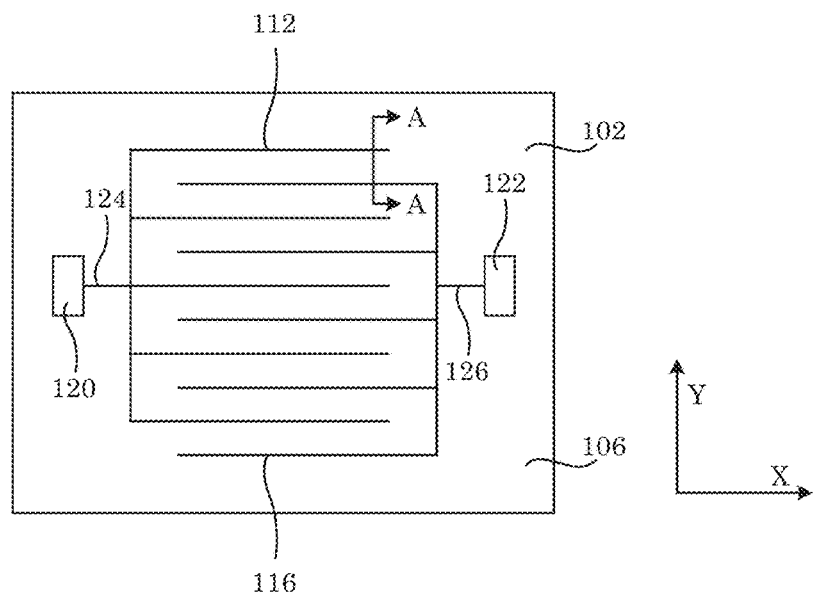
FIG. 32 shows a top view of the dual dielectropheretic article shown in FIG. 31.
Figure 33:
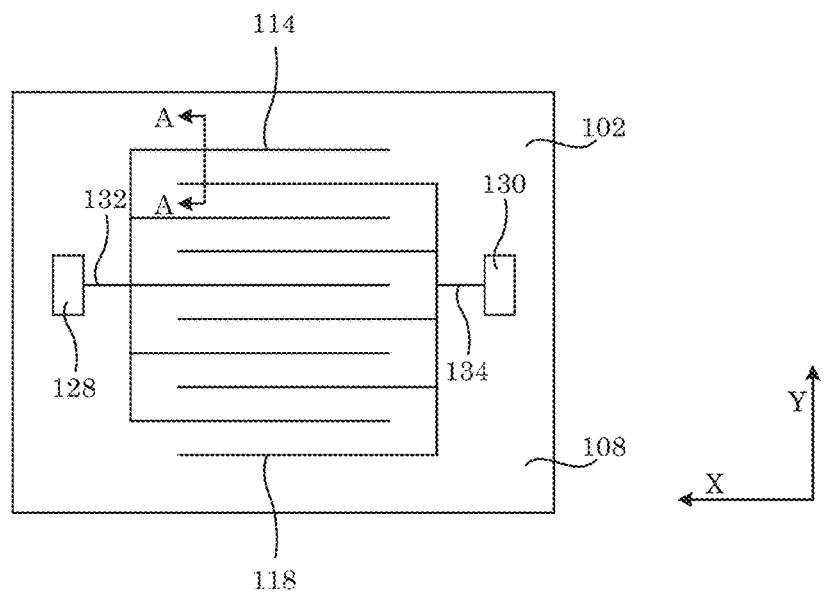
FIG. 33 shows a bottom view of the dual dielectropheretic article shown in FIG. 31.

In an embodiment, with reference to FIG. 31 (cross-section along line A-A in FIG. 32 (top view) FIG. 33 (bottom view), dual dielectropheretic article 100 for monitoring cell migration includes membrane 102 to selectively migrate a plurality of cells 104 across membrane 102. Membrane 102 includes first surface 106 to receive cells 104; second surface 108 opposed to first surface 106; and a plurality of communication paths 110 disposed in membrane 102 to provide the selective migration of cells 104 across membrane 102 from first surface 106 to second surface 108. First electrode 112 is disposed on first surface 106, and third electrode 114 disposed on second surface 108. First electrode 112 provides an electric field for dielectrophoresis of cells 104 at first surface 106 and also provides a first potential for monitoring an impedance at first surface 106. Third electrode 114 disposed on second surface 108 provides an electric field for dielectrophoresis of cells 104 at second surface 108 and also provides a third potential for monitoring an impedance at second surface 108. Additionally, dual dielectropheretic article 100, includes second electrode 116 disposed on first surface 106 and forth electrode 118 disposed on second surface 108 of membrane 102. Second electrode 116 provides the electric field, in combination with first electrode 112, for dielectrophoresis of cells 104 at first surface 106 and also provides a second potential for monitoring the impedance at first surface 106. Fourth electrode 118 disposed on second surface 108 provides the electric field, in combination with third electrode 114, for dielectrophoresis of cells 104 at second surface 108 and also provides a fourth potential for monitoring the impedance at second surface 108.

As shown in FIG. 32, first electrode 112 and second electrode 116 can be interdigitated. First electrode 112 can be in electrical communication via conductor 124 with contact pad 120. Contact pad 120 receives an electrical connection to connect first electrode 112, e.g., to an external power supply (e.g., to provide the first potential to first electrode 112) or an impedance analyzer. Similarly, second electrode 116 can be in electrical communication via conductor 126 with contact pad 122. Contact pad 122 receives an electrical connection to connect second electrode 116, e.g., to an external power supply (e.g., to provide the second potential to second electrode 116) or an impedance analyzer.

As shown in FIG. 33, third electrode 114 and forth electrode 118 can be interdigitated. Third electrode 114 can be in electrical communication via conductor 132 with contact pad 128. Contact pad 128 receives an electrical connection to connect third electrode 114, e.g., to an external power supply (e.g., to provide the third potential to third electrode 114) or an impedance analyzer. Similarly, force electrode 118 can be in electrical communication via conductor 134 with contact pad 130. Contact pad 130 receives an electrical connection to connect force electrode 118, e.g., to an external power supply (e.g., to provide the force potential to force electrode 118) or an impedance analyzer.

Figure 34:
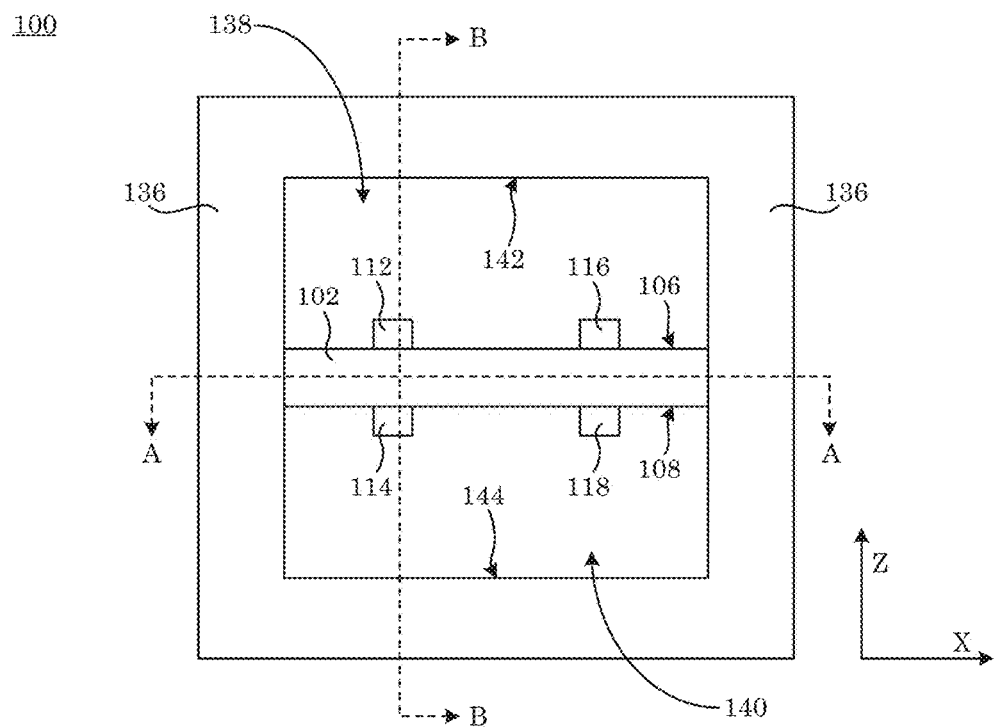
FIG. 34 shows a cross-section of a dual dielectropheretic article.
Figure 35:
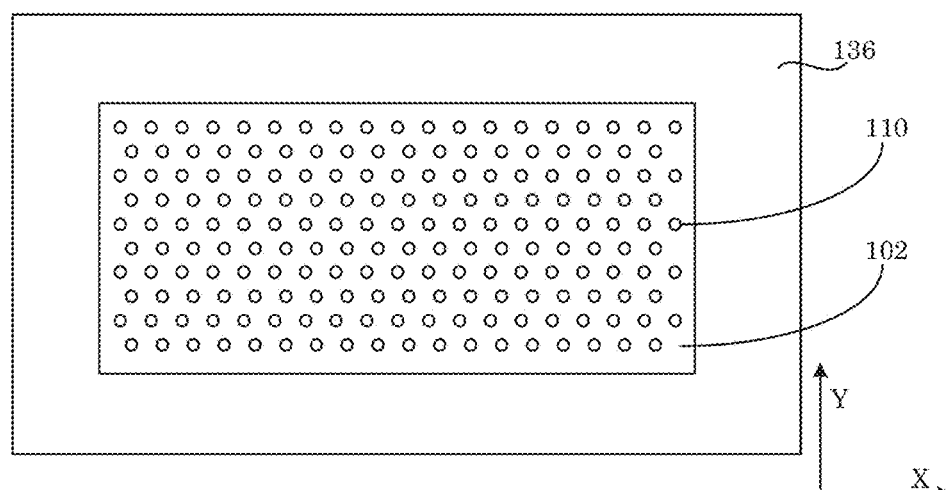
FIG. 35 shows a cross-section along line A-A of the dual dielectropheretic article shown in FIG. 34.
Figure 36:
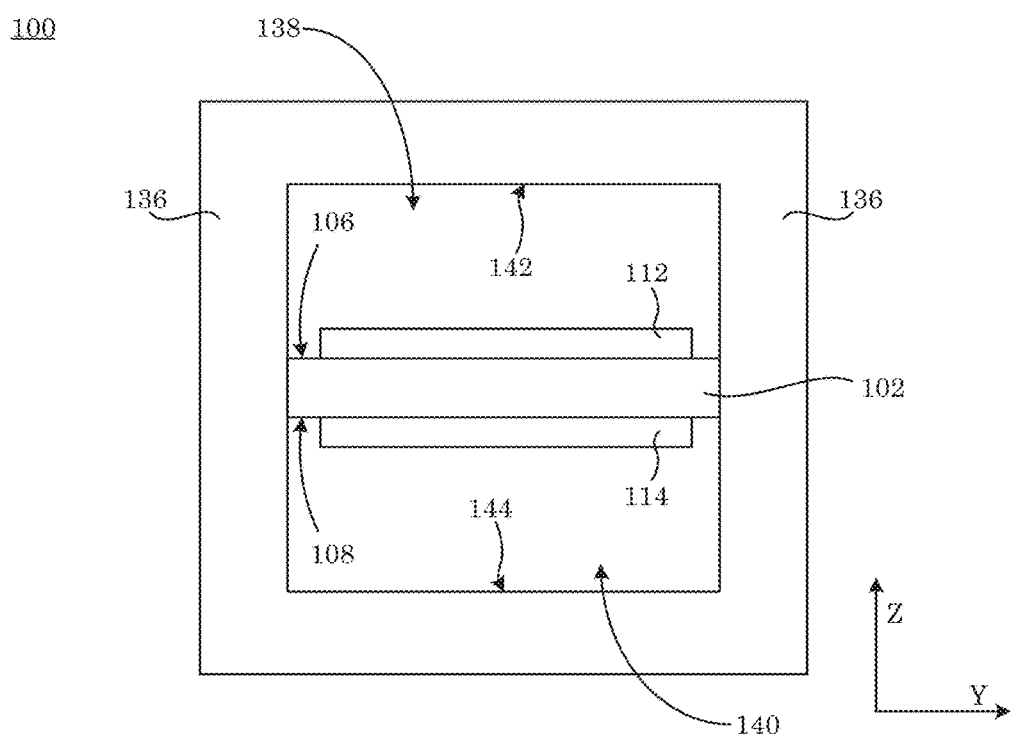
FIG. 36 shows a cross-section along line B-B of the dual dielectropheretic article shown in FIG. 34.

In an embodiment, with reference to FIG. 34 (a longitudinal cross-sectional view), FIG. 35 (cross-section along line A-A shown in FIG. 34), and FIG. 36 (cross-section along line B-B shown in FIG. 34), dual dielectropheretic article 100 includes membrane 102 disposed on substrate 136. First flow channel 138 is disposed in substrate 136 and is in fluid communication with first surface 106 to provide cells 104 to first surface 106 for dielectrophoresis of cells 104 at first surface 106 and selective migration through membrane 102 from first surface 106 to second surface 108. Here, a flow of cell 104 in first flow channel 138 is orthogonal to the x-z coordinates shown in FIG. 34. Moreover, first flow channel 138 is bounded by wall 142 and first surface 106. Entry and exit ports (not shown) for fluid flow through first flow channel 138 are in fluid communication with first flow channel 138 through substrate 136.

Second flow channel 140 is bounded by wall 144 and second surface 108 such that second flow channel 140 disposed in substrate 136 and is in fluid communication with second surface 108. In this manner, second flow channel 140 receives cells 104 from second surface 108 after selective migration of cells 104 to second surface 108 from first surface 106 via communication of cells 104 through communication paths 110 disposed in membrane 102. As shown in FIG. 35, communication paths 110 can be a plurality of pores distributed in membrane 102 to render membrane 102 permeable to cells 104, chemical compounds, bioparticles, and the like. Entry and exit ports (not shown) for fluid flow through second flow channel 140 are in fluid communication with second flow channel 138 through substrate 136.

Figure 37:
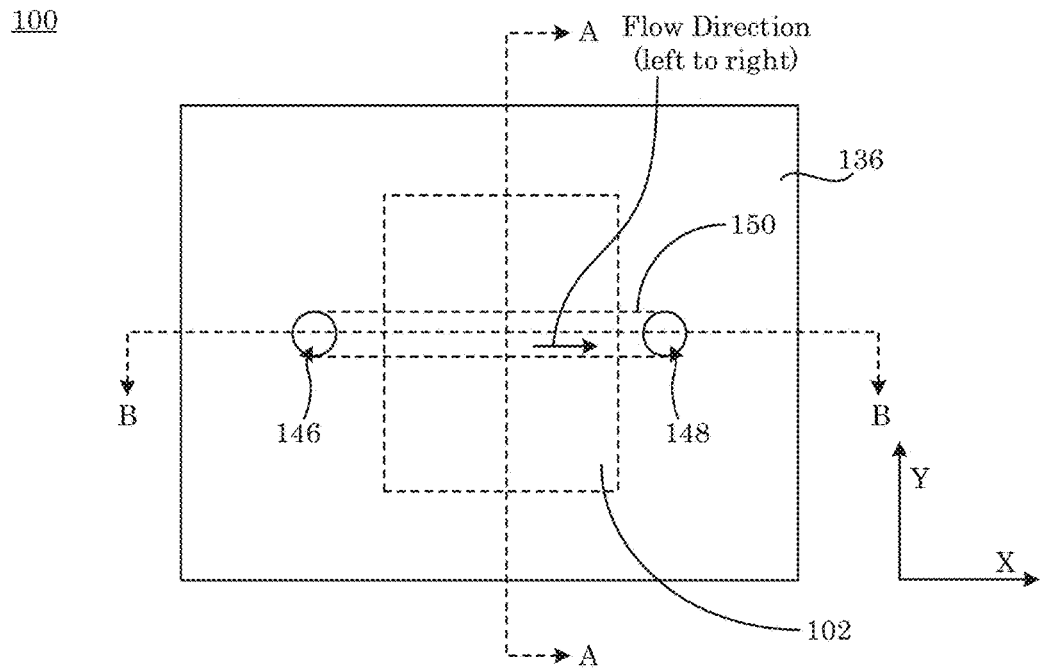
FIG. 37 shows a top view of a dual dielectropheretic article.
Figure 38:
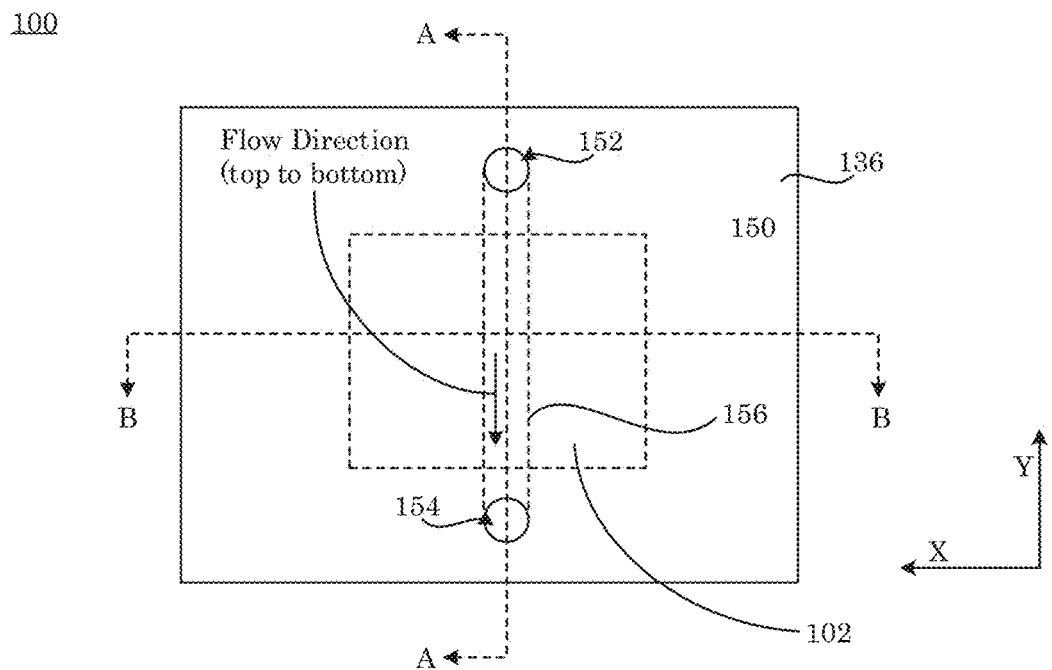
FIG. 38 shows a bottom view of the dual dielectropheretic article shown in FIG. 37.
Figure 39:
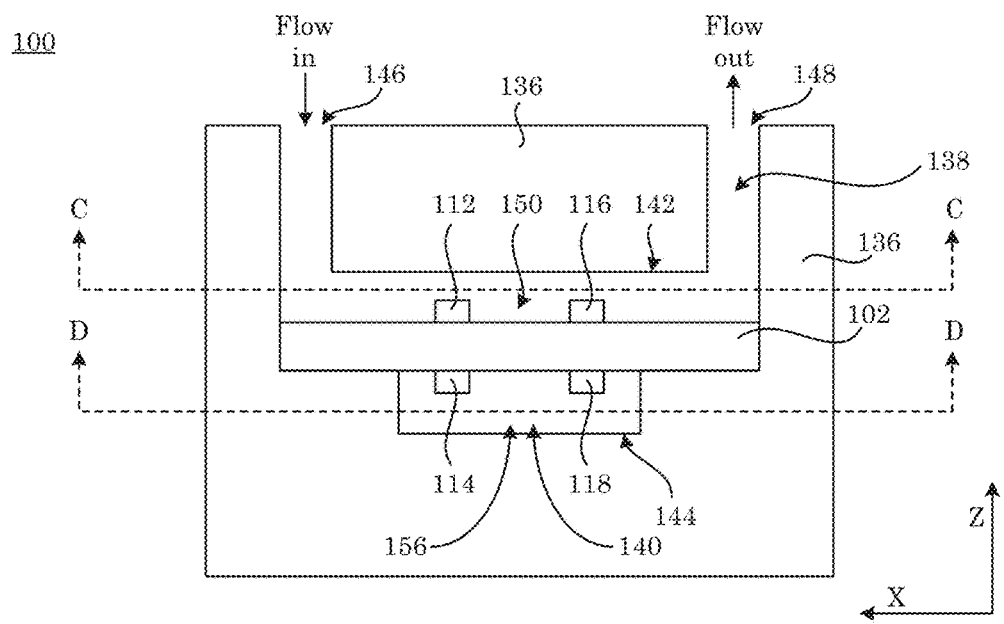
FIG. 39 shows a cross-section along line A-A of the dual dielectropheretic article shown in FIG. 37.
Figure 40:
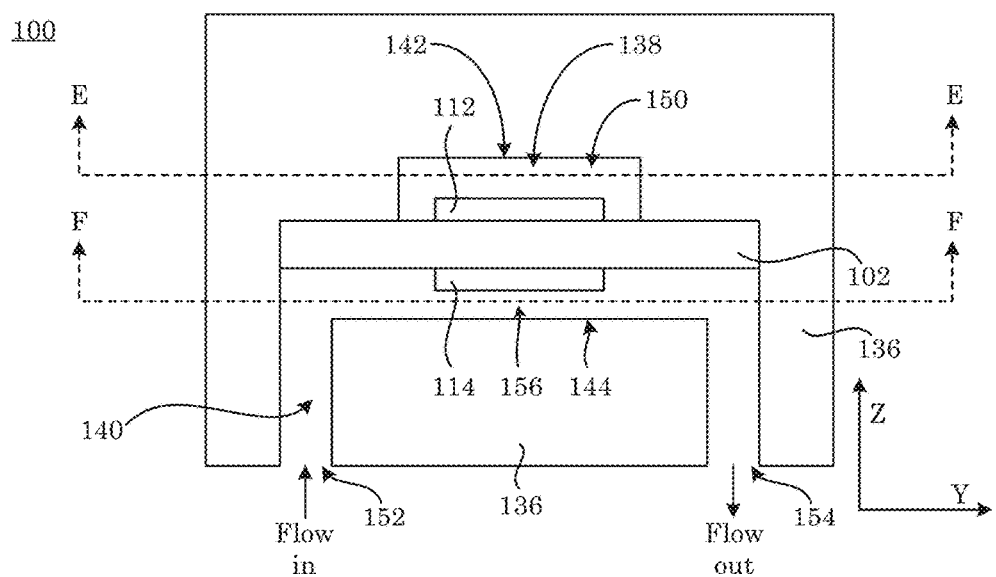
FIG. 40 shows a cross-section along line B-B of the dual dielectropheretic article shown in FIG. 37.
Figure 41:
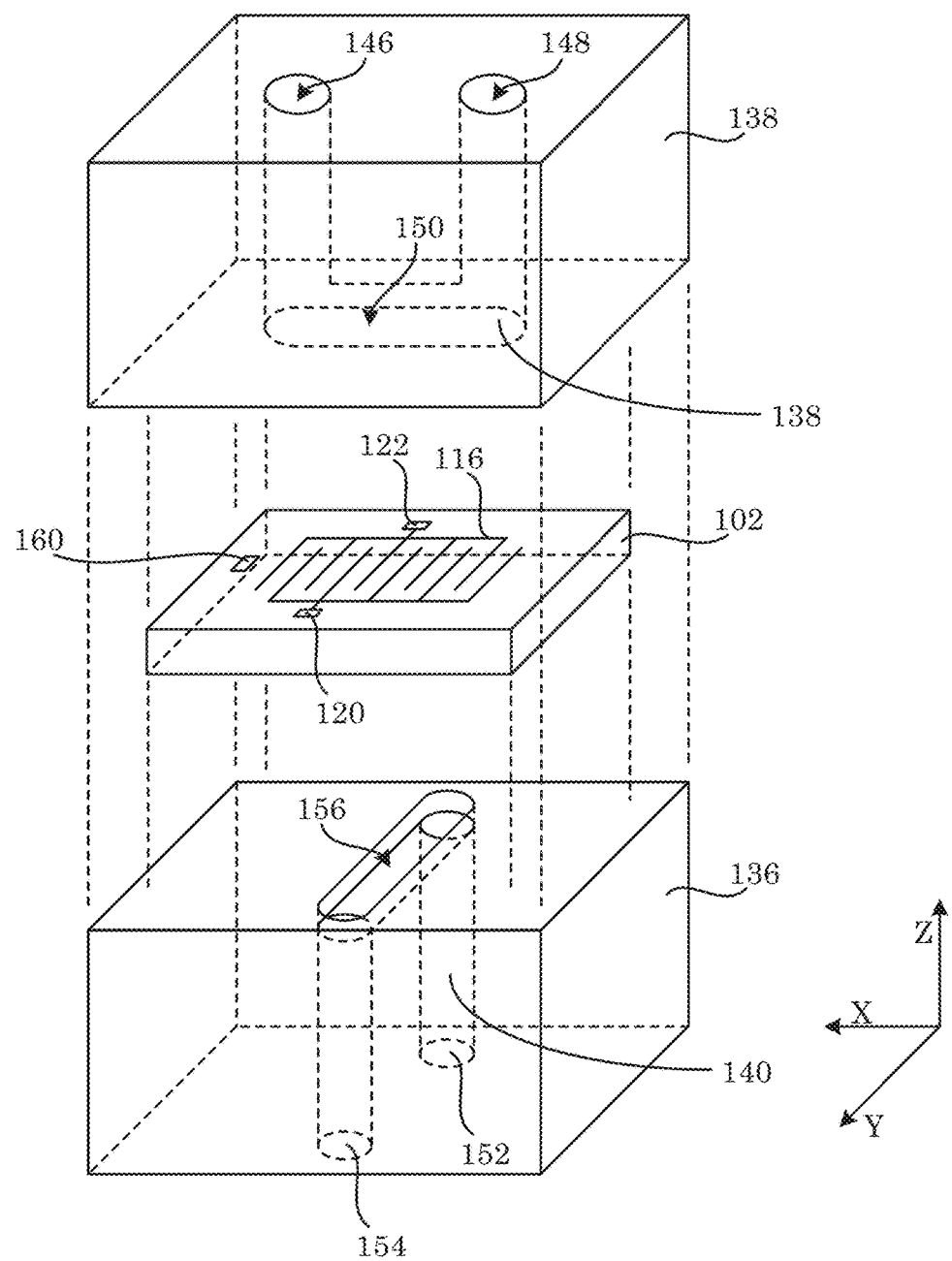
FIG. 41 shows an exploded perspective view of the dual dielectropheretic article shown in FIG. 37.

In an embodiment, dual dielectropheretic article 100 includes membrane 102 disposed on substrate 136 as shown in FIG. 37 (top view), FIG. 38 (bottom view), FIG. 39 (cross-section along line A-A shown in FIG. 37), FIG. 40 (cross-section along line B-B shown in FIG. 37), FIG. 41 (exploded perspective view), FIG. 42 (cross-section along line C-C shown in FIG. 39), FIG. 43 (cross-section along line D-D shown in FIG. 39), FIG. 44 (cross-section along line E-E shown in FIG. 40), and FIG. 45 (cross-section along line F-F shown in FIG. 40), which illustrate fluid communication in first flow channel 138 and second flow channel 140. Here, first flow channel 138 includes entry port 146 to receive a fluid that includes, e.g., cells 140 or other components; conduit 150 in fluid communication with entry port 146 and proximate to first electrode 112 and second electrode 116; and exit port 148 in fluid communication with entry port 146 via conduit 150. In this manner, the fluid can flow from entry port 146 through conduit 150 and exit first flow channel 138 at exit port 148 such that the fluid can contact or be proximate to first electrode 112 and second electrode 116. Similarly, second flow channel 140 includes entry port 152 to receive a fluid that includes, e.g., cells 140 or other components; conduit 156 in fluid communication with entry port 152 and proximate to third electrode 114 and forth electrode 118; and exit port 154 in fluid communication with entry port 152 via conduit 156. In this manner, the fluid can flow from entry port 152 through conduit 156 and exit second flow channel 140 at exit port 154 such that the fluid can contact or be proximate to third electrode 114 and forth electrode 118. In a particular embodiment, a first fluid including come e.g., cells 140, is disposed in first flow channel 138 by introducing fluid flow of the first fluid in entry port 146 and into conduit 150 so that cells 140 are proximate to first electrode 112 and second electrode 116 such that the cells are subjected to an electric field produced by first electrode 112 and second electrode and 116. In response to cells 140 being in presence of the electric field, cells 140 are subjected to dielectrophoretic trapping at first surface 106 of membrane 102 between first electrode 112 and 116. Trapped cells 140 are communicated through communication path 110 disposed in substrate 102, wherein cells 140 are communicated from first surface 106 to second surface 108 of membrane 102 such that cells 140 are present at second surface 108 and can be in contact with a second fluid introduced into second flow channel 140 from entry port 152 with flow into conduit 156 and out of second flow channel 140 via exit port 154. In this manner, cells 140 at second surface 108 of membrane 102 can be communicated away from second surface 108 and exit second flow channel 140 at exit port 154.

Figure 42:
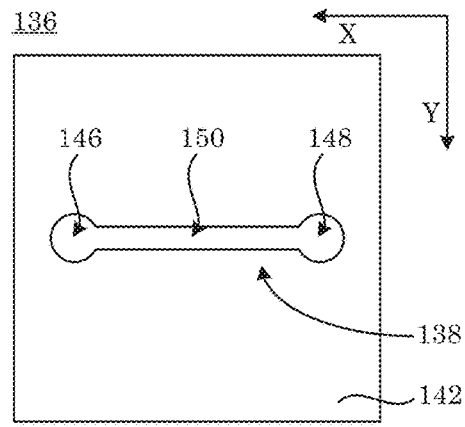
FIG. 42 shows a first flow channel disposed in the substrate along line C-C of the dual dielectropheretic article shown in FIG. 39.
Figure 43:
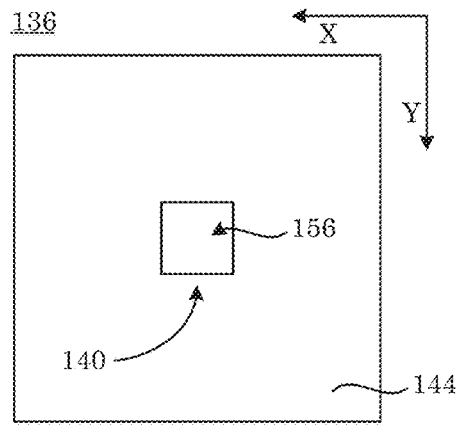
FIG. 43 shows a second flow channel disposed in the substrate along line D-D of the dual dielectropheretic article shown in FIG. 39.
Figure 44:
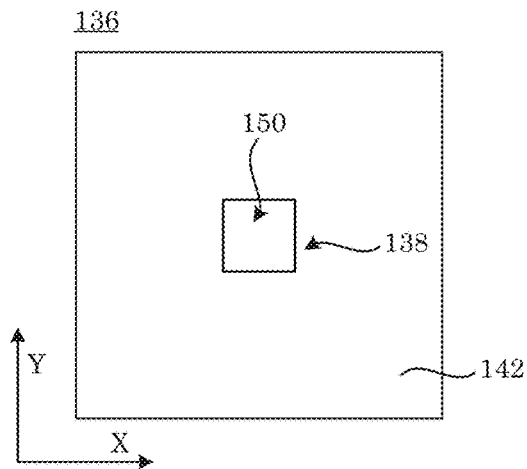
FIG. 44 shows the first flow channel disposed in the substrate along line E-E of the dual dielectropheretic article shown in FIG. 40.
Figure 45:
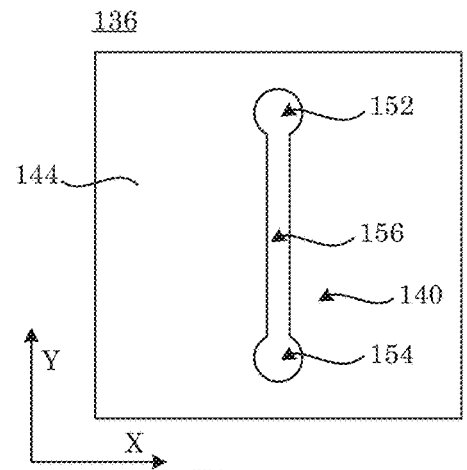
FIG. 45 shows the second flow channel disposed in the substrate along line F-F of the dual dielectropheretic article shown in FIG. 40.

As shown in FIG. 42 and FIG. 44, which are cross-sectional views along line C-C and line E-E respectively shown in FIG. 39 and FIG. 40, first flow channel 138 is disposed in substrate 136 and recessed with respect to wall 142 and first surface 106 of membrane 102. As shown in FIG. 43 and FIG. 45, which are cross-sectional views along line D-D and line F-F respectively shown in FIG. 39 and FIG. 40, second flow channel 140 is disposed in substrate 136 and recessed with respect to wall 144 and second surface 108 of membrane 102. In this configuration, conduit 50 of first flow channel 138 extends perpendicular to conduit 156 of second flow channel 140 in substrate 136 in dual dielectropheretic article 100 such that flow of the first fluid in first flow channel 138 is orthogonal to flow of the second fluid in second flow channel 140. In some embodiment, flow of the first fluid in first flow channel 138 can be in a same direction as flow of the second fluid in second flow channel 140 such that flow can occur either in the same direction, counter-propagating, or at any angle therebetween, depending on the relative alignment of conduit 150 and conduit 156 and a direction of flow the first fluid in conduit 150 and second fluid conduit 156.

Figure 46:
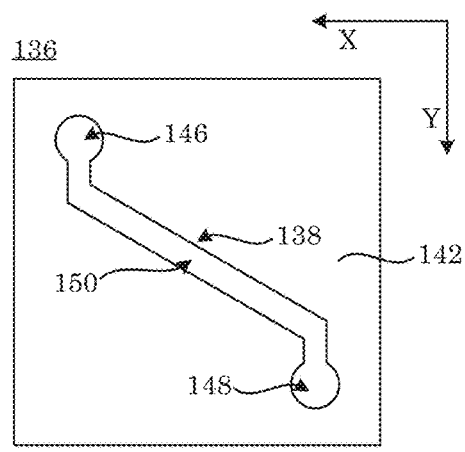
FIG. 46 shows a first flow channel disposed in a substrate similar to the view shown in FIG. 42.
Figure 47:
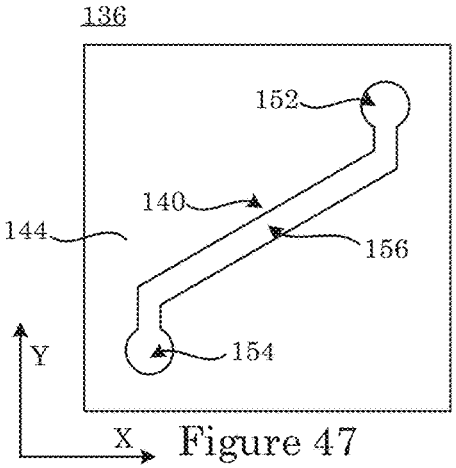
FIG. 47 shows a second flow channel disposed in a substrate similar to the view shown in FIG. 43.

In an embodiment, with reference to FIG. 46 and FIG. 47, a pattern of first flow channel 138 and second flow channel 140 is selected to communicate first fluid and second fluid respectively through conduit 150 of first flow channel 138 and conduit 156 second flow channel 140 on opposing sides of membrane 102. Here, ports (146, 148, 152, 154) are offset from a direction of elongation of conduits (150, 156) of flow channels (138, 140).

Substrate 136 is selected to receive and support membrane 102 as well as provide flow channels (138, 140) for disposal of fluid (e.g., first fluid and second fluid) that contains, e.g., cells 140, bioparticles, and the like proximate to electrodes (112, 114, 116, 118) disposed on membrane 102. Substrate 136 can include a metal, polymer, glass, ceramic, semiconductor, and the like. When the substrate is electrically conductive, substrate 136 is electrically isolated from electrodes (112, 114, 116, 118) by an electrically insulating material. Exemplary substrates 136 include, e.g., silicones, glass, and polymeric substrates such as polystyrene, poly(methyl methacrylate), polycarbonate, TOPAS (cyclo-olefin copolymer, COC), Zeonor, (cyclo-olefin polymer, COP) and Zeonex (cyclo-olefin polymer, COP).

A shape or size of substrate 136 can be any shape or size to provide flow channels (138, 140) for disposal of fluid (e.g., first fluid and second fluid) that contains, e.g., cells 140, bioparticles, and the like proximate to electrodes (112, 114, 116, 118) disposed on membrane 102. Exemplary shapes of substrate 136 include rectangular and circular. Exemplary sizes (e.g., a longest dimension) of substrate 136 can be from 1 mm to 100 mm.

Flow channels (138, 140) can be formed in substrate 136 by photolithography, soft lithography, injection molding, additive manufacturing, and the like. A shape or size of flow channels (138, 140) can be any shape or size to provide flow for disposal of fluid (e.g., first fluid and second fluid) that contains, e.g., cells 140, bioparticles, and the like proximate to electrodes (112, 114, 116, 118) disposed on membrane 102. Exemplary shapes of flow channels (138, 140) include rectangular or hemi-spherical. Exemplary sizes (e.g., a diameter or width dimension) of flow channels (138, 140) can be from 40 µm to 2 mm. Exemplary height dimensions of flow channels (138, 140) can be from 40 µm to 100 µm. Exemplary length of conduits (150, 156) can be from 5 mm to 100 mm.

Figure 48:
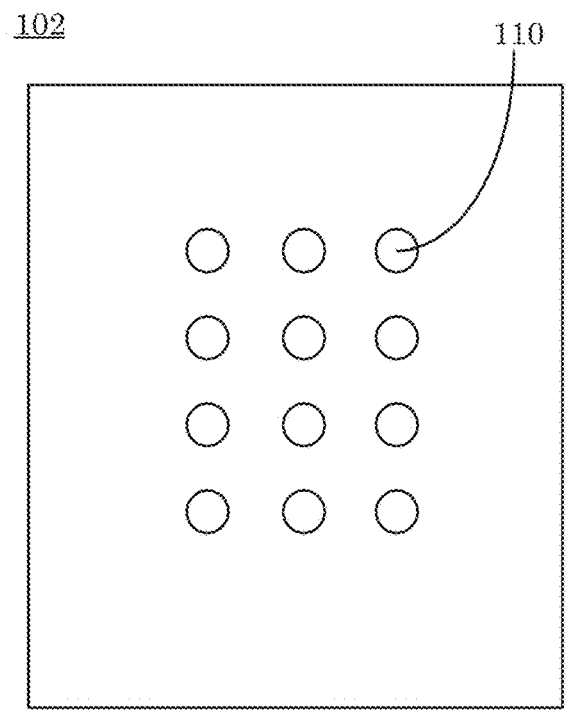
FIG. 48 shows a top view of a membrane having pores arranged in a uniform distribution in the membrane.
Figure 49:
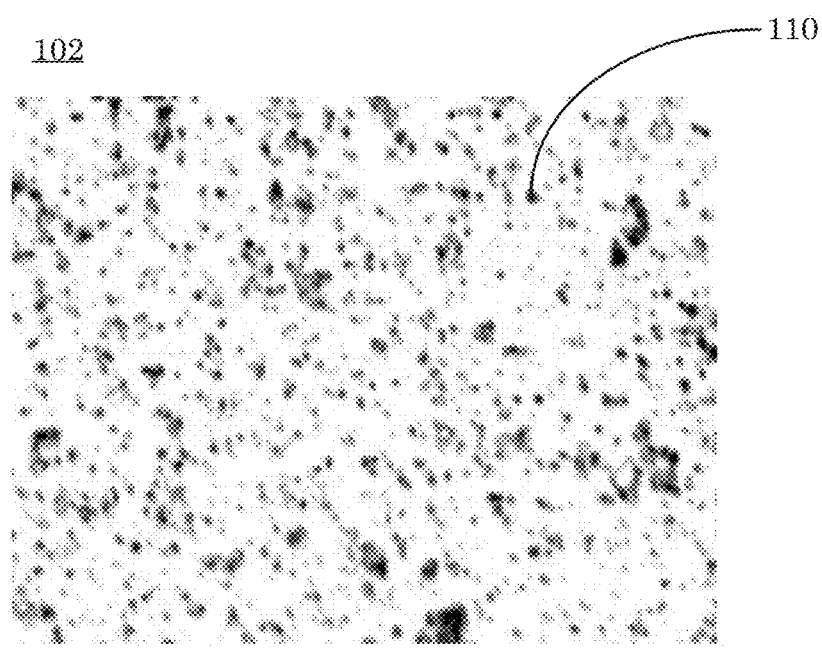
FIG. 49 shows a top view of a membrane having pores arranged in a random distribution in the membrane.

Membrane 102 is disposed on substrate 136. Membrane 102 can be disposed on substrate by mechanical deposition, mechanical transfer, solvent-assisted flattening, and the like. In an embodiment, membrane 102 is membrane 340 as above-described. According to an embodiment, membrane 102 includes PET and communication paths 110 as pores in the PET. The pores are open pores and can have a diameter from 1 µm to 100 µm to provide selective migration of cells across membrane 102 from first surface 106 to second surface 108. In a certain embodiment, the open pores are disposed in an ordered arrangement in membrane 102 as shown in FIG. 48. In a particular embodiment, the open pores are disposed in a random arrangement in the membrane as shown in FIG. 49.

According to an embodiment, membrane 102 includes a cell adhesive material disposed on first surface 106, second surface 108, or a combination of first surface 106 and second surface 108. The cell adhesive material adheres cells 104 to first surface 106, second surface 108, or the combination of first surface 106 and second surface 108 on which the cell adhesive material is disposed. The cell adhesive material can include an extracellular matrix component, a polyelectrolyte, or a combination comprising at least one of the foregoing cell adhesive materials. Exemplary extracellular matrix components include cellulose, collagen, fibronectin, laminin and the like. Exemplary polyelectrolytes include poly(sodium styrene sulfonate), poly(acrylic acid), polylysine, polyarginine, poly(allylamine hydrochloride), and the like. In an embodiment, for an invasion assay by cells 104, the cell adhesive material can be thicker at first surface 106 of membrane 102 than a thickness on second surface 108. The cell adhesive material can be a gel-like material. Cell adhesive material disposed on second surface 108 of membrane 102 can be the same as that disposed on first surface 106. It is contemplated that cell adhesive material renders cells 104 viable and allows cells 104 to spread on surfaces (106, 108) of membrane 102.

In an embodiment, for an assay of cell migration of cells 104, cell adhesive material disposed on first surface 106 of membrane 102 adheres cells 104 on membrane 102 and maintains cells 104 in place under constant flow of first fluid and after dielectrophoretic forces (e.g., electric field) are terminated from first electrode pair 101 (e.g., electrodes 112, 116) on membrane 102. An example of such adhesive material is the hybrid cell adhesive material above-described. Second surface 108 of membrane 100 to can be covered cell adhesive material identical or similar to the cell adhesive material disposed on first surface 106 or can be different than the cell adhesive material disposed on first surface 106, wherein the cell adhesive material disposed on second surface 108 renders cells 104 viable.

Figure 51:
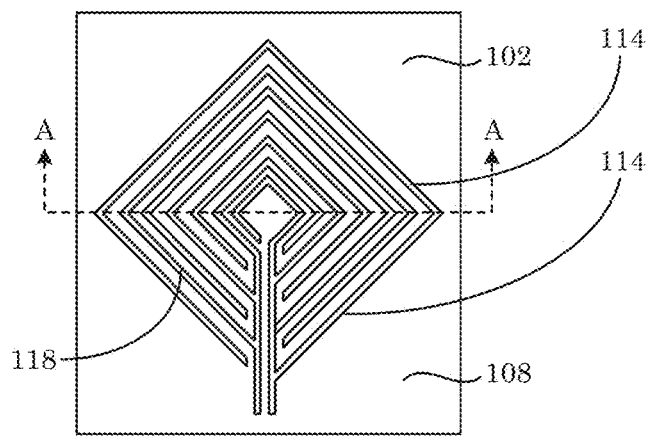
FIG. 51 shows electrodes disposed on a surface of a membrane and arranged in a pattern of concentric squares.
Figure 52:
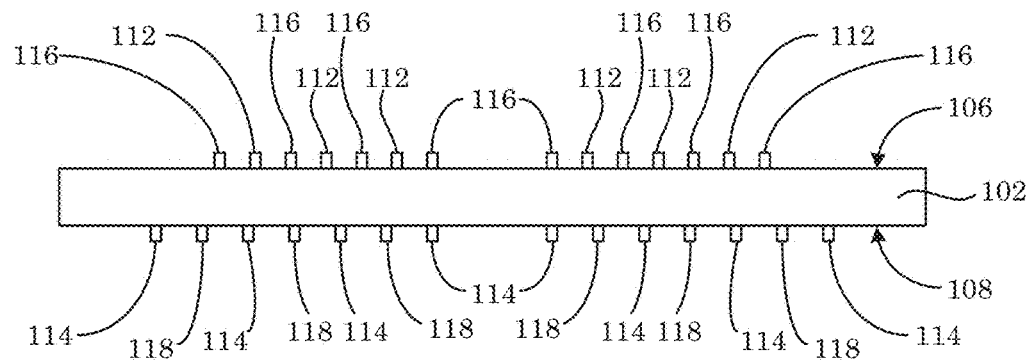
FIG. 52 shows a cross-section along line A-A of electrodes disposed on opposing surfaces of the membrane shown in FIG. 50 and FIG. 51.

Electrodes (e.g., 112, 114, 116, 118) are disposed on membrane 102 to dielectrophoretically trap cells 114 on membrane 102. A pattern of electrodes (112, 114, 116, 118) is selected so that first electrode pair 101 (comprising first electrode 112 and second electrode 116) and second electrode pair 103 (comprising third electrode 114 and forth electrode 118) independently produce an electric field strength effective to perform the dielectrophoretic trapping of cells 114 respectively on first surface 106 and second surface 108 of membrane 102. In an embodiment, with reference to FIG. 50, electrodes (e.g., 112, 116) are disposed on substrate 102 as a pair of electrodes (e.g., first electrode pair 101) in a pattern such as concentric rings. According to an embodiment, with reference to FIG. 51, electrodes (e.g., 114, 118) are disposed on substrate 102 as a pair of electrodes (e.g., second electrode pair 103) in a pattern such as concentric squares. In a certain embodiment, first electrode pair 101 is disposed on first surface 106 of membrane 102 as concentric rings (see FIG. 50), and second electrode pair 103 is disposed on second surface 108 of membrane 102 as concentric squares (see FIG. 51). FIG. 52 shows a cross-section along line A-A shown in FIG. 50 of first electrode 112 and second electrode 116 disposed on first surface 106 and 30 electrode 114 and forth electrode 118 disposed on second surface 108 of membrane 102. In some embodiments, the pattern of first electrode pair 101 is the same as the pattern of second electrode pair 103. In certain embodiments, the pattern of first electrode pair 101 is different than the pattern of second electrode pair 103.

Figure 53:
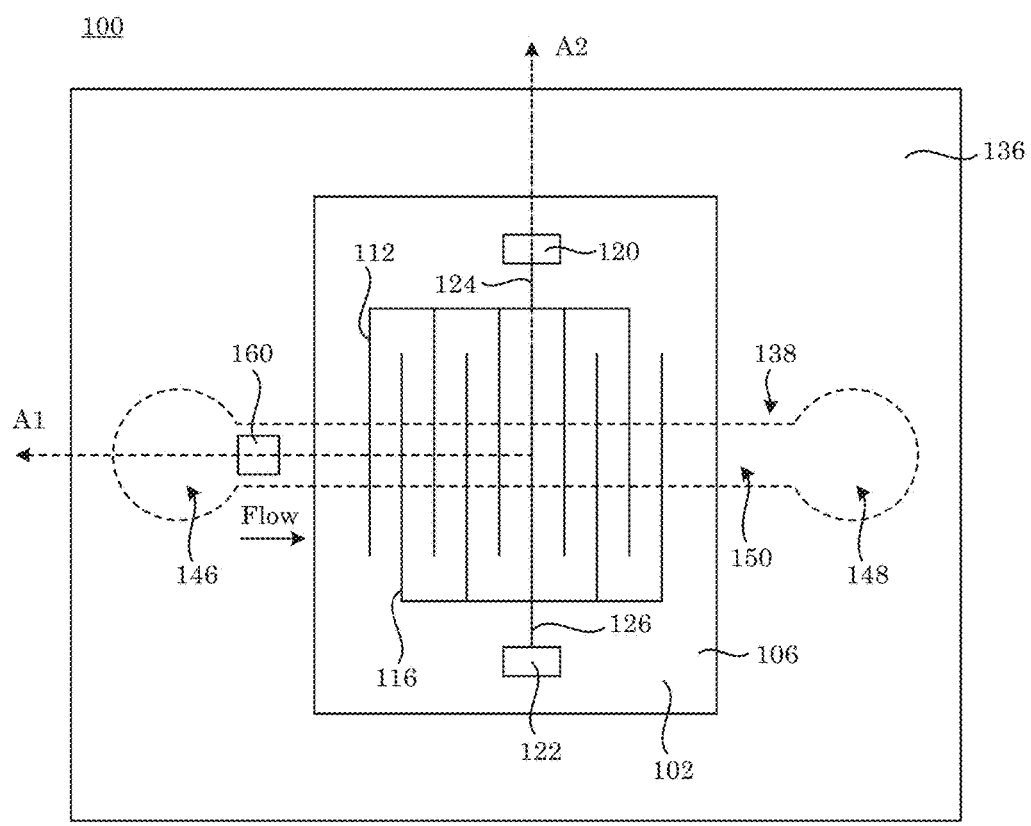
FIG. 53 shows a top view of a dual dielectropheretic article, wherein electrodes are disposed on a membrane that is disposed on a substrate.
Figure 54:
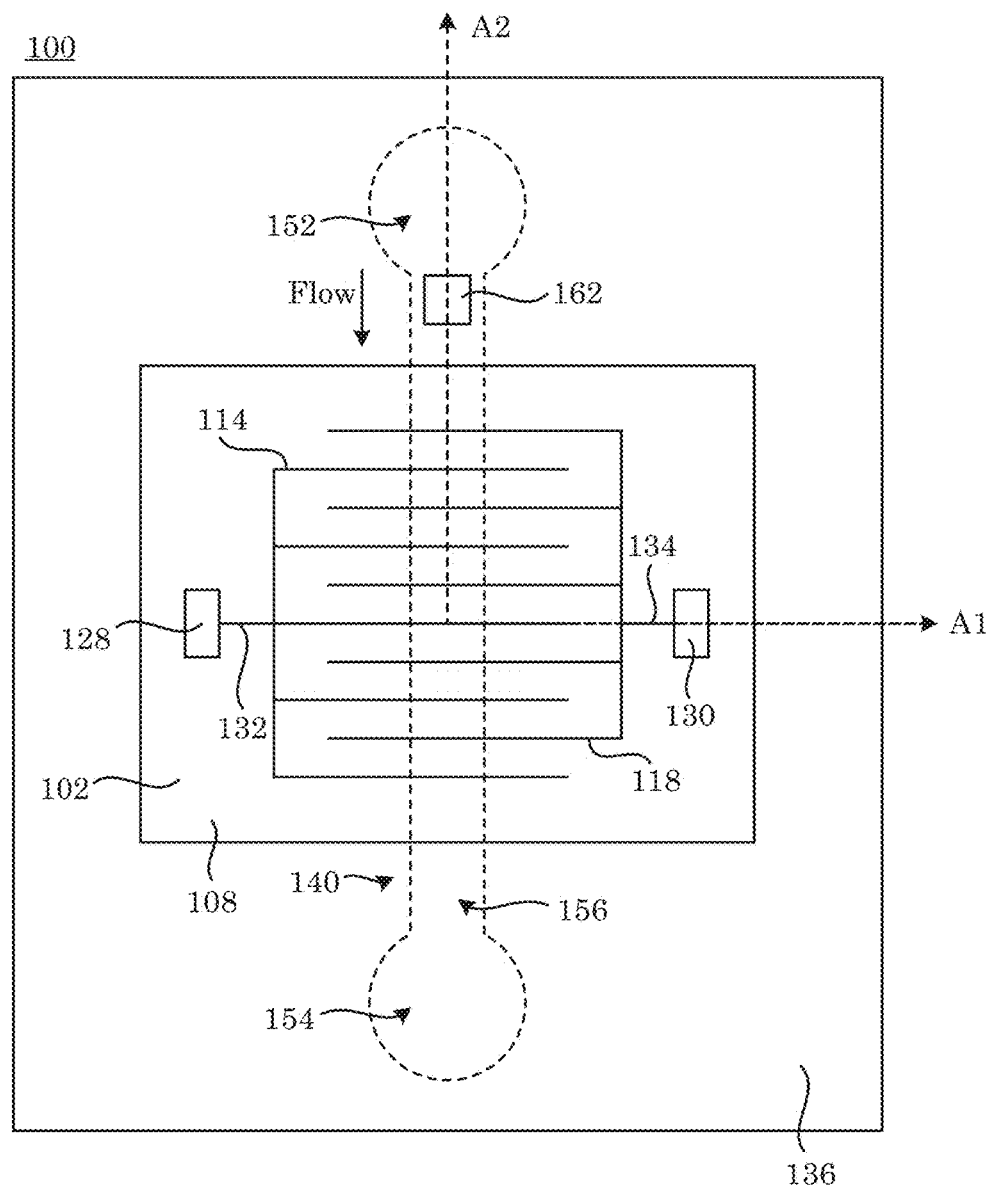
FIG. 54 shows a bottom view of the dual dielectropheretic article shown in FIG. 53, wherein electrodes are disposed on an opposing surface of the membrane with respect to the surface shown in FIG. 53.
Figure 55:
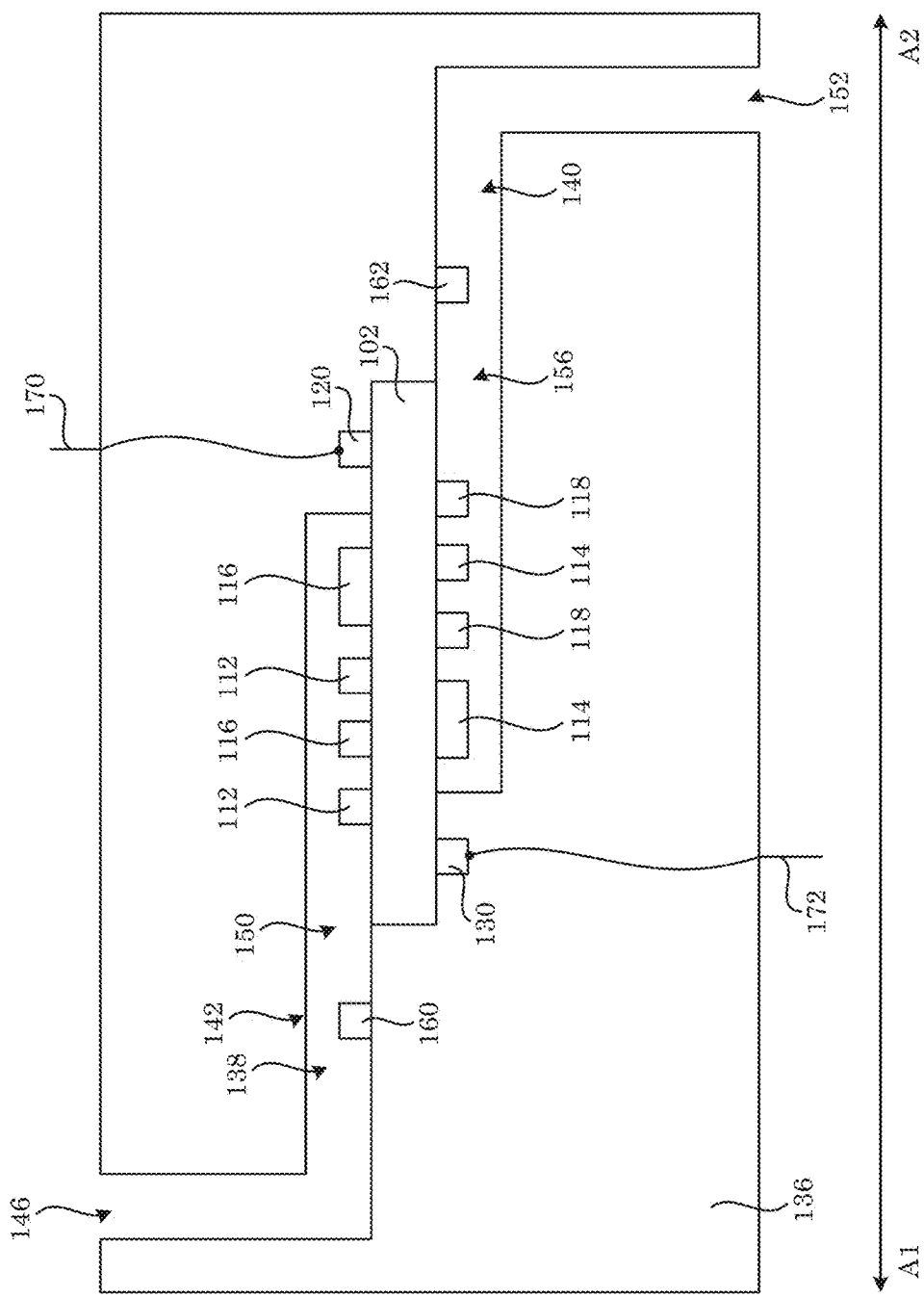
FIG. 55 shows a cross-section along line A1-A2 of the dual dielectropheretic article shown in FIG. 53 and FIG. 54.

According to an embodiment, with reference to FIG. 53 (top view), FIG. 54 (bottom view), and FIG. 55 (cross-section along line A1-A2 shown in FIG. 53), dual dielectrophoretic article 100 includes first probe electrode 160 disposed on substrate 136 or membrane 102 and in electrical communication with first flow channel 138 to provide a fifth potential for monitoring, in combination with first electrode 112, the impedance at first surface 106 of membrane 102, wherein first probe electrode is spatially separated from membrane 102. Second probe electrode 162 can be disposed on substrate 136 or membrane 102 and in electrical communication with second flow channel 140 to provide a sixth potential for monitoring, in combination with third electrode 114, the impedance at second surface 108 of membrane 102, wherein second probe electrode 162 is spatially separated from membrane 102. Here, as shown in FIG. 55, first probe electrode 160 can be electrically connected to an external power supply or impedance analyzer via electrical conductor 170 (e.g., a wire or the like). Second probe electrode 162 can be electrically connected to an external power supply or impedance analyzer via electrical conductor 172 (e.g., a wire or the like).

Figure 50:
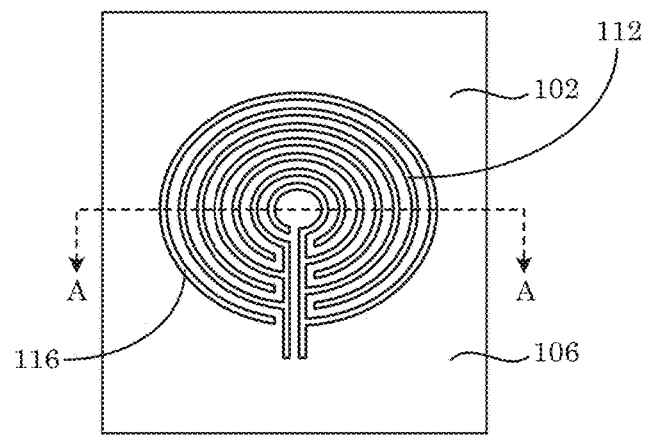
FIG. 50 shows electrodes disposed on a surface of a membrane and arranged in a pattern of concentric rings.
Figure 56:
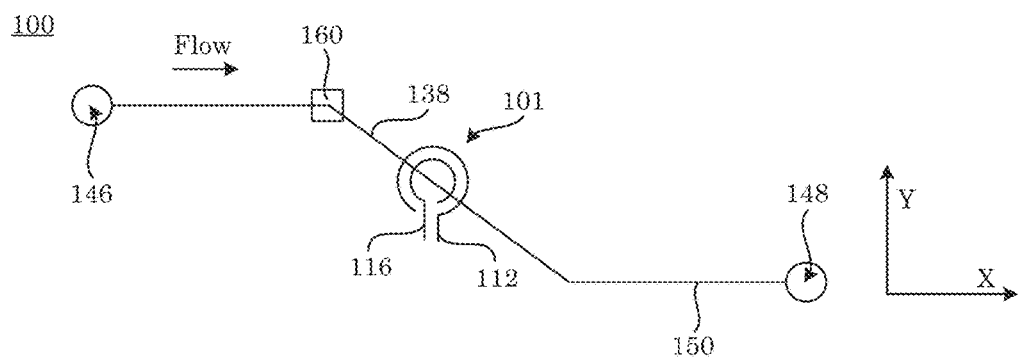
FIG. 56 shows top view of a first flow channel superimposed on electrodes that are disposed on a membrane in a dual dielectropheretic article.
Figure 57:
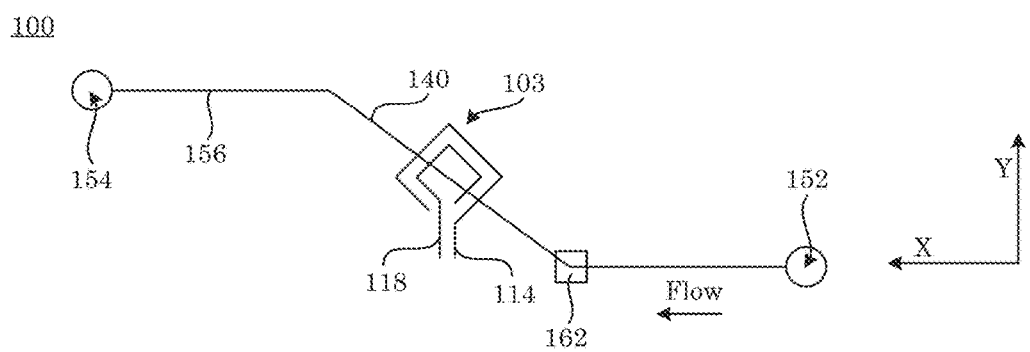
FIG. 57 shows a bottom view of the dual dielectropheretic article shown in FIG. 56, wherein a second flow channel is superimposed on electrodes that are disposed on an opposing surface of the membrane with respect to the surface shown in FIG. 56.
Figure 58:
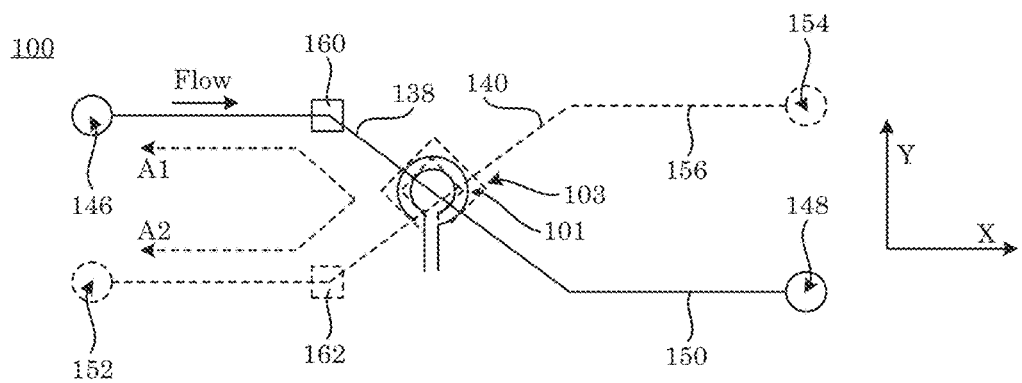
FIG. 58 shows the top view of the dual dielectropheretic article shown in FIG. 56 with the second flow channel and corresponding electrodes (shown in FIG. 57) on the bottom surface of the membrane superimposed on the first flow channel.
Figure 59:
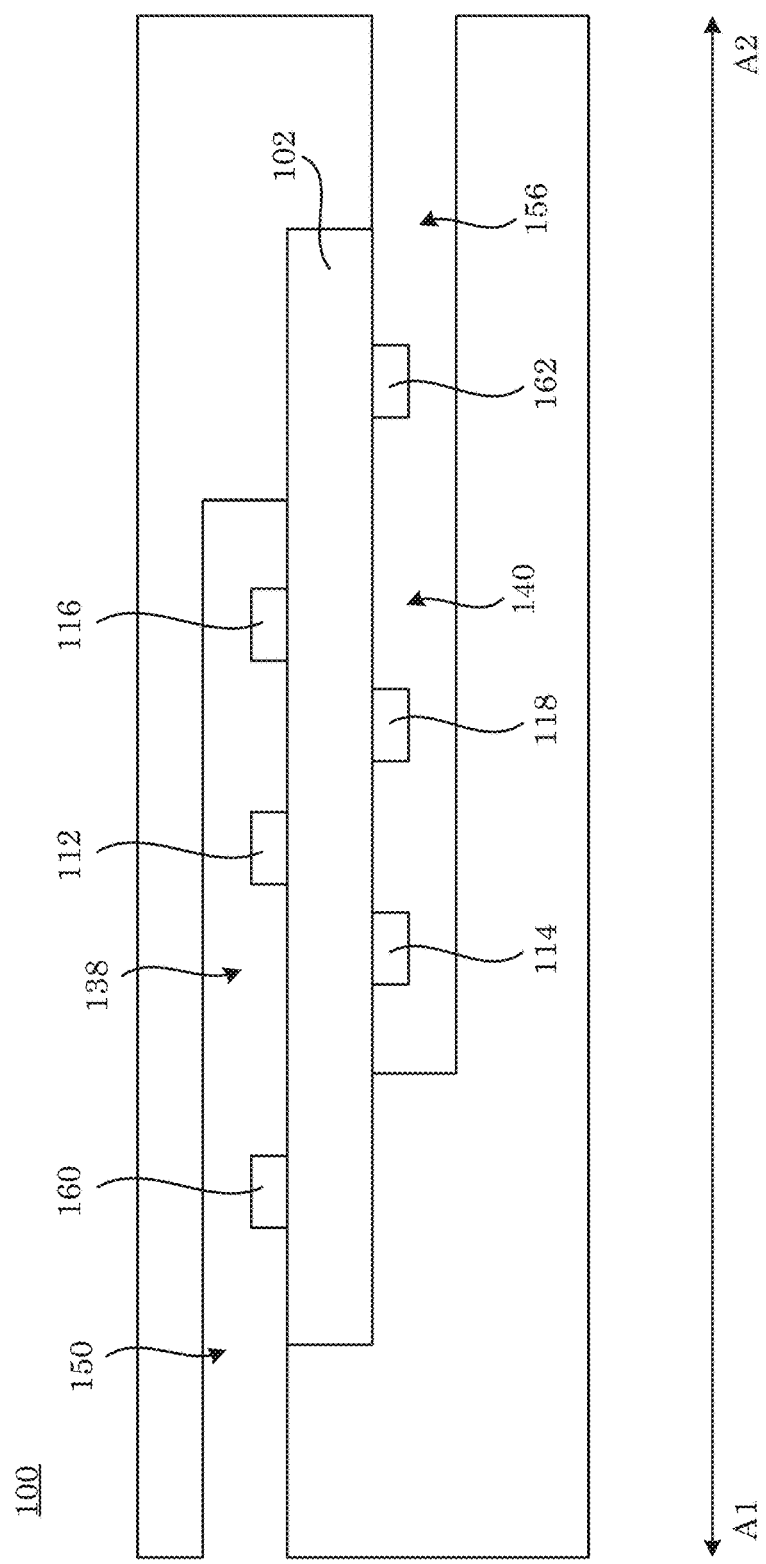
FIG. 59 shows a cross-section along line A1-A2 of the dual dielectropheretic article shown in FIG. 58.

FIG. 56 shows a relative arrangement of first flow channel 138 with respect to first probe electrode 160 and first electrode pair 101 that includes first electrode 112 and second electrode 116. Similarly, FIG. 57 shows a relative arrangement of second flow channel 140 with respect to second probe electrode 162 and second electrode pair 103 that includes third electrode 114 and forth electrode 118. FIG. 58 shows an overlay of the structures shown in FIG. 56 and FIG. 57 to illustrate the relative arrangement of first flow channel 138, first probe electrode 160, first electrode pair 101, second flow channel 140, second probe electrode 162, and second electrode pair 103 in dual dielectrophoretic article 100. Here, first electrode pair 101 includes a pattern as shown in FIG. 50, and second electrode pair 103 includes a pattern as shown in FIG. 51. FIG. 59 shows a cross-section along line A1-A2 of dual dielectrophoretic article 100 shown in FIG. 58.

In an embodiment, to determine an electrical impedance at first surface 106 and second surface 108 of membrane 102, dual dielectrophoretic article 100 includes impedance analyzer 108 electrically connected to various electrodes (e.g., 112, 114, 116, 118, 160, 162).

According to an embodiment, dual dielectrophoretic article 100 for monitoring cell migration, includes, membrane 102 to selectively migrate a plurality of cells 104 across membrane 102, membrane 102 includes: first surface 106 to receive cells 104; second surface 108 opposed to first surface 106; and a plurality of communication paths 110 disposed in membrane 102 to provide the selective migration of cells 104 across membrane 102 from first surface 106 to second surface 108; first electrode 112 disposed on first surface 106 to provide an electric field for dielectrophoresis of cells 104 at first surface 106 and to provide a first potential for monitoring an impedance at first surface 106; and third electrode 114 disposed on second surface 108 to provide an electric field for dielectrophoresis of cells 104 at second surface 108 and to provide a third potential for monitoring an impedance at second surface 108. Also, dual dielectropheretic article 100 includes: second electrode 116 disposed on first surface 106 to provide the electric field, in combination with first electrode 112, for dielectrophoresis of cells 104 at first surface 106 and to provide a second potential for monitoring the impedance at second surface 108; fourth electrode 118 disposed on second surface 108 to provide the electric field, in combination with third electrode 114, for dielectrophoresis of cells 104 at second surface 108 and to provide a fourth potential for monitoring the impedance at second surface 108; substrate 136 on which membrane 102 is disposed; first flow channel 138 disposed on substrate 136 and in fluid communication with first surface 106 to provide cells 104 to first surface 106 for dielectrophoresis of cells 104 at first surface 106 and selective migration through membrane 102 from first surface 106 to second surface 108; second flow channel 140 disposed on substrate 136 and in fluid communication with second surface 108 to receive cells 140 from second surface 108 after selective migration of cells 104 to second surface 108 from first surface 106 via communication of cells 140 through communication path 110 disposed in membrane 100 to; first probe electrode 160 disposed on substrate 136 and in electrical communication with first flow channel 138 to provide a fifth potential for monitoring, in combination with first electrode 112, the impedance at first surface 106 of membrane 102, wherein first probe electrode 160 is spatially separated from 102 or first electrode 112; and second probe electrode 162 disposed on substrate 136 and in electrical communication with second flow channel 140 to provide a sixth potential for monitoring, in combination with third electrode 114, the impedance at second surface 108 of membrane 102, wherein second probe electrode 162 is spatially separated from membrane 102 or third electrode 114. Additionally, dual dielectropheretic article 100 includes impedance analyzer in electrical communication with first electrode 112 and second electrode 116. Electrical connections between impedance analyzer 180 and various electrodes (e.g., 112, 114, 116, 118, 160, 162) are shown in FIG. 60, FIG. 61, FIG. 62, FIG. 63, and FIG. 64. In an embodiment, as shown in the electrical connection diagram of FIG. 60, impedance analyzer 180 is in electrical communication with first electrode 112 (via connection 184) and third electrode 114 (via connection 186) and further can be in electrical communication with second electrode 116 (via connection 182) and the fourth electrode 118 (via connection 188), wherein the impedance at first surface 106 is with respect to an impedance between first electrode 112 and second electrode 116, and the impedance at second surface 108 is with respect to an impedance between third electrode 114 and fourth electrode 118 as determined by impedance analyzer 180.

Figure 61:
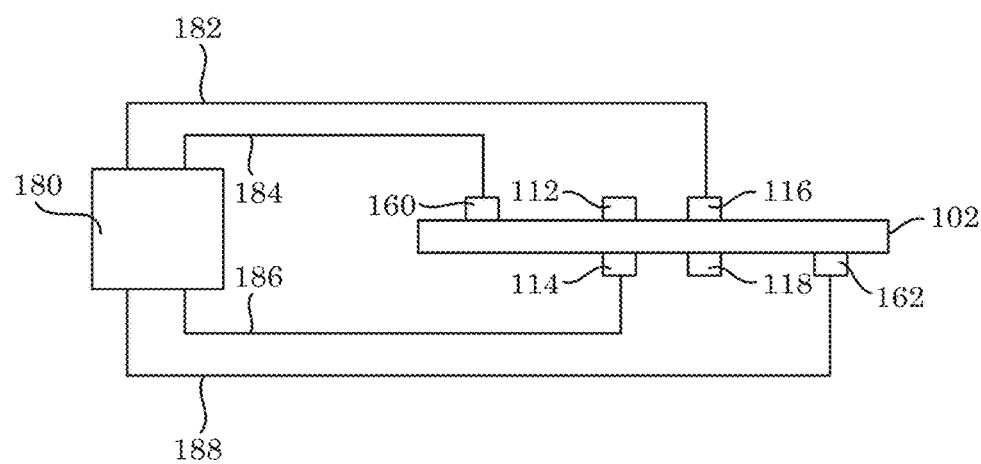
FIG. 61 shows a dual dielectropheretic article that includes an impedance analyzer electrically connected to electrodes disposed on a membrane.

In an embodiment, as shown in the electrical connection diagram of FIG. 61, impedance analyzer 180 is in electrical communication with first electrode 112 (via connection 182) and third electrode 114 (via connection 186) and further can be in electrical communication with first probe electrode 160 (via connection 184) and second probe electrode 162 (via connection 188), wherein the impedance at first surface 106 is with respect to an impedance between first electrode 112 and first probe electrode 160, and the impedance at second surface 108 is with respect to an impedance between third electrode 114 and second probe electrode 162 is determined by impedance analyzer 180.

Figure 62:
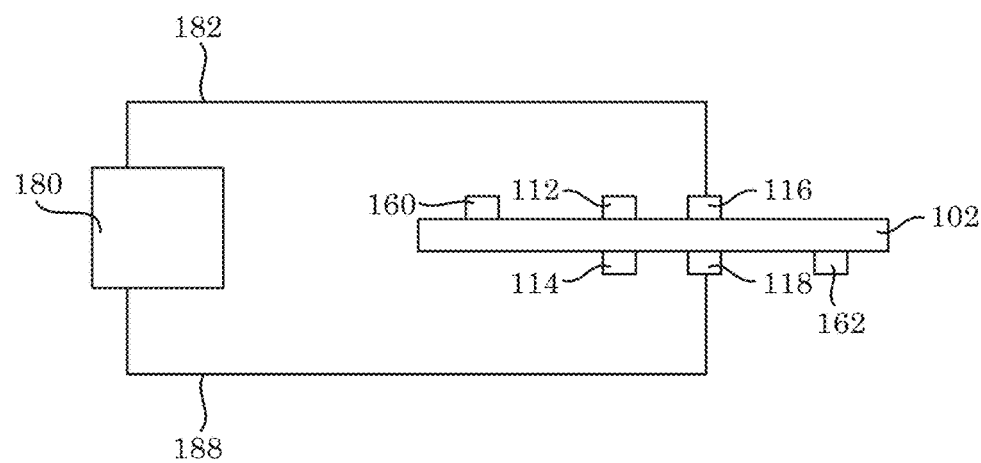
FIG. 62 shows a dual dielectropheretic article that includes an impedance analyzer electrically connected to electrodes disposed on a membrane.

In an embodiment, as shown in the electrical connection diagram of FIG. 62, impedance analyzer 180 is in electrical communication with first electrode 112 (via connection 182) and third electrode 114 (via connection 186), wherein the impedance between first surface 106 and second surface 108 is determined by impedance analyzer 180 with respect to an impedance between first electrode 112 and third electrode 118.

Figure 60:
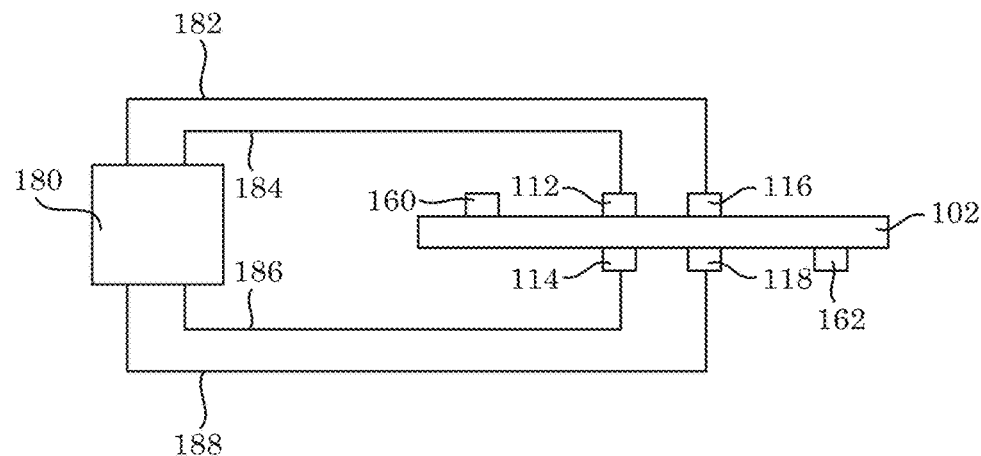
FIG. 60 shows a dual dielectropheretic article that includes an impedance analyzer electrically connected to electrodes disposed on a membrane.
Figure 63:
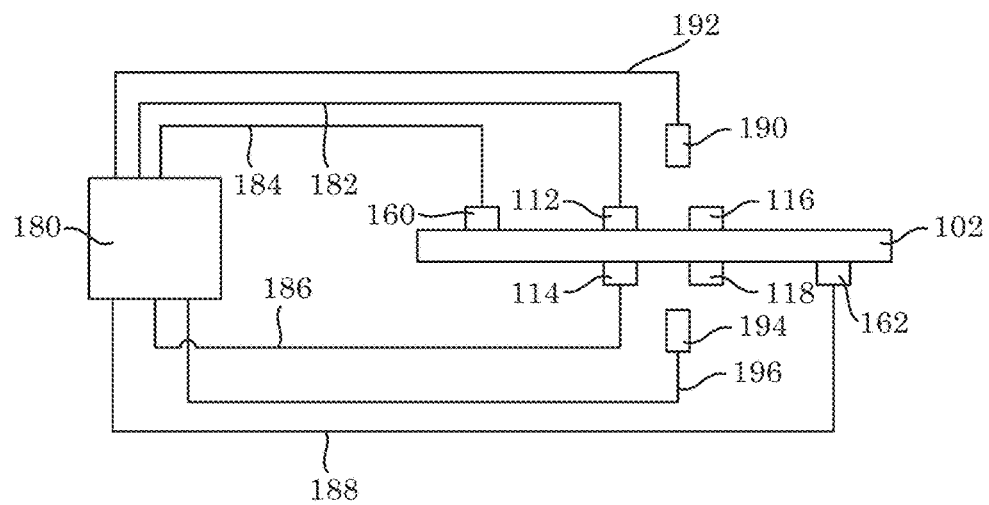
FIG. 63 shows a dual dielectropheretic article that includes an impedance analyzer electrically connected to electrodes disposed on a membrane.

FIG. 60, FIG. 61, and FIG. 62 show electrical connection configurations between impedance analyzer 180 and electrodes (112, 114, 116, 118, 160, 162) in dual dielectropheretic article 100 for a two-probe impedance measurement. FIG. 63 shows an electrical connection configuration between impedance analyzer 180 and electrodes (112, 114, 116, 118, 160, 162, 190, 194) in dual dielectropheretic article 100 for a three-probe impedance measurement. Here, impedance analyzer 180 is in electrical communication with first electrode 112 (via connection 182), third electrode 114 (via connection 186), first probe electrode 160 (via connection 184), second probe electrode 162 (via connection 188), first reference electrode 190 (via connection 192), and second reference electrode 194 (via connection 196). Impedance is determined by impedance analyzer 180 at first surface 106 is with respect to an impedance between first electrode 112 and first probe electrode 160, wherein first reference electrode 190 provides a reference voltage proximate to first electrode 112 for this measurement. Impedance is determined by impedance analyzer 180 at second surface 108 is with respect to an impedance between third electrode 114 and second probe electrode 162, wherein second reference electrode 194 provides a reference voltage proximate to third electrode 114 for this measurement.

Figure 64:
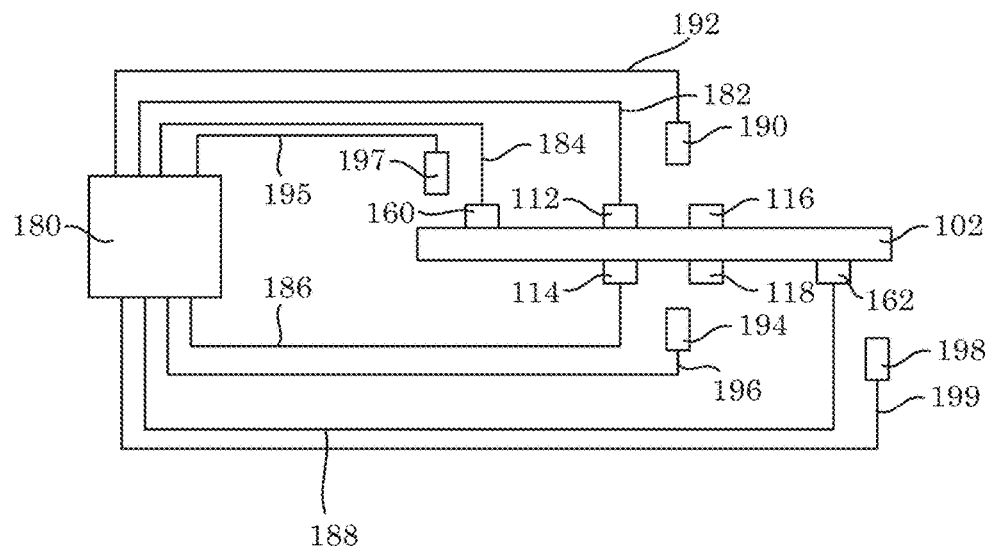
FIG. 64 shows a dual dielectropheretic article that includes an impedance analyzer electrically connected to electrodes disposed on a membrane.
Figure 65:
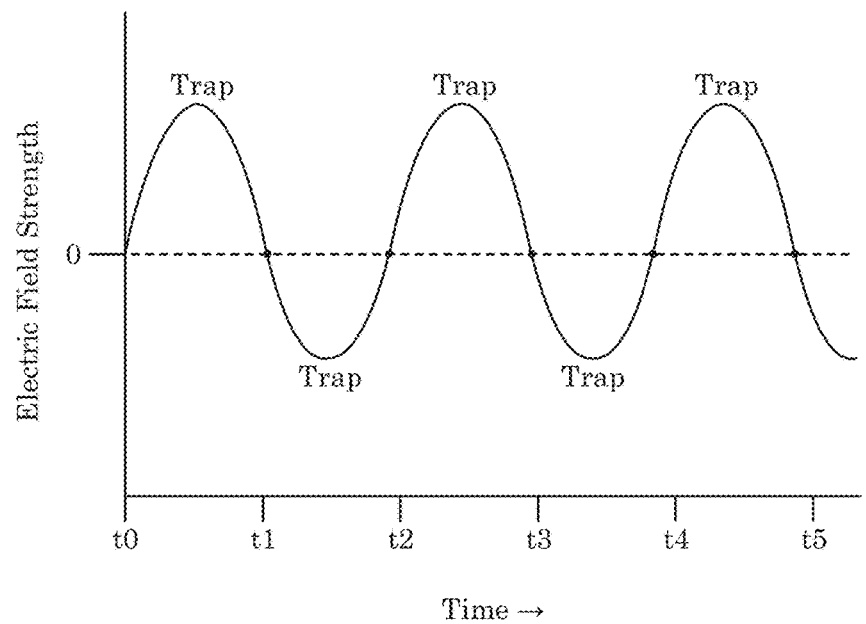
FIG. 65 shows a graph of electric field strength versus time.

FIG. 64 shows an electrical connection configuration between impedance analyzer 180 and electrodes (112, 114, 116, 118, 160, 162, 190, 194, 197) in dual dielectropheretic article 100 for a four-probe impedance measurement. Here, impedance analyzer 180 is in electrical communication with first electrode 112 (via connection 182), third electrode 114 (via connection 186), first probe electrode 160 (via connection 184), second probe electrode 162 (via connection 188), first reference electrode 190 (via connection 192), second reference electrode 194 (via connection 196), third reference electrode 197 (via connection 195), and forth reference electrode 198 (via connection 199). Impedance is determined by impedance analyzer 180 at first surface 106 with respect to an impedance between first electrode 112 and first probe electrode 160, wherein first reference electrode 190 provides a reference voltage proximate to first electrode 112, and third reference electrode 197 provides a reference voltage proximate to first probe electrode 160 for this measurement. Also, impedance is determined by impedance analyzer 180 at second surface 108 with respect to an impedance between third electrode 114 and second probe electrode 162, wherein second reference electrode 194 provides a reference voltage proximate to third electrode 114, and forth reference electrode 198 provides a reference voltage proximate to second probe electrode 162 for this measurement.

Impedance analyzer 180 can include a plurality of electrical connections to provide current or voltage to various electrodes (e.g., 112, 114, 116, 118, 160, 162), as well as a plurality of electrical connections to read current or voltage from various electrodes (e.g., 112, 114, 116, 118, 160, 162).

According to an embodiment, impedance analyzer 180 includes counter electrical connection C, working electrical connection W, counter reference CR, working reference WR connected to selected electrodes (e.g., 112, 114, 116, 118, 160, 162). Counter electrical connection C provides voltage and current from impedance analyzer 180 to selected electrodes (e.g., 112, 114, 116, 118, 160, 162), and counter reference CR reads voltage from impedance analyzer 180 to selected electrodes (e.g., 112, 114, 116, 118, 160, 162). Further, working electrical connection W reads current from selected electrodes (e.g., 112, 114, 116, 118, 160, 162), and working reference WR reads voltage from various electrodes (e.g., 112, 114, 116, 118, 160, 162).

In a certain embodiment, impedance analyzer 180 is used in a two-probe determination of impedance, wherein counter electrical connection C and counter reference CR are electrically connected together as first impedance probe P1 to provide voltage and current to selected electrodes (e.g., 112, 114, 116, 118, 160, 162), and working electrical connection W and working reference WR are electrically connected together as second impedance probe P2 to read voltage and current from selected electrodes (e.g., 112, 114, 116, 118, 160, 162).

In a certain embodiment, impedance analyzer 180 is used in a three-probe determination of impedance, wherein counter electrical connection C as first impedance probe P1 to provide voltage and current to selected electrodes (e.g., 112, 114, 116, 118, 160, 162); counter reference CR is provided as first reference probe RP1 to provide first reference voltage RV1 (e.g., to reference electrode 190), and working electrical connection W and working reference are connected together to provide the second impedance probe P2 to read voltage and current from selected electrodes (e.g., 112, 114, 116, 118, 160, 162) with reference to first reference voltage RV1 provided by first reference probe RP1.

In a certain embodiment, impedance analyzer 180 is used in a four-probe determination of impedance, wherein counter electrical connection C is first impedance probe P1 to provide current to selected electrodes (e.g., 112, 114, 116, 118, 160, 162); counter reference CR is provided as second reference probe RP2 to provide second reference voltage RV2 (e.g., to reference electrode 197); working reference WR is provided as first reference probe RP1 to provide first reference voltage RV1 (e.g., to reference electrode 190), and working electrical connection W is second impedance probe P2 to read voltage and current from selected electrodes (e.g., 112, 114, 116, 118, 160, 162) with reference to first reference voltage RV1 provided by first reference probe RP1.

Similar electrical connections to those described in the prior three paragraphs can be made from impedance analyzer 180 to electrodes (114, 118, 162) disposed on second surface 108 of membrane 102 as well as reference electrodes (194, 198) in an electrical configuration for a two-probe, three-probe, or four-probe electrical impedance determination from second surface 108.

In an embodiment, a process for making dual dielectropheretic article 100 includes providing substrate 136 (e.g., a glass or polymer); and creating second flow channel 140 in substrate 136, e.g., by removing a portion of substrate 136 if glass, semiconductor, or polymer, e.g., by etching substrate 136) or by producing second flow channel 140 by molding substrate 136 to have second flow channel 140. When molding substrate 136, a mold can be made using photolithography or any method (e.g., hot embossing, injection molding, and the like) to produce second flow channel 140 in substrate 136 to provide a selected shape and dimension of second flow channel 140. Similarly, first flow channel 138 is formed in substrate 136. The process also includes disposing electrodes (112, 114, 116, 118, 160, 162) on substrate 136 (e.g., on membrane 102) by adhering metal or other electrically conductive material for the electrodes on the surface (e.g., first surface 106 or second surface 108) of membrane 102 via a deposition (e.g., physical vapor deposition—such as electron beam evaporation, electro-deposition, and the like). Membrane 102 can be disposed on substrate 136 by mechanical deposition, mechanical transfer, solvent-assisted deposition, and the like. Cell adhesive materials can be disposed on surface (106 or 108) of membrane 102 by contacting membrane 102 with the cell adhesive material and incubating the cell adhesive material in contact with membrane 102 for a time and under conditions effective to adhere the cell adhesive material to membrane 102. In some embodiments, adhering the cell adhesive material to membrane 102 includes chemically bonding the cell adhesive material to membrane 102. In an embodiment, substrate 136 is a monolithic structure. In a certain embodiment, substrate 136 has discrete components that include a first portion that includes first flow channel 138; and a second portion that includes second flow channel 140, wherein the first portion and the second portion are disposedly attached to one another such that membrane 100 to is interposed between the first portion and the second portion to provide a flow barrier between first flow channel 138 and second flow channel 140.

In an embodiment, a process for determining impedance in a dual dielectropheretic article includes: providing dual dielectropheretic article 100 including impedance analyzer 180 electrically connected to electrodes (112, 114, 116, 118, 160, 162); flowing a first composition including cells 104 in first flow channel 106; contacting first electrode 112 and second electrode 116 with the first composition; producing an electric field between first electrode 112 and second electrode 116 by providing a potential difference between first electrode 112 and second electrode 116; subjecting cells 104 in the first composition to dielectrophoretic trapping on first surface 106 of membrane 102 in a presence of the electric field between first electrode 112 and second electrode 116; removing the electric field between first electrode 112 and second electrode 116; providing a first alternating current (AC) voltage VAC1 to one of first electrode 112 or first probe electrode 160; monitoring a first electrical response of first electrode 112 or first probe electrode 160 that was not provisioned with the first AC voltage VAC1; providing second AC voltage VAC2 to one of third electrode 114 or second probe electrode 162; monitoring a second electrical response of third electrode 114 or second probe electrode 162 that was not provisioned with second AC voltage VAC2; and converting the first electrical response to a first impedance Z1 at first surface 106 to determine the impedance of the dual dielectropheretic article. The process also can include converting the second electrical response to a second impedance Z2 at second surface 108.

For dielectrophoretically trapping of cells 104 on membrane 102, electrodes (112, 116; 114, 118) disposed on membrane 100 to produce an electric field in response to an applied AC voltage on one electrode (e.g., first electrode 112) as the other electrode (e.g., second electrode 116) is grounded to generate dielectrophoretic forces on cells 104 and first flow channel 138. FIG. 63 shows a graph of electric field strength versus time for an exemplary dielectrophoretic trapping waveform in which cells 104 are dielectrophoretically trapped between times t0 and t1, t1 and t2, t2 and t3, t3 and t4, and t4 and t5, and the like, while the electric field strength is zero at t0, t1, t2, t3, t4, t5 such that cells 104 are not dielectrophoretically trapped. It should be appreciated that cells 104 accumulate on first surface 106 of membrane 102 after time t0 due to dielectrophoretic trapping and are immobilized on first surface 106 and are not released from first surface 106 once dielectrophoretically trapped thereon. These dielectrophoretic forces experienced by cells 104 are used to trap cells 104 in a specific area within dual, particularly on membrane 102. The dielectrophoretic waveform is generated at a frequency specific for the type of cells 104 to attract cells 104 proximate to first electrode pair 101 (including for selector 112, second electrode 116) on membrane 102 that is coated cell adhesive material.

For dielectrophoretic trapping, an amplitude of voltage subjected to electrodes (112, 114, 116, 118) can be from 0.1 $V_{p-p}$ to 20 $V_{p-p}$, specifically from 0.5 $V_{p-p}$ to 7 $V_{p-p}$, and more specifically from 0.7 $V_{p-p}$ to 1.2$V_{p-p}$. The electric field strength between for selector 112 and second electrode 116 can be from 0.1 $V_{p-p}$ to 10 $V_{p-p}$, specifically from 0.5 $V_{p-p}$ to 7 $V_{p-p}$, and more specifically from 0.7 $V_{p-p}$ to 1.2$V_{p-p}$. A frequency of the dielectrophoretic waveform can be from 0.1 MHz to 100 MHz, specifically from 1 MHz to 10 MHz, and more specifically from 7 MHz to 10 MHz.

After dielectrophoretic trapping, the dielectrophoretic trapping waveform is terminated so that cells 104 remain disposed on first surface 106 but can move (e.g., laterally) on first surface 106 or migrate from first surface 106 to second surface 108.

Figure 66:
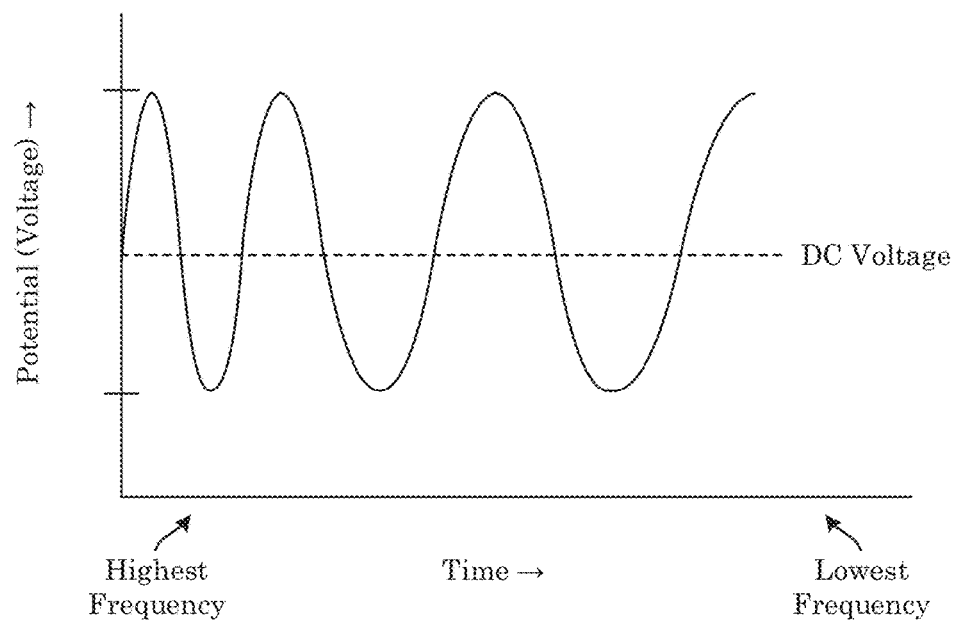
FIG. 66 shows a graph of potential versus time.

Migration of cells 104 from first surface 106 to second surface 108 of membrane 102 is electronically monitored by impedance analyzer 180 with impedance spectroscopy to determine temporally electrical resistance and capacitance of first electrode pair 101 or second electrode pair 103 over a range of frequencies (e.g., from 10 Hz to 100 kHz). A two-probe electrical impedance configuration includes electrically connecting impedance analyzer 180 to electrodes of dual dielectropheretic article 100 such that counter electrical connection C provides the electrical signal, and working electrical connection W acquires the response from electrodes of dual dielectropheretic article 100. Referencing of electrical signals can be accomplished by electrically connecting the counter reference electrical connection CR and working reference electrical connection WR to respective references (e.g., thin-film silver/silver-chloride electrochemical reference) to provide signal stabilization or controlled by impedance analyzer 180 or by utilizing external electrochemical reference electrodes (e.g., silver/silver-chloride electrochemical reference disposed proximate to working electrical connection W in dual dielectropheretic article 100) in a three-probe or four-probe impedance determination configuration. To stimulate electrodes in dual dielectropheretic article 100 or avoid electrochemical reactions, a low amplitude (in voltage) sine wave (e.g., from 10 $mV_{p-p}$ to 50 $mV_{p-p}$) is floated at a minor DC offset (e.g., from −25 mV to 25 mV) and applied to the counter electrical connection C as shown in FIG. 66, which shows a graph of potential versus time, wherein a frequency of the sinewave can be swept from a higher frequency (initially) to a lower frequency and longer times.

In an embodiment, dual dielectropheretic article 100 is used to monitor or determine various conditions, including media conditions, spreading of cells 104 on membrane 102 (on first surface 106 or second surface 108), and migration of cells 104 between first surface 106 and second surface 108).

Media conditions are monitored by first electrode pair 101 on first surface 106 or by second electrode pair 103 on second surface 108 of membrane 102. Spreading of cells 104 is monitored by: first electrode pair 101 or second electrode pair 103; first electrode 112 and first probe electrode 160; third electrode 114 and second probe electrode 160; first electrode 112 and reference electrode 190; third electrode 114 and second electrode 162; or a combination thereof. Here, the impedance between these electrodes are recorded in discrete intervals. As the conditions shift over time, the impedance will shift in accordance, thus providing an electrical means of monitoring the media conditions.

Figure 67:
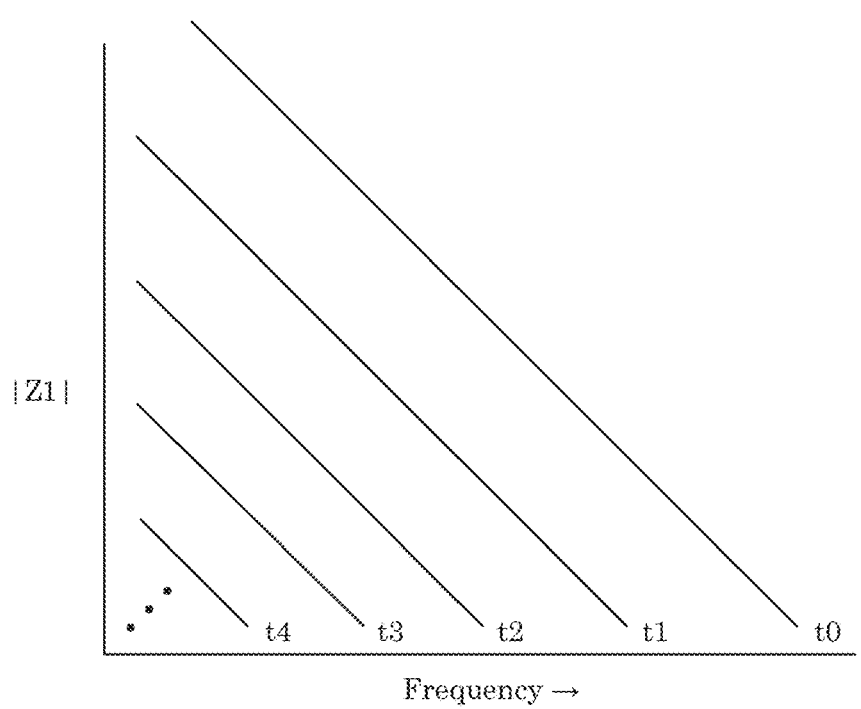
FIG. 67 shows a graph of impedance versus frequency.
Figure 68:
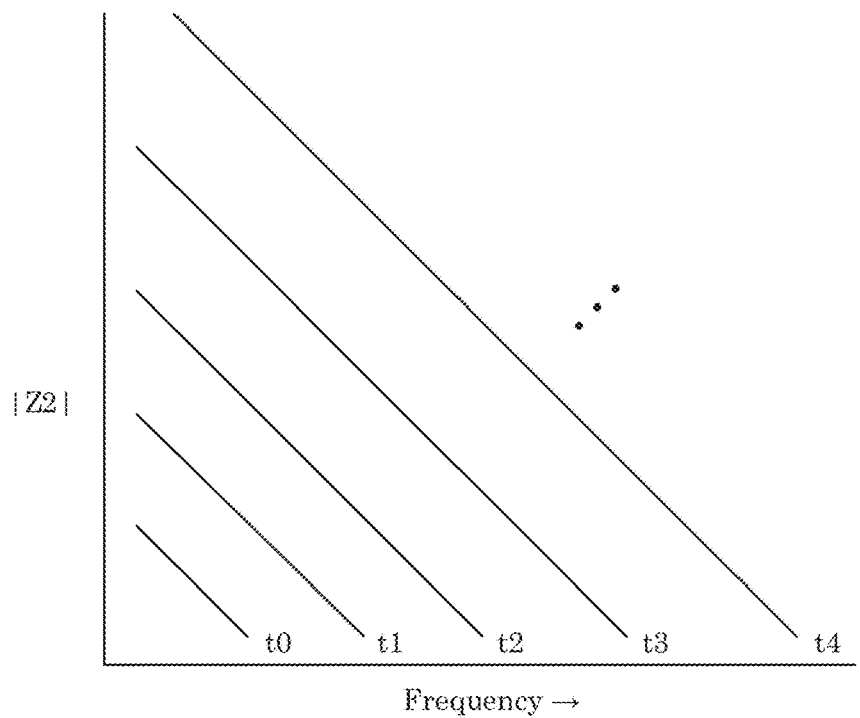
FIG. 68 shows a graph of impedance versus frequency.

Impedance measurements by impedance analyzer 180 provide determination of migration of cells 104 from first surface 106 to second surface 108, and migration of cells 104 can be monitored by using electrodes on opposing surfaces (i.e., first surface 106 and second surface 108) of membrane 102, e.g., to determine movement of cells 104 in response to being induced to migrate. These measurements are recorded over time to monitor the progression of cell culture such as cell growth, cell division, cell migration and the like. In an embodiment, the measurements are performed by applying a voltage (e.g., 25 mV) to first electrode 112 while second electrode 116 is grounded, e.g., in an absence of first reference electrode 190. In a presence of reference electrode 190, the applied voltage is referenced against first reference voltage RV1 applied to first reference electrode 190. It is contemplated that cells 140 are induced to migrate by natural invasiveness, chemotaxis, durotaxis, nutrient gradients, and the like. As shown in FIG. 67, which is a graph of a magnitude of first impedance Z1 at first surface 106 versus a frequency of the AC waveform (see FIG. 66) applied to first electrode 112, first impedance Z1 decreases from initial time t0 to later time t4. Without wishing to be bound by theory, a change in first impedance Z1 is ascribed to migration of cells 104 such that a decrease in first impedance Z1 implies cells 104 migrate from first surface 106 to second surface 108. Accordingly, as shown in FIG. 68, which is a graph of a magnitude of second impedance Z2 at second surface 108 versus a frequency of the AC waveform (see FIG. 66) applied to third electrode 114, second impedance Z2 increases from initial time t0 to later time t4. Without wishing to be bound by theory, a change in second impedance Z2 is ascribed to migration of cells 104 such that an increase in second impedance Z2 implies cells 104 migrate from first surface 106 to second surface 108.

Figure 69:
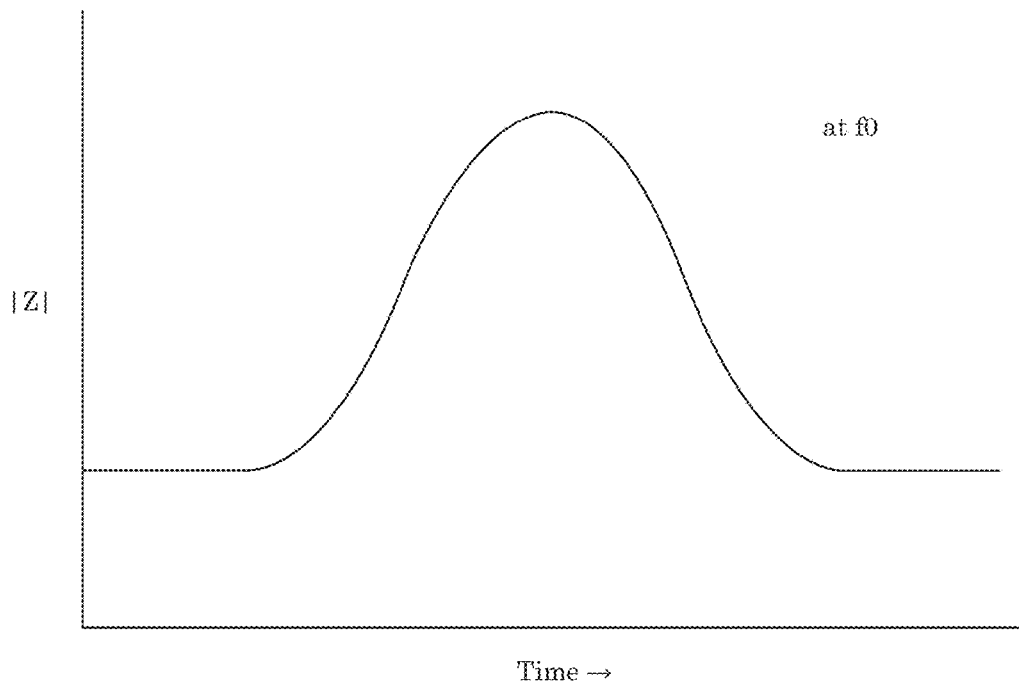
FIG. 69 shows a graph of impedance versus time any fixed frequency.
Figure 70:
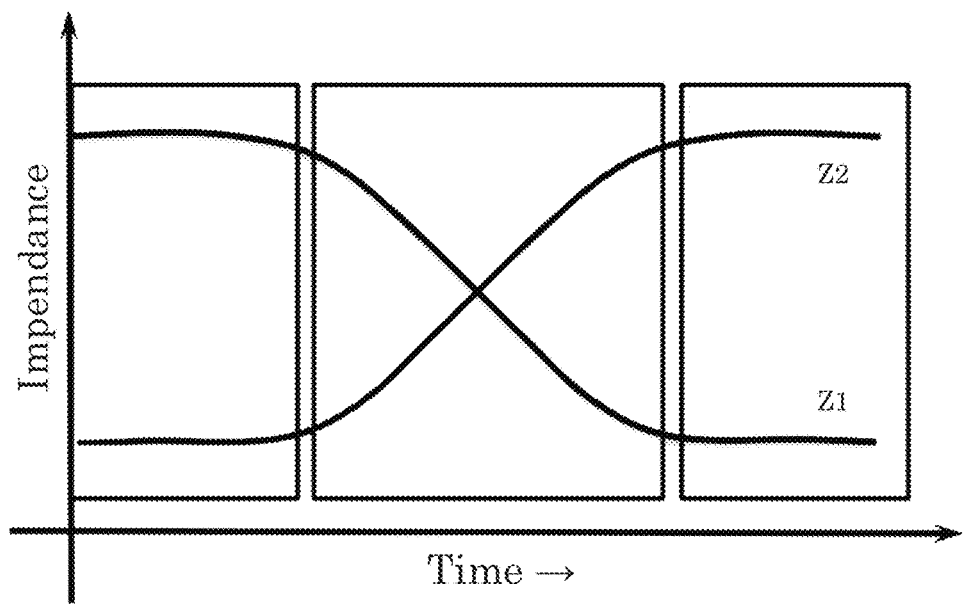
FIG. 70 shows a graph of impedances versus time.
Figure 71:
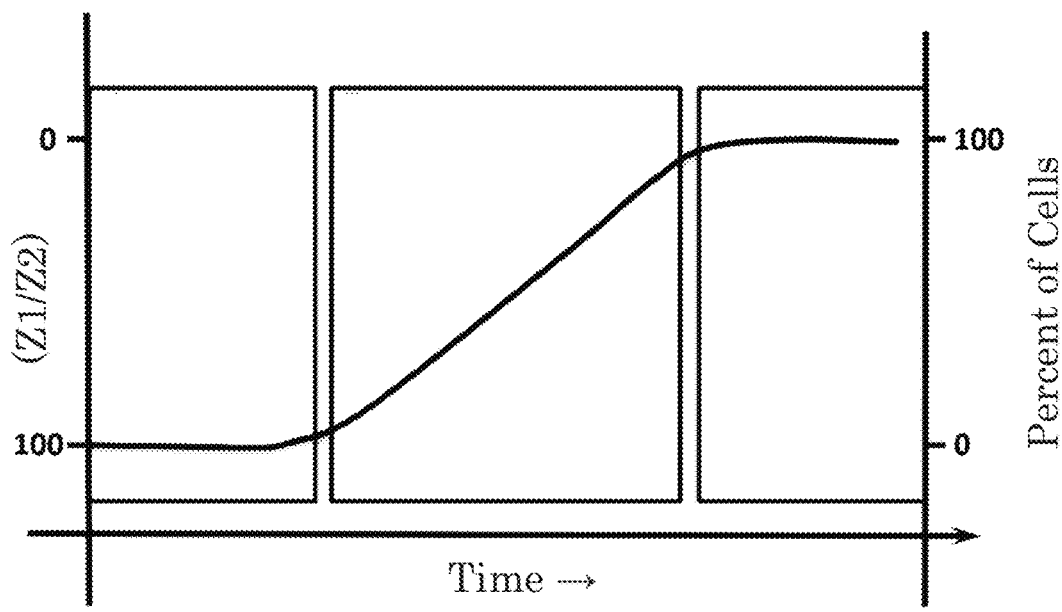
FIG. 71 shows a graph of a ratio of impedances versus time.

In a particular embodiment, impedance analyzer 180 is electrically connected to several electrodes of dual dielectropheretic article 100 such that first electrode 112 and third electrode 114 are respectively connected to counter electrode C and working electrode W of the impedance analyzer 180. In this manner, impedance is determined across membrane 102 from first electrode 112 to electrode 114. Here, with reference to FIG. 69 (which shows a graph of a magnitude of impedance across membrane 102 versus time), impedance is determined at a fixed frequency, and the impedance increases, go through a maximum value, and decreases, which demonstrates the series of events for the cells to spread on the surface, undergo division, become stimulated to migrate, and conclude migration. FIG. 70 shows a graph of impedance versus time for first impedance Z1 at first surface 106 and for second impedance Z2 at second surface 108. Accordingly, advantageously and unexpectedly, dual dielectropheretic article 100 provides quantitative measurement in real-time of migration of cells 140 from first surface 106 to second surface 108 of membrane 102. Further, dual dielectropheretic article 100 provides such quantitative information by comparing impedance measured from initial time (e.g., t0) on both sides of membrane 102 versus impedance during a time course (the time it takes cells 104 to migrate from first surface 106 to second surface 108) as shown in FIG. 71, which is a graph of a ratio of first impedance Z1 to second impedance Z2 versus time. Here, the ratio starts at a minimum value and increases to a maximum value.

Beneficially, dual dielectropheretic article 100 includes membrane 102 disposed on substrate 136 and also includes microfluidic channels (e.g., first flow channel 138 and second flow channel 140) to provide a selected flow condition (e.g., stagnant or active flow) therethrough. In an embodiment, flow of cells 104 through first flow channel 138 or second flow channel 140 resembles different physiological conditions. Additional advantages include microfluidics properties such as small samples (microliter to picoliter volumes), small amount of waste generated or chemicals used, better microenvironment control, and the like.

Additionally, impedance data acquired by dual dielectropheretic article 100 provide a ratio of electrical measurements (e.g., Impedance at first surface/Impedance at second surface) that changes as migration of cells 140 occurs. Accordingly, dual dielectropheretic article 100 provides normalized quantification due to electrodes (112, 114, 116, 118, 160, 162) being present in the same article instead of separate articles. Moreover, dual dielectropheretic article 100 provides accumulation of cells 104 at first surface 106 of membrane 102 by DEP trapping using electrodes (112, 116) disposed on membrane 102. Further, electrodes (112, 116) provide electrical measurement of impedance. Accordingly, dual dielectropheretic article 100 provides selective control of the number of cells 104 trapped on first surface 106 of membrane 102.

Figure 72:
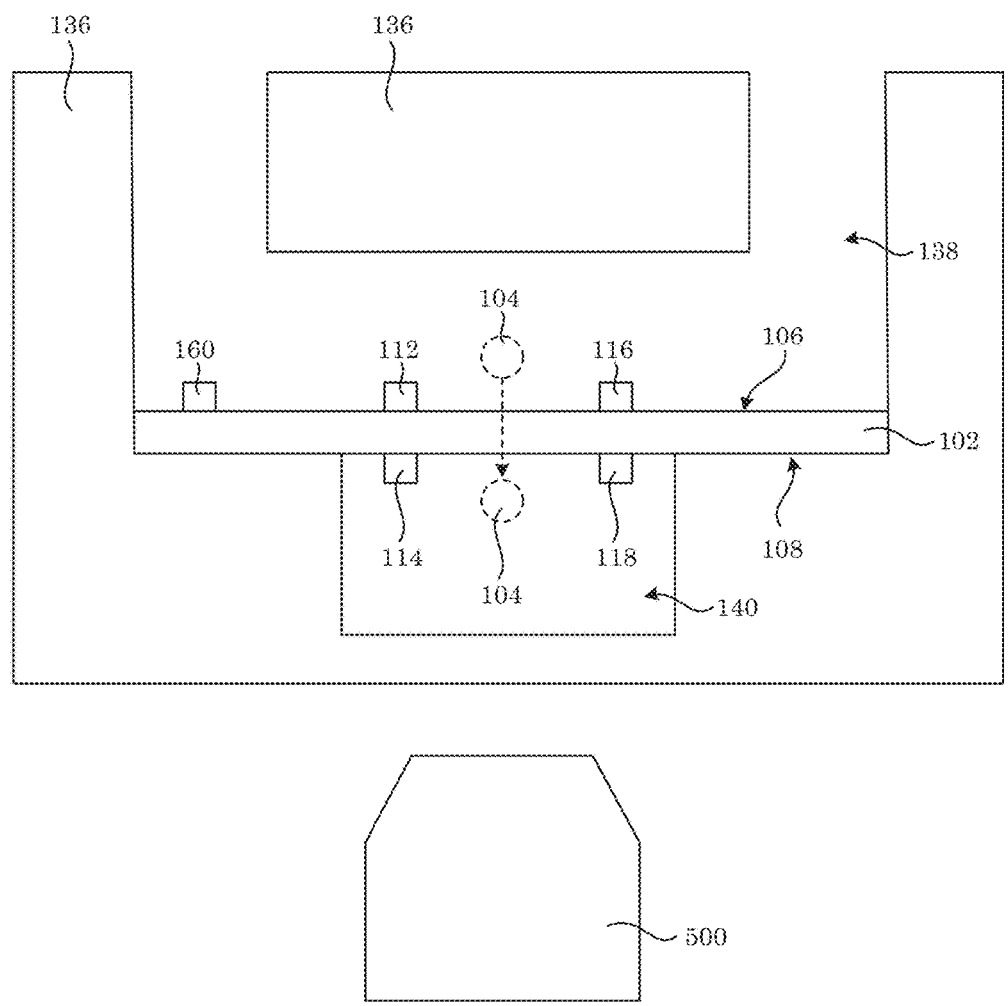
FIG. 72 shows a graph of a dual dielectropheretic article.

In an embodiment, dual dielectropheretic article 100 includes optical detection of migration of cells 104 and spreading thereof. With reference to FIG. 72, dual dielectropheretic article 100 can include optical detector 500 (e.g., a microscope objective or additional optics) to monitor movements of cells 104 through pores 110 of membrane 102. Further, optical detector 500 can provide optical microscopy in a continuous or discrete measurement of migration onto second surface 108 of cells 104. In this manner, optical detector 500 can be a microscope to determine cell morphology or provide imaging of cells 104. In an embodiment, optical microscopy provided by optical detector 500 and impedance provided by impedance analyzer 180 are used to monitor migration of cells 104 across membrane 102.

The articles and processes herein are illustrated further by the following Examples, which are non-limiting.

EXAMPLES

Materials

Example 1

Poly(allylamine hydrochloride) (PAH, MW=70,000), PAH-Fluorescein isothiocyanate (FITC), monoclonal anti-neurofilament antibody produced in mouse, anti-mouse IgG-FITC, retinoic acid 98%, FN, sucrose, poly-L-lysine, and polystyrene pellets were purchased from Sigma-Aldrich (St. Louis, Mo.). Poly(styrenesulfonic acid) (PSS, MW=70,000) was purchased from Polysciences, Inc. (Warrington, Pa.). Poly(dimethylsiloxane) (PDMS, Sylgard 184) was purchased from Dow Corning (Midland, Mich.). Alpha Minimum Essential Medium (αMEM) with ribonucleosides and deoxyribonucleosides, calcein AM, ethidium homodimer-1, 6-carboxy-X-rhodamine, succinimidyl ester (6-ROX-NHS), and fetal bovine serum (FBS) were obtained from Invitrogen Corporation (Carlsbad, Calif.). P19 cells, 0.25% trypsin-ethylenediaminetetraacetic acid (EDTA) and calf bovine serum (CBS) were purchased from ATCC (Manassas, Va.). Purecol (acidified bovine collagen I) was purchased from Advanced BioMatrix (San Diego, Calif.). Dulbecco's phosphate-buffered saline (DPBS) and phosphate-buffered saline (PBS) were obtained from Mediatech, Inc. (Hernon, Va.). Indium tin oxide (ITO)/glass substrates were purchased from Delta Technologies (Stillwater, Minn.), and 22 mm×22 mm #1.5 Corning coverslips were obtained from Daigger (Vernon Hills, Ill.). Electrically conductive adhesive was purchased from Epoxy Technology Inc. (Billerica, Mass.). Octyldimethylchlorosilane was obtained from Gelest Morrisville, Pa.). SU-8 photoresist and developer were obtained from MicroChem Corp. (Newton, Mass.).

Cell Culture

P19 cells were cultured in αMEM with ribonucleosides and deoxyribonucleosides. The growth medium was supplemented by adding 7.5% of bovine calf serum and 2.5% fetal bovine serum (37.5 mL and 12.5 mL in a total of 500 mL of αMEM, respectively). Growth medium was renewed every 2 d, and cells were subcultured every 2 days to 3 days at a dilution ratio of 1:10. Cells were maintained in a humidified environment with 5% carbon dioxide and a temperature of 37° C.

Coverslips were cleaned with isopropyl alcohol (IPA) using a lint-free cloth wipe and were blown dry with compressed nitrogen (N2) before placing them flat on a glass Petri dish. An 8 mg/mL polystyrene (PS) solution prepared in toluene was spin coated (418.9 rad/s, 50 s) onto the coverslips, and the PS-spin coated coverslips (PS thickness between 55 nm to 85 nm) were placed in a vacuum chamber for 3 hours to remove any residual solvent. All PS-coated coverslips were plasma oxidized prior to cell adhesive material deposition.

Cells were seeded in sucrose and in cell culture media (CCM) on coverslips coated with natural or synthetic materials. Incubation times were different for each material and pretreatment. Coverslips pretreated with CCM prior to cell seeding were incubated with the CCM for 1 hour at 37° C. Additional coverslips were incubated with Collagen I (Col I, 30 μg/mL), poly-L-Lysine (1 mg/mL), and FN (25 μg/mL to 50 μg/mL) for 90 minutes at 4° C. PAH and PSS solutions (1 mg/mL, mol/L (M) concentrations of the repeating units: PAH=10.7 mmol L−1 and PSS=4.8 mmol L−1) were each prepared in 18.2 MΩ filtered deionized water (DI-water). The pH of the PAH and PSS solutions was adjusted to 5 and 6, respectively. Four alternating PEMs, (PAH/PSS)2, were deposited onto the oxidized PS surface of the coverslips by immersing the coverslip in the polyelectrolyte solutions sequentially. The initial PAH layer was deposited for 40 min. The coverslip surface was rinsed with DI-water twice before applying subsequent alternating layers for 10 minutes with two DI-water rinses between each incubation. After the fourth layer was deposited, the PAH outermost layer (fifth layer) was deposited for at least 30 minutes at room temperature (approximately 21° C.±2° C.). P19 cells were then seeded in a 0.32 mol/L sucrose solution for 15 minutes at room temperature, and then the sucrose was aspirated and CCM was added to the cells. Images at 0 hours (after adding CCM at the end of sucrose exposure) and 24 hours were taken to assess the morphology differences and adherent status of the seeded cells. The number of cells adhered to the substrates and the number of rounded (i.e. unhealthy) cells were determined with ImageJ software and the surface that had the highest number of cells with the lowest number of rounded cells were selected for use in the DEP device.

Coverslips for the deposition of the hCAM were prepared using the same procedure previously described, but to promote better adhesion of the spin-coated polystyrene the following silanization step was added prior to spin coating the polystyrene. Cleaned coverslips in a Petri dish were placed in a dessicating chamber containing a Teflon holder with 200 μL of octyldimethylchlorosilane. House vacuum was applied to the chamber for 2 h, and then the Petri dish was placed in a 60° C. oven for at least 3 h. All PS-coated coverslips were plasma oxidized prior to PEM deposition. PEMs were deposited as described in the previous section, except that after the fourth layer was deposited, the wells were rinsed twice and then stored overnight with DI water at room temperature.

The PEM coated coverslips were then incubated in a 50 μg/mL solution of FN prepared in DPBS at 4° C. for 1.5 h. The coverslips were rinsed twice with PBS, and the final hCAM layer was deposited by incubating the coverslips in 1 mg/mL PAH for 45 minutes at 4° C. The hCAM coverslips were rinsed twice with DI-water and then transferred to PBS in a new well in a 6-well cell culture plate until cell seeding.

The hCAM was deposited on the ITO electrode substrates as described above, except it was applied in a microfluidic polydimethylsiloxane (PDMS) channel covering the DEP electrodes. In this case, the solutions were added to the channel inlet and flowed down the channel previously aligned onto the DEP electrodes. Once each deposition was completed, the solutions were aspirated via the channel outlet. The incubation times and the concentration of the solutions remained the same.

A 0.32 mol/L (M) sucrose solution was prepared in DI-water to mimic the osmolarity of the P19 cell culture media but with low electrolyte concentration to maximize DEP forces. Confluent (80%) P19 cells were trypsinized with 0.25% trypsin-EDTA, and were divided into two 15 mL centrifuge tubes. The cells were centrifuged for 7 minutes at 83.8 rad/s and 5° C. At this point the cells were ready for incubation with sucrose at different time points (0 min, 15 min, 30 min, 45 min, 60 min). For the 0 minutes sample, one tube of cells was resuspended in cell culture media, and the cells were seeded onto the hCAM coverslips at a dilution ratio of 1:10 (approximately 4700 cells/cm2). The second tube of cells was resuspended in the sucrose solution, and the cells were seeded onto the same substrate at an identical cell seeding density (approximately 4700 cells/cm2). After each sucrose incubation time point, 4 mL of cell growth media was added to the samples to dilute the sucrose (a 1/27 dilution, 3.7% final sucrose solution) and restore to normal cell culture conditions. Phase contrast images of the P19 cell growth on the hCAM were taken at 0 h, 24 h, and 48 h.

P19 cell viability on the hCAM surface was assessed after 48 hours using the LIVE/DEAD viability assay kit from Invitrogen Corp. Calcein AM (excitation/emission maxima at 495 nm/515 nm) was used to stain the viable cells, which exhibit intracellular esterase activity, while ethidium homodimer-1 (EthD-1) (excitation/emission maxima at 495 nm/635 nm) was used to label dead cells with damaged plasma membranes.

Calcein AM and EthD-1 were diluted to 2 μmol/L and 4 μmol/L, respectively, in a single solution in DPBS. 1 mL of the dye solution was added to each well, and the 6-well plates were placed in the incubator for 45 min. The cells were imaged immediately using phase contrast optics and FITC and Rhodamine filter sets. The images were taken in triplicates for each time point. Viable and dead cells were counted manually, and the percentage of each was expressed based on the total number of cells per frame. A minimum of 440 cells, per frame, were counted.

SU-8 masters with raised features (30 μm to 35 μm height, 1000 μm wide) for molding PDMS microchannels were fabricated using the manufacturer's protocol. PDMS microfluidic structures were molded by pouring the polymer on the SU-8 master and curing at 100° C. for 1 hour (from manufacturer's product information sheet).

ITO electrodes were made from ITO/glass substrates. The ITO surface was patterned using conventional photolithographic methods. A negative photoresist was spin coated on the ITO surface and then exposed to UV light through a chrome mask containing the electrode design. The pattern was developed, and the exposed ITO was etched using a 9 mol/L (M) hydrochloric acid (HCl) solution. The remaining ITO pattern was then exposed by dissolving the remaining photoresist on the substrate. Wire connections were made by bonding silver/copper wires to ITO pads using an electrically conductive adhesive (H37-MPT, Epoxy Technology, Inc.) heated at 150° C. for 1 hour (from manufacturer's product data sheet).

P19 cells were detached from the cell culture surface by trypsinization, centrifuged at 83.8 rad/s for 7 minutes at 5° C., and then resuspended in 0.32 mol/L sucrose. The cells were immediately introduced into the microfluidic channel covering the electrodes via the inlet reservoir. Approximately 150 μL of the cells resuspended (approximately 375,000 cells) in sucrose were added to the inlet that accessed the channel previously filled with the sucrose solution. A flow was produced when the cells were introduced due to the difference in pressure between the inlet and outlet reservoirs. Once the cells started to flow down the channel, a sine wave of up to 7 Vp-p was applied at a frequency of 30 MHz. The cells were exposed to the DEP forces for up to 4 minutes at which point the DEP electrodes were de-energized. Then, the cells/sucrose solution in the inlet reservoir was exchanged for cell culture media to replace the sucrose in the channel. The DEP device with the trapped cells in cell culture media was then placed in the incubator set at 37° C. and 5% CO2.

The cells were maintained by adding fresh cell culture media to the inlet reservoir every 24 h, and by removing the media collected in the outlet or waste reservoir at the same time. Images of the cells were taken every 24 h.

P19 cells are typically induced in suspension. However, the present approach requires the induction procedure to be carried out on a surface (hCAM) rather than in suspension. Therefore, P19 cells were first induced on tissue culture polystyrene (TCPS) to determine if it was feasible to induce them on a surface, and then the cells were induced on (PAH/PSS)2/FN and hCAM. The results on the three surfaces were then compared. Induction on all surfaces was carried out using the same conditions in terms of chemicals and days of induction. The only difference was the surface onto which the P19 cells were attached. The procedure that follows applied to all inductions. To induce the differentiation of P19 cells, the CCM was replaced by induction media (IM) comprised of ∝MEM supplemented with 5% FBS and retinoic acid at a final concentration of 0.5 μmol/L. IM was changed every 24 hours for a period of 4 days. On day 4, the IM was replaced with CCM, which in turn was replaced every 24 hours for two days. Cell differentiation was verified by using a fluorescently labeled antibody to stain for marker proteins associated with neuronal differentiation two days after cell induction was completed.

Differentiated P19 cells were fixed by first rinsing the cells with PBS and then adding 4% paraformaldehyde in PBS. The fixation was allowed to occur at room temperature for 10 minutes at which time the cells were rinsed with PBS. Cells were then permeabilized with a solution of 0.25% Triton X-100 in PBS and then incubated with the primary antibody (monoclonal antineurofilament) at a dilution of 1:40 for 3 hours at room temperature. The samples were rinsed with PBS and incubated at room temperature with a secondary antibody (antimouse IgG-FITC, Cat. No. F9137, Sigma-Aldrich) at a dilution of 1:200 for up to 90 min. The neurofilament staining was observed with a 200M Zeiss microscope using a mercury lamp source and a filter set with a band pass for excitation at 450 nm to 490 nm, a dichroic beam splitter at 510 nm, and a band pass for emission at 515 nm to 565 nm. The objective used had a 10× magnification and an aperture of 0.3. Images were taken using a Zeiss MRm camera.

Example 2

Fabrication of gold electrodes on a PET membrane is shown in FIG. 27. The PET membrane was first fixed onto a glass wafer using poly(methyl methacrylate) (PMMA) as adhesive, to prevent folding. Gold microelectrodes were fabricated on top of the PET membrane using conventional photolithographic and metallization techniques. The resulting microelectrodes were characterized by AFM, SEM, and optical microscopy. Polyelectrolyte multilayers (PEMs) were deposited onto the surface of the PET membrane containing the microelectrodes in order to trap and anchor cells. Subsequently, the microfluidic device was assembled and the microelectrodes were tested for cell capture by applying DEP forces. Cell viability was assessed 24 hours after cell capture.

Fixation of the PET membrane (11 μm thick, 1.2 μm pore size, 1.6×106 pores per cm2, cell culture treated, it4ip, Belgium) was necessary for photolithographic processing to prevent folding of the membrane and hence to avoid problems with the gold patterning. Therefore, 495 PMMA A 11 (MicroChem, Newton, Mass.) was spin coated onto a 4 inch (10.16 cm) glass wafer (Valley Design Corp., Shirley, Mass.) to a thickness of 2.25 μm. A piece of PET membrane of about 2 cm×2 cm was placed in the middle of the wafer, and then the wafer was baked at 110° C. for 5 min. For the bilayer lift-off process two different photoresists were spin coated onto the membrane. First, the membrane was coated with the lift-off resist LOR 3A (MicroChem, Newton, Mass.) to a thickness of 350 nm and baked at 155° C. for 10 min. Second, the positive tone photoresist 51813 (Rohm & Haas, Marlborough, Mass.) was spun to a thickness of 1.2 μm and baked at 110° C. for 5 min. Next, the wafer was exposed to UV-light (λ=405 nm) for 5 seconds (MA/BA6, SUSS MicroTec AG, Garching, Germany) to transfer the pattern of the microelectrodes (1000 μm long and 10 μm wide with gaps between opposite electrodes of 10 μm) onto the photoresist. Finally, the pattern was developed in MF-319 (Rohm & Haas, Marlborough, Mass.) for 60 s. Afterwards, the wafer was placed overnight under vacuum to allow complete drying of the membrane.

A 50 nm thick layer of gold was deposited onto the photolithographically processed wafer (E-bream evaporator Denton Infinity 22, Denton Vacuum LLC, Moorestown, N.J.). Redundant gold was lifted-off in 1165 remover (MicroChem, Newton, Mass.). To support and accelerate the process, agitation and short pulses of sonication (3 seconds to 5 seconds) were applied. The lift-off was completed within 5 minutes to 10 minutes. After the lift-off process the sample was blow dried. The dimensions of the microelectrodes after all processing steps varied slightly from the design pattern (electrodes widths of approximately 11 µm and gaps of approximately 9 µm).

The distance to which gold was deposited into the pores was assessed by imaging a total of 10 pores, randomly selected, with field-emission SEM (Ultra-60 FESEM, Zeiss, Germany). To obtain the distance to which gold was deposited into the pores, the difference in the working distances of two SEM images in the same pore were measured: the first image was focused on the surface of the membrane (as outer value), and the second one was focused on the deepest point inside the pore where gold was still seen (as inner value). The difference between the inner and outer working distances corresponded to the distance to which the gold was deposited inside the pore.

AFM images (Dimension 5000, Digital Instruments, Santa Barbara, Calif.) were acquired in tapping mode. Images were acquired at ambient conditions on dry samples. To obtain the differences in RMS roughness of the surfaces within the samples, seven independent areas of 10 µm×10 µm were imaged and then analyzed using the Nanoscope 7.3 software. The analyzed surfaces were: 1) membrane before processing; 2) membrane after processing; and 3) the gold patterned.

Contact angles were measured to characterize the hydrophilicity of the PET membrane during the processing. A drop of water was placed onto the sample, and a side view picture was taken. The droplet curvature was fitted using the software FTA32 (First Ten Angstroms, Inc., Portsmouth, Va.) to obtain the contact angle value. A contact angle between 0° and 90° was defined as a hydrophilic surface and a value between 90° and 180° as a hydrophobic surface. For each step during the electrode microfabrication the contact angle was averaged from four independent measurements.

The SU-8 master (SU-8 2025, MicroChem, Newton, Mass.) contained features for molding a microchannel out of PMDS (Sylgard 184, Dow Corning, Midland, Mich.) with a height of 30 µm and a width of 1000 µm. It was fabricated using the manufacturer's protocol. PDMS was cured on the SU-8 master after mixing the elastomer and curing agent at a ratio of 10:1, respectively. Once mixed and degassed, the mixture was poured onto the SU-8 wafer and cured for 4 hours at 65° C. Excessive PDMS was cut, and access holes of approximately 5 mm were punched. The PDMS microchannel was rinsed with 70% ethanol before it was assembled onto the substrate.

Figure 28:
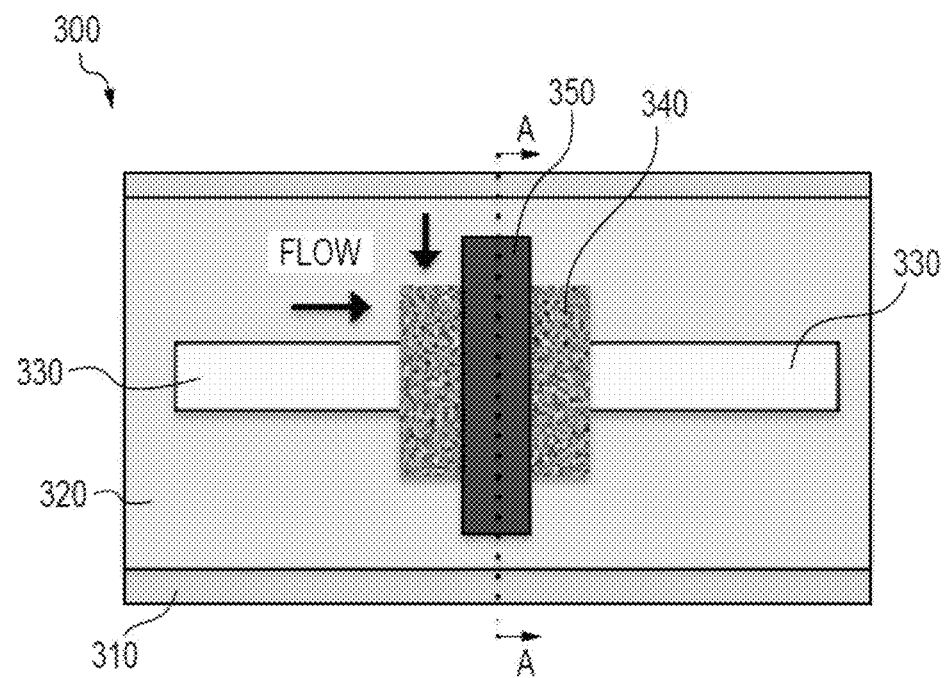
FIG. 28 shows a schematic top view of a microfluidic device including a PET membrane in accordance with the present subject matter.
Figure 29:
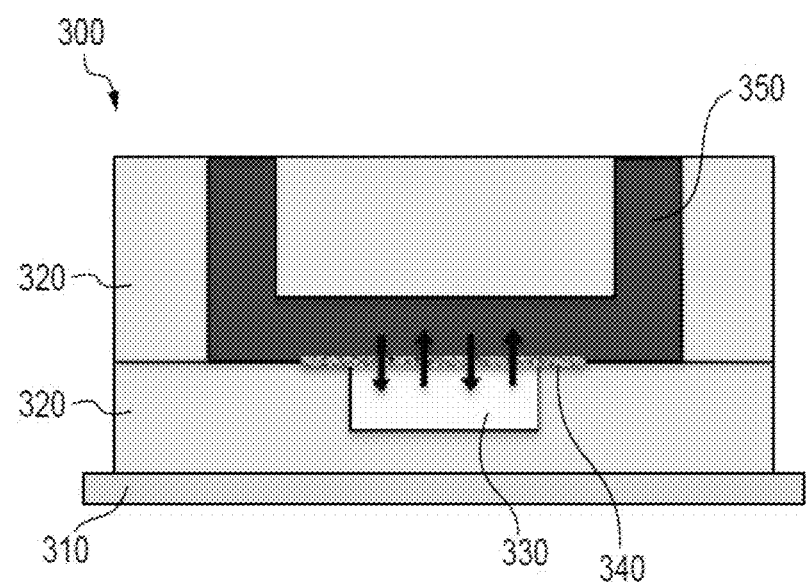
FIG. 29 shows a schematic cross sectional view of the device in FIG. 28 taken across line A-A.

A multilayer microfluidic device as shown in FIG. 28 and FIG. 29, was assembled to confirm that the permeability of the PET membrane was not affected during processing. The membrane was transferred onto a PDMS layer containing the top channel. Next, the PMMA was dissolved in acetone. The PDMS layer containing the membrane was plasma activated along with the PDMS layer containing the bottom channel. The membrane was sandwiched between both PDMS layers to complete the assembly of the device. Both layers contained a microfluidic channel of 30 µm in height and 1000 µm in width. These channels were perpendicularly aligned to each other, whereby the intermediate PET membrane allowed the exchange of reagents. Tubing was connected between the assembled microchip and syringe pumps (PHD 2000, Harvard Apparatus, PA). For the permeability test the flow rates varied between 0, 0.5 and 10 µl/min. Specifically, referring to FIG. 28 and FIG. 29, the processed PET membrane was aligned between the channels of the top and bottom PDMS layers. FIG. 28 indicates the flow directions in both channels. The assembled device is comprised of a glass substrate, the bottom PDMS layer, the membrane, and the top PDMS layer. The dashed line in the top view denotes the position at which the cross section of FIG. 29 is taken. The cross section indicates the area where the exchange of reagents between the channels was possible, only through the pores of the PET membrane (see arrows).

To enable cell anchorage and cell culture on chip after dielectrophoretic cell capture, the area of the membrane containing the microelectrodes was coated with PEMs as described in Reyes et al. Briefly, 5 µL of a 1 mg/mL poly(ethyleneimine) solution (Molecular Weight (MW) =70000, Polysciences, Inc., Warrington, Pa.) were placed on the microelectrodes. This first layer was incubated for 30 min, rinsed with water, and blow dried. Next, two bilayers of polyanion/polycation were deposited (polyanion=sodium poly(styrene sulfonate), MW=70000, Polysciences, Inc., Warrington, Pa.; and polycation=poly(allylamine hydrochloride), MW=70000, Sigma-Aldrich Corp., St. Louis, Mo.; 1 mg/mL each). Each layer was incubated for 10 min, rinsed with water, and blow dried. These procedures resulted in the deposition of a total of five layers of polyions on the microelectrodes.

NIH-3T3 mouse embryonic fibroblast cells were cultured in DMEM (Dulbecco's Modified Eagle's Medium) modified with 10% (v/v) bovine calf serum. Media was replaced every other day, and cells were subcultured when they were 80% confluent using 0.25% (w/v) trypsin (all reagents from ATCC, Manassas, Va.). For DEP experiments the cells were harvested in 0.147 mol/L sucrose (Sigma-Aldrich Corp., St. Louis, Mo.). Sucrose, a non-electrolyte, was used as low-conductive media to perform positive DEP, i.e., the cells were attracted by the DEP forces.

Wires were connected to the contact pads using an electrically conductive adhesive (Epoxy Technology Inc., Billerica, Mass.), cured for 1 hour at 150° C. Then, the membrane was coated with PEMs as previously described herein. Finally, the device was assembled by placing the cleaned PDMS microchannel on top of the microelectrodes, so that the channel was perpendicular to the microelectrodes. The assembled device was connected to a waveform generator (Agilent Technologies, Santa Clara, Calif.), and the channel was filled with 0.147 mol/L sucrose using capillary forces. 150 µL of the cell suspension were placed into the inlet of the microchannel. Suction was applied from the outlet to start the cell flow (linear velocity of approximately 550 µm/s). Cells were captured by applying a sine wave from 2 Vp-p to 5 Vp-p at a frequency of 10 MHz for less than 5 min. Subsequently, the cell/sucrose solution in the inlet was exchanged with cell culture media, and the device was placed in the incubator at 37° C. and 5% CO2. After 24 hours a live/dead assay (Live/Dead® viability/cytotoxicity kit, Invitrogen, Eugene, Oreg.) was performed as described in the manufacture's protocol. Briefly, before imaging, the cells were incubated in media containing 2 µmol/L Calcein AM and 4 µmol/L Ethidium homodimer-1 for 20 min. Green fluorescence indicated living cells and red fluorescence dead ones.

Additionally, cell adhesion and viability of NIH-3T3 cells was tested directly on glass, on PEMs on glass and in a cell culture flask. Therefore, the cells were seeded onto these surfaces and incubated for 24 hours at 37° C. and 5% CO2. Afterwards a live/dead assay was performed as described above.

Example 3

Water contact angles were measured at different points during the fabrication process to monitor changes in hydrophilicity of the PET membrane. The results of this evaluation are presented below in Table 1.

TABLE 1

Water contact angles of the PET membrane (n = 4).

| Point of Measurement | Contact Angle [°] |
|---|---|
| before processing | 86 ± 1 |
| on PMMA | 74 ± 1 |
| after development | 73 ± 1 |
| after lift-off | 69 ± 2 |

To compare the NIH-3T3 cell behavior on our PEMs/PET membrane with standard cell culture, cell adhesion and viability on other surfaces, i.e., directly on glass, were assessed for PEMs on glass and on cell culture flask polystyrene (FIG. 30). A live/dead assay revealed about 99% of living cells after 24 h. The cells showed similar behavior when seeded on the other surfaces to cells on the PET membrane, i.e., the different surfaces have no influence on cell adhesion and viability. Specifically, FIG. 30 shows cell adhesion and viability on standard cell culture surfaces. The behavior of NIH-3T3 cells did not significantly differ on the various surfaces. After 24 hours approximately 99% of the cells were alive. The scale bars in the squares are each 50 µm.

While one or more embodiments have been shown and described, modifications and substitutions may be made thereto without departing from the spirit and scope of the invention. Accordingly, it is to be understood that the present invention has been described by way of illustrations and not limitation. Embodiments herein can be used independently or can be combined.

Reference throughout this specification to "one embodiment," "particular embodiment," "certain embodiment," "an embodiment," or the like means that a particular feature, structure, or characteristic described in connection with the embodiment is included in at least one embodiment. Thus, appearances of these phrases (e.g., "in one embodiment" or "in an embodiment") throughout this specification are not necessarily all referring to the same embodiment, but may. Furthermore, particular features, structures, or characteristics may be combined in any suitable manner, as would be apparent to one of ordinary skill in the art from this disclosure, in one or more embodiments.

All ranges disclosed herein are inclusive of the endpoints, and the endpoints are independently combinable with each other. The ranges are continuous and thus contain every value and subset thereof in the range. Unless otherwise stated or contextually inapplicable, all percentages, when expressing a quantity, are weight percentages. The suffix "(s)" as used herein is intended to include both the singular and the plural of the term that it modifies, thereby including at least one of that term (e.g., the colorant(s) includes at least one colorants). "Optional" or "optionally" means that the subsequently described event or circumstance can or cannot occur, and that the description includes instances where the event occurs and instances where it does not. As used herein, "combination" is inclusive of blends, mixtures, alloys, reaction products, and the like.

As used herein, "a combination thereof" refers to a combination comprising at least one of the named constituents, components, compounds, or elements, optionally together with one or more of the same class of constituents, components, compounds, or elements.

All references are incorporated herein by reference.

The use of the terms "a" and "an" and "the" and similar referents in the context of describing the invention (especially in the context of the following claims) are to be construed to cover both the singular and the plural, unless otherwise indicated herein or clearly contradicted by context. "Or" means "and/or." Further, the conjunction "or" is used to link objects of a list or alternatives and is not disjunctive; rather the elements can be used separately or can be combined together under appropriate circumstances. It should further be noted that the terms "first," "second," "primary," "secondary," and the like herein do not denote any order, quantity, or importance, but rather are used to distinguish one element from another. The modifier "about" used in connection with a quantity is inclusive of the stated value and has the meaning dictated by the context (e.g., it includes the degree of error associated with measurement of the particular quantity).

What is claimed is:

1. A dual dielectropheretic article for monitoring cell migration, the dual dielectropheretic article comprising:
    a membrane to selectively migrate a plurality of cells across the membrane, the membrane comprising:
        a first surface to receive the cells;
        a second surface opposed to the first surface; and
        a plurality of communication paths disposed in the membrane to provide the selective migration of the cells across the membrane from the first surface to the second surface;
    a first electrode disposed on the first surface to:
        provide an electric field for dielectrophoresis of the cells at the first surface; and
        provide a first potential for monitoring an impedance at the first surface;
    a third electrode disposed on the second surface to:
        provide an electric field for dielectrophoresis of the cells at the second surface; and
        provide a third potential for monitoring an impedance at the second surface,
    a second electrode disposed on the first surface to:
        provide the electric field, in combination with the first electrode, for dielectrophoresis of the cells at the first surface; and
        provide a second potential for monitoring the impedance at the first surface; and
    a fourth electrode disposed on the second surface to:
        provide the electric field, in combination with the third electrode, for dielectrophoresis of the cells at the second surface; and
        provide a fourth potential for monitoring the impedance at the second surface.

2. The dual dielectropheretic article of claim 1, further comprising:
    a substrate on which the membrane is disposed.

3. The dual dielectropheretic article of claim 2, further comprising:
    a first flow channel disposed on the substrate and in fluid communication with the first surface to provide the cells to the first surface for dielectrophoresis of the cells at the first surface and selective migration through the membrane from the first surface to the second surface.

4. The dual dielectropheretic article of claim 2, further comprising:
    a second flow channel disposed on the substrate and in fluid communication with the second surface to receive the cells from the second surface after selective migration of the cells to the second surface from the first surface via communication of the cells through the membrane.

5. The dual dielectropheretic article of claim 3, further comprising:

a first probe electrode disposed on the substrate and in electrical communication with the first flow channel to provide a fifth potential for monitoring, in combination with the first electrode, the impedance at the first surface of the membrane,
wherein the first probe electrode is spatially separated from the membrane.

6. The dual dielectropheretic article of claim 4, further comprising:
a second probe electrode disposed on the substrate and in electrical communication with the second flow channel to provide a sixth potential for monitoring, in combination with the third electrode, the impedance at the second surface of the membrane,
wherein the second probe electrode is spatially separated from the membrane.

7. The dual dielectropheretic article of claim 1, further comprising:
a substrate on which the membrane is disposed;
a first flow channel disposed on the substrate and in fluid communication with the first surface to provide the cells to the first surface for dielectrophoresis of the cells at the first surface and selective migration through the membrane from the first surface to the second surface;
a second flow channel disposed on the substrate and in fluid communication with the second surface to receive the cells from the second surface after selective migration of the cells to the second surface from the first surface via communication of the cells through the membrane;
a first probe electrode disposed on the substrate and in electrical communication with the first flow channel to provide a fifth potential for monitoring, in combination with the first electrode, the impedance at the first surface of the membrane, wherein the first probe electrode is spatially separated from the membrane; and
a second probe electrode disposed on the substrate and in electrical communication with the second flow channel to provide a sixth potential for monitoring, in combination with the third electrode, the impedance at the second surface of the membrane,
wherein the second probe electrode is spatially separated from the membrane.

8. The dual dielectropheretic article of claim 7, further comprising:
an impedance analyzer in electrical communication with the first electrode and the second electrode.

9. The dual dielectropheretic article of claim 8, wherein:
the impedance analyzer further is in electrical communication with the first probe electrode and the second probe electrode;
the impedance at the first surface is with respect to an impedance between the first electrode and the first probe electrode; and
the impedance at the second surface is with respect to an impedance between the third electrode and the second probe electrode.

10. The dual dielectropheretic article of claim 8, wherein:
the impedance analyzer further is in electrical communication with the second electrode and the fourth electrode;
the impedance at the first surface is with respect to an impedance between the first electrode and the second electrode; and
the impedance at the second surface is with respect to an impedance between the third electrode and the fourth electrode.

11. The dual dielectropheretic article of claim 8, wherein the impedance at the first surface and the impedance at the second surface is with respect to an impedance between the first electrode and the third electrode.

12. The dual dielectropheretic article of claim 4, further comprising:
an optical objective disposed proximate to the second flow channel and second surface and in optical communication with the second surface,
wherein the optical objective comprises a field of view that includes the second surface such that cells received at the second surface by communication from the first surface through the membrane are within the field of view of the optical objective.

13. The dual dielectropheretic article of claim 1, further comprising:
a cell adhesive material disposed on the first surface, the second surface, or a combination of the first surface and the second surface, the cell adhesive material to adhere cells to the first surface, the second surface, or the combination of the first surface and the second surface on which the cell adhesive material is disposed,
wherein the cell adhesive material comprises an extracellular matrix component, a polyelectrolyte, or a combination comprising at least one of the foregoing cell adhesive materials.

14. The dual dielectropheretic article of claim 1, wherein the communication path comprises an open pore.

15. The dual dielectropheretic article of claim 14, wherein the open pores comprise a diameter from 2 nm to 100 μm to provide selective migration of cells across the membrane from the first surface to the second surface.

16. The dual dielectropheretic article of claim 14, wherein the open pores are disposed in an ordered arrangement in the membrane.

17. The dual dielectropheretic article of claim 14, wherein the open pores are disposed in a random arrangement in the membrane.

18. The dual dielectropheretic article of claim 1, wherein the first electrode and the third electrode independently comprise a metal, an electrically conductive polymer, an electrically conductive glass, an electrically conductive ceramic, an electrically conductive semiconductor, or a combination comprising at least one of the foregoing electrically conductive materials.

19. A process for determining impedance in a dual dielectropheretic article, the process comprising:
providing the dual dielectropheretic article of claim 9;
providing a first alternating current (AC) voltage to one of the first electrode or the first probe electrode;
monitoring a first electrical response of the first electrode or the first probe electrode that was not provisioned with the first AC voltage;
providing a second AC voltage to one of the third electrode or the second probe electrode;
monitoring a second electrical response of the third electrode or the second probe electrode that was not provisioned with the second AC voltage; and
converting the first electrical response to the impedance at the first surface to determine the impedance of the dual dielectropheretic article.

20. The process for determining impedance in a dual dielectropheretic article of claim 19, further comprising converting the second electrical response to the impedance at the second surface.

* * * * *